US007314712B2

(12) United States Patent
Storici et al.

(10) Patent No.: US 7,314,712 B2
(45) Date of Patent: Jan. 1, 2008

(54) SYSTEMS FOR IN VIVO SITE-DIRECTED MUTAGENESIS USING OLIGONUCLEOTIDES

(75) Inventors: Francesca Storici, Durham, NC (US); Lysle Kevin Lewis, San Marcos, TX (US); Michael A. Resnick, Chapel Hill, NC (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 277 days.

(21) Appl. No.: 10/484,989

(22) PCT Filed: Jul. 26, 2002

(86) PCT No.: PCT/US02/23634

§ 371 (c)(1),
(2), (4) Date: Jan. 26, 2004

(87) PCT Pub. No.: WO03/012036

PCT Pub. Date: Feb. 13, 2003

(65) Prior Publication Data

US 2004/0171154 A1    Sep. 2, 2004

Related U.S. Application Data

(60) Provisional application No. 60/308,426, filed on Jul. 27, 2001.

(51) Int. Cl.
*C12Q 1/68* (2006.01)
*G01N 33/567* (2006.01)
*G01N 3/569* (2006.01)
*C07H 21/04* (2006.01)
*C12N 15/63* (2006.01)

(52) U.S. Cl. .................. 435/6; 435/7.21; 435/7.31; 536/23.1

(58) Field of Classification Search .................... None
See application file for complete search history.

(56) References Cited

U.S. PATENT DOCUMENTS

| | | | |
|---|---|---|---|
| 4,626,504 A | 12/1986 | Puhler et al. | |
| 5,942,422 A | 8/1999 | Rothstein | |
| 5,945,339 A | 8/1999 | Holloman et al. | |
| 6,200,812 B1 | 3/2001 | Pati et al. | |
| 6,562,594 B1 | 5/2003 | Short | |

FOREIGN PATENT DOCUMENTS

| | | |
|---|---|---|
| AU | 757930 | 6/1999 |
| EP | 0919619 | 6/1999 |
| WO | WO 90/14092 | 11/1990 |
| WO | WO 96/41008 | 12/1996 |
| WO | WO/0234881 | 5/2002 |

OTHER PUBLICATIONS

Guldener et al. A new efficient gene disruption cassette for repeated use in budding yeast. Nuc. Acid Res., 24: 2519-2524, 1996.*
Kuroiwa et al. Efficient modification of a human chromosome by telomere-directed truncation in high homologous recombination-proficient chicken DT40 cells. Nuc.Acid Res., 26: 3447-3448, 1998.*
Muyrers et al. Techniques: Recombinogenic engineering-new options for cloning and manipulating DNA. Trends in Biochem. Sci., 26(5): 325-331, 2001.*
Springer et al. Gene Traps: Tools for plant development and genomics. Plant Cell 12: 1007-1020, 2000.*
Wach et al. Heterologous HIS3 marker and GFP reporter modules for PCR-targeting in *Saccharomyces cerevisiae*. Yeast, 13: 1065-1075, 1997.*
Hogger e al. Activating and Inactivating Mutations in N- and C-terminal i3 Loop Junctions of Muscarinic Acetylcholine Hml Receptors. J. Biol. Chem 270(13): 7405-7410, 1995.*
Biet et al., "Stimulation of RecA-Mediated D-Loop Formation by Oligonucleotide-Directed Triple-Helix Formation: Guided Homologous Recombination(GOREC)," *Biochemistry*, 40: 1779-1786, 2001.
Duno et al., "Targeted deletions created in yeast vectors by recombinational excision," *Nucleic Acids Res.*, 27: e1(5 pages), Apr. 15, 1999.
Inga and Resnick, "Novel human p53 mutations that are toxic to yeast can enhance transactivation of specific promoters and reactivate tumor p53 mutants," *Oncogene*, 20: 3409-3419, 2001.
Li et al., "Generation of mice with a 200-kb amyloid precursor protein gene deletion by Cre recombinase mediated site-specific recombination in embryonic stem cells," *Proc. Natl. Acad. Sci.*, 93:6158-6162, Jun. 1996.
Aguilera and Klein, "Genetic control of intrachromosomal recombination in *Saccharomyces cerevisiae*," I. Isolation and genetic characterization of hyper-recombination mutations, *Genetics*, 119(4):779-790 Aug. 1988 Abstract Only.
Aguilera and Klein, "Genetic and molecular analysis of recombination events in *Saccharomyces cerevisiae* occuring in the presence of the hyper-recombination mutation *hpr 1*," *Genetics*, 122(3):503-517, Jul. 1989 Abstract Only.

(Continued)

*Primary Examiner*—Joseph Woitach
*Assistant Examiner*—Michele K. Joike
(74) *Attorney, Agent, or Firm*—Klarquist Sparkman, LLP.

(57) ABSTRACT

This disclosure provides several methods to generate nucleic acid mutations in vivo, for instance in such a way that no heterologous sequence is retained after the mutagenesis is complete. The methods employ integrative recombinant oligonucleotides (IROs). Specific examples of the described mutagenesis methods enable site-specific point mutations, deletions, and insertions. Also provided are methods that enable multiple rounds of mutation and random mutagenesis in a localized region. The described methods are applicable to any organism that has a homologous recombination system.

78 Claims, 9 Drawing Sheets

OTHER PUBLICATIONS

Aguilera and Klein, "HPR1, a novel yeast gene that prevents intrachromosomal excision recombination, shows carboxy-terminal homology to the *Saccharomyces cerevisiae* TOP1 gene," *Mol Cell Biol*, 10(4):1439-1451, Apr. 1990 Abstract Only.

Bressan et al., "The Mre11-Rad50-Xrs2 Protein Complex Facilitates Homologous Recombination-Based Double-Strand Break Repair in *Saccharomyces cerevisiae*," *Molecular and Cellular Biology*, 19(11):7681-7687, Nov. 1999.

Duno et al., "Targeted deletions created in yeast vectors by recombinational excision," *Nucleic Acids Res.*, 27(8):e1, Apr. 15, 1999 Abstract Only.

Erdeniz et al., "Cloning-Free PCR-Based Allele Replacement Methods," *Genome Research*, 7:1174-1183, 1997.

Gallardo and Aguilera, "A New Hyperrecombination Mutation Identifies a Novel Yeast Gene, *THP1*, Connecting Transcription Elongation with Mitotic Recombination," *Genetics*, 157:79-89, Jan. 2001.

Goldstein et al., "Yeast Functional Analysis Reports," *Yeast*, 15:507-511, 1999.

Granger and Cyr, "Characterization of the yeast copper-inducible promoter system in *Arabidopsis thaliana*," *Plant Cell Reports*, 20:227-234, 2001.

Hua et al., "Minimum length of sequence homology required for in vivo cloning by homologous recombination in yeast," *Plasmid*, 38(2):91-96, 1997 Abstract Only.

Inga and Resnick, "Novel human p53 mutations that are toxic to yeast can enhance transactivation of specific promoters and reactivate tumor p53 mutants," *Oncogene*, 20(26):3409-3419, Jun. 7, 2001 Abstract Only.

Medlin, Jennifer, "Foreign DNA Disappears without a Trace," *Environmental Health Perspectives*, 110(2):A89-A91, Feb. 2002.

Moerschell et al., "Transformation of yeast with synthetic oligonucleotides," *Proc. Natl. Acad. Sci.*, 85:524-528, Jan. 1988.

Olden, et al., "Recombination-mediated PCR-directed plasmid construction in vivo in yeast," *Nucleic Acids Res.*, 25(2):451-452, Jan. 15, 1997 Abstract Only.

Rong et al., "Targeted mutagenesis by homologous recombination in *D. melanogaster*," *Genes & Development*, 16:1568-1581, 2002.

Schneiter et al., "The *Saccharomyces cerevisiae* Hyperrecombination Mutant *hpr 1* ΔIs Synthetically Lethal with Two Conditional Alleles of the Acetyl Coenzyme A Carboxylase Gene and Causes a Defect in Nuclear Export of Polyadenylated RNA," *Molecular and Cellular Biology*, 19(5):3415-3422, May 1999.

Storici et al., "Chromosomal site-specific double-strand breaks are efficiently targeted for repair by oligonucleotides in yeast," *PNAS*, 100(25):14994-14999, Dec. 9, 2003.

Storici et al., "In vivo site-directed mutagenesis using oligonucleotides," *Nature Biotechnology*, 19:773-776, Aug. 2001.

Swaminathan et al., "Rapid Engineering of Bacterial Artificial Chromosomes Using Oligonucleotides," *Genesis*, 29:14-21, 2001.

Symington et al., "Alteration of gene conversion tract length and associated crossing over during plasmid gap repair in nuclease-deficient strains of *Saccharomyces cerevisia*," *Nucleic Acids Res.*, 28(23):4649-4656, Dec. 1, 2000 Abstract Only.

Szent-Gyorgyi, "A Simplified Method for the Repeated Replacement of Yeast Chromosomal Sequences with in vitro Mutations," *Yeast*, 12:667-672, 1996.

Tishkoff et al., "Identification and characterization of *Saccharomyces cerevisiae EXO1*, a gene encoding an exonuclease that interacts with MSH2," *Proc. Natl. Acad. Sci. USA*, 94:7487-7492, Jul. 1997.

Tran et al., "The 3'→5' Exonucleases of DNA Polymerase δ and ε and the 5'→3' Exonuclease Exo1 Have Major Roles in Postreplication Mutation Avoidance in *Saccharomyces cerevisiae*," *Molecular and Cellular Biology*, 19(3):2000-2007, Mar. 1999.

Wilson et al., "Rapid hypothesis testing with *Candida albicans* through gene disruption with short homology regions," *J. Bacteriol.*, 181(6):1868-1874, Mar. 1999 Abstract Only.

Yamamoto, et al., "Parameters Affecting the Frequencies of Transformation and Co-transformation with Synthetic Oligonucleotides in Yeast," *Yeast*, 8:935-948, 1992.

Yu et al., "An efficient recombination system for chromosome engineering in *Escherichia coli*," *PNAS*, 97(11):5978-5983, May 23, 2000.

Zhang et al., "A new logic for DNA engineering using recombination in *Escherichia coli*," *Nature Genetics*, 20:123-128 (1998).

Nefedov et al., "Insertion of disease-causing mutations in BACs by homologous recombination in *Escherichia coli*," *Nucleic Acids Research*, 28(17)e79:1-4 (2000).

Muyrers et al., "Point mutation of bacterial artificial chromosomes by ET recombination," *EMBO Reports*, 1(3):239-243 (2000).

\* cited by examiner

Step 1:
Insert CORE

Step 2:
Add IROs

Precise Deletion

Specific Mutation

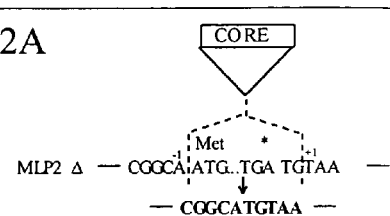
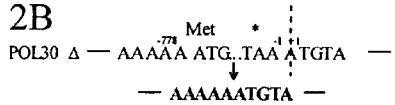
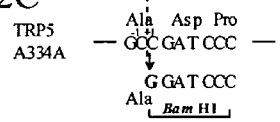
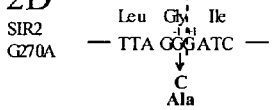
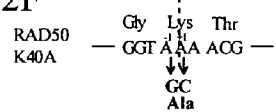
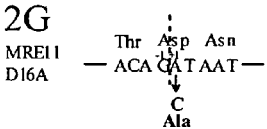

SYSTEMS FOR IN VIVO SITE-DIRECTED MUTAGENESIS USING OLIGONUCLEOTIDES

PRIORITY CLAIM

This is a § 371 U.S. National Stage of PCT/US02/23634, filed Jul. 26, 2002 (published in English under PCT Article 21(2)), which in turn claims the benefit of U.S. Provisional Patent Application 60/308,426, filed Jul. 27, 2001. Both applications are incorporated here in their entirety.

FIELD

This disclosure relates to methods of in vivo site-directed mutagenesis, particularly mutagenesis mediated by oligonucleotides. It further relates to methods of in vivo site-directed mutagenesis that are stimulated by double-strand breaks induced in vivo and mediated by oligonucleotides.

BACKGROUND OF THE DISCLOSURE

The combination of genome sequencing along with commonality of genetic function across species is providing an opportunity to characterize the genes of higher organisms in two ways: by analyzing site-specific changes in homologous genes in model systems and through analysis of higher eukaryotic genes cloned within model organisms. The yeast *Saccharomyces cerevisiae* has proven ideal for many cross-species studies. The growing body of knowledge and techniques that have made it the best-characterized eukaryotic genome (Dujon, *Trends Genet.* 12, 263-270, 1996; Hieter et al., *Nat. Genet* 13, 253-255, 1996; Resnick and Cox, *Mutat. Res.* 451, 1-11, 2000; Shashikant et al., *Gene* 223, 9-20, 1998) also allow the experimental manipulation of large heterologous genomic DNA fragments cloned into yeast artificial chromosomes (YACs) (Anand, *Trends Biotechnol.* 10, 35-40, 1992, Larionov et al, *Proc. Natl. Acad. Sci. USA* 94, 7384-7387, 1997; Brown et al., *Trends Biotechnol.* 18, 218-23, 2000).

While it is possible in yeast to modify natural chromosomes or YACs without leaving behind any heterologous sequence, present systems have limited flexibility and are laborious. For example, null mutations are usually made in yeast by gene replacement, such that a marker gene replaces the sequence that is deleted (Wach et al., *Yeast* 10, 1793-1808, 1994). Marker recycling procedures, based on homologous or site-specific recombination or religation of DNA ends, also leave heterologous material at the deleted locus, such as hisG (Alani et al, *Genetics* 116, 541-545, 1987), FRT (Storici et al., *Yeast* 15, 271-283, 1999), loxP (Delneri et al., *Gene* 252, 127-135, 2000), or I-SceI (Fairhead et al., *Yeast* 12, 1439-1457, 1996) sequences. To accomplish sequence modification such that no heterologous material is retained requires subcloning and in vitro mutagenesis (Scherer and Davis, *Proc. Natl. Acad. Sci. USA* 76, 4949-4955, 1979; Barton et al., *Nucleic Acids Res.* 18, 7349-7355, 1990). PCR-based procedures that do not involve cloning are inefficient or require multistep reactions which increase the risk of additional mutations (Langle-Rouault and Jacobs, *Nucleic Acids Res.* 23, 3079-3081, 1995; Erdeniz et al., *Genome Res.* 7, 1174-1183, 1997). An alternative approach has been demonstrated in yeast for the CYC1 gene that relies on transformation with an oligonucleotide (Moerschell et al., *Proc. Natl. Acad. Sci. USA* 85, 524-528, 1988), but the method is restricted to the generation of mutants with a selectable phenotype and appears to be target dependent (Kmiec, "Targeted gene repair" [editorial], *Gene Ther.* 6, 1-3, 1999). Oligonucleotides, when combined with gap repair, can also be used to modify plasmids in yeast (Duno et al., *Nucleic Acids Res.* 27:e1, 1999); however, this approach is limited by restriction site availability.

SUMMARY OF THE DISCLOSURE

This disclosure provides simple and effective methods that use purified or unpurified oligonucleotides to generate specific mutations in vivo, for instance, in yeast chromosomal DNAs, in such a way that no heterologous sequence is retained after the mutagenesis is complete. Specific methods provide for site-specific mutagenesis, including single or multiple point mutations, short deletions, or short insertions. Also provided are methods for more extensive deletions of precise nucleic acid sequences. A variety of individual and complementary oligonucleotides have been examined, and parameters that influence site-directed mutagenesis (e.g., oligonucleotide length) are described. Also provided are methods that enable multiple rounds of mutation and random mutagenesis in a localized region. The mutagenesis approaches are applicable to all organisms where homologous recombination is or can be carried out.

The two-step, cloning-free methods generate mutated products in vivo having only the desired mutation, such as single or multiple base changes, an insertion, or a small or a large deletion. Delitto perfetto (idiom used to represent "perfect deletion") mutagenesis is extremely versatile. It enables multiple rounds of specific or random changes within a specified window of 200 bp or more. Since yeast is commonly used for random and selective cloning of genomic DNA from higher eukaryotes such as YACs, this strategy also provides an efficient way to create precise changes within mammalian or other heterologous DNA sequences.

This disclosure further provides tools, including specific cassettes and classes of cassettes, that expand the applicability of the delitto perfetto system to virtually all yeast strains, independent from their genetic background. Specific embodiments include creation of large chromosomal deletions, up to 16 kb deletions having high accuracy. A set of four alternative specific CORE-cassettes are disclosed, which can be used to make the system applicable for all haploid yeast strains, including wild type non-auxotrophic strains.

In addition to the common heterologous URA3Kl, G418, and Hygromycin resistance genes, a novel counter-selectable marker is developed and disclosed, based on the human p53 allele V122A (Inga et al., *Oncogene* 20: 3409-3419, 2001). The delitto perfetto mutagenesis system can be used in diploid as well as haploid strains. The altered transactivation specificity of this allele prevents growth when overexpressed, without affecting genome stability.

In addition, this disclosure presents modifications of the delitto perfetto system that provides dramatically improved recombination efficiency, in some embodiments over 1000-fold increase in efficiency. These embodiments, using methods termed generally delitto perfetto-DSB, exploit the use of induced site-specific DSBs in the genome to increase oligonucleotide targeted mutagenesis. Specific examples of DSB-enhanced delitto perfetto mutagenesis do not require, and do not include, the use of a counterselectable marker.

The foregoing and other features and advantages will become more apparent from the following detailed description of several embodiments, which proceeds with reference to the accompanying figures.

In Step 1 for both of the illustrated embodiments, a CORE (COunterselectable REporter) cassette with KlURA3 (counterselectable) and kanMX4 (reporter) is inserted by standard DNA targeting procedures at a DNA sequence. In these embodiments, the insertion site is anywhere in the sequence that has been chosen to be deleted or is close to a site where a specific mutation is to be created.

In Step 2, transformation of cells that contain the CORE-cassette with IROs leads to loss of the CORE-cassette and (1) deletion of the desired region or (2) introduction of the desired mutation (*). Generic DNA sequences are indicated as stippled or striped boxes. In the illustrated embodiments, the IROs have a short overlap.

FIG. 2 illustrates several specific changes produced in the indicated sequences by transformation with IROs.

Target loci within MLP2 (A), POL30 (B), TRP5 (C), SIR2 (D, E), RAD50 (F), and MRE11 (G) are shown, together with their wild-type nucleotide and amino acid sequence. Asterisks (*) indicate stop codons. DNA sequence changes and the corresponding amino acid substitutions are shown in boldface below the arrows. Vertical dashed lines indicate the position in each sequence at which the CORE-cassette was integrated to carry out the indicated mutation. The small numbers above each wild-type DNA sequence correspond to the nucleotide position relative to the place at which the CORE-cassette was integrated.

Figure 3:
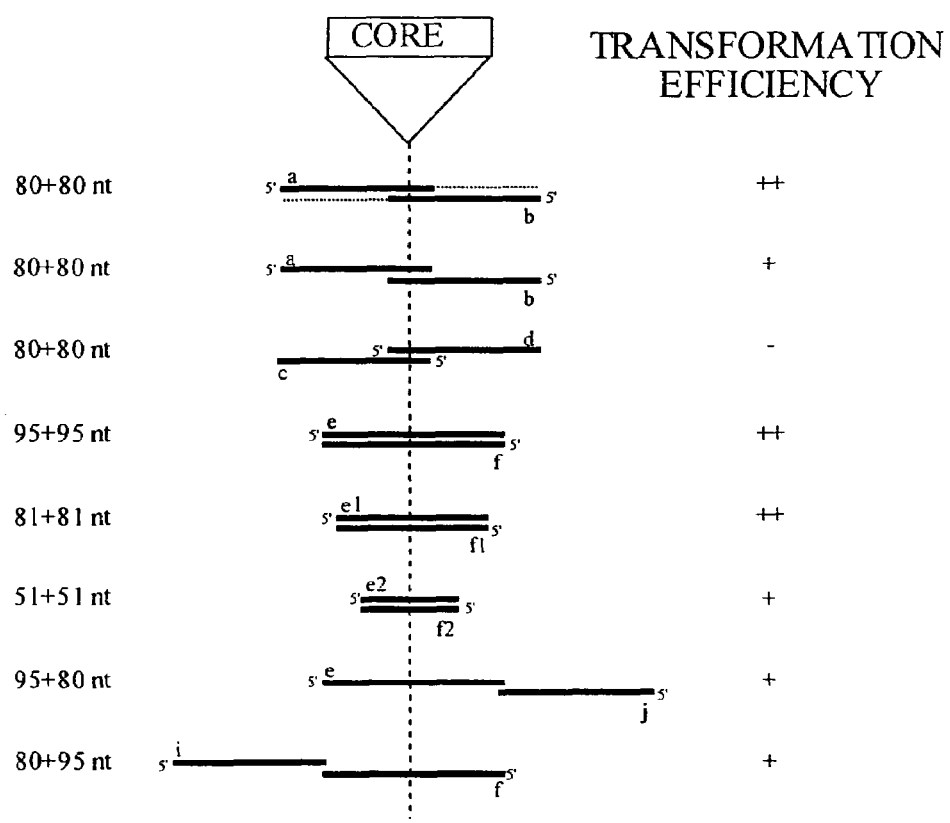

FIG. 3 shows the structure of several types of IROs used singly or as pairs to produce in vivo mutations as described in the examples, as well as indicating the relative transformation efficiency of the illustrated systems.

IROs a and b overlap for 20 bases at their 3' ends, while c and d overlap for 20 bases at their 5' ends; e and f, e1 and f1, and e2 and f2 overlap completely. IRO pairs e+j or f+i do not overlap each other. IRO-nucleotide lengths are shown on the left.

The horizontal dotted lines indicate in vitro extension of the a+b oligonucleotide pair with Pfx polymerase. The vertical dashed line separates sequences within IROs that are homologous to the upstream or the downstream regions of the CORE-cassette integration point, respectively (and thus indicates where the CORE-cassette existed prior to its loss).

A qualitative summary of the transformation efficiencies are presented to the right of the various IROs; ++, + and –, indicate high, moderate or very low efficiency, respectively.

FIG. 4 shows the specific frequencies of 5-FOA$^R$ G418$^s$ clones per $10^7$ cells in transformation experiments with single IROs (A) or with pairs of IROs (B) in the strain BY4742-TRP5-CORE and the isogenic rad52 strain. Vertical bars represent the 95% confidence interval values from 3 to 6 determinations.

The types of IROs analyzed are indicated below each bar (IROs are as illustrated in FIG. 3). Pfx indicates that the oligonucleotides were subjected to in vitro extension prior to transformation, and rad52 indicates results obtained with the rad52 strain. The amount of each oligonucleotide used was 0.5 nmoles, unless otherwise indicated (2× or 10×). Beneath each bar is the mean value of the number of 5-FOA$^R$ G418$^s$ clones/$10^7$ cells followed by the mean value of the Trp$^+$ clones and finally by the % Trp$^+$ among the 5-FOA$^R$ G418$^s$ clones. Abbreviations: n.c., negative control (no IRO DNA); NA, not applicable.

Among the G418$^s$ integrants the proportion of Trp$^+$ clones was high, indicating that additional TRP5 inactivating point mutations were infrequent. Five random Trp$^+$ clones for each type of IRO used were tested and shown to contain the expected BamHI bands, demonstrating that the desired mutation was successfully inserted to the TRP5 gene. Of nine Trp$^-$ G418$^s$ clones randomly chosen for sequencing, all had a frameshift mutation confined into the IRO region.

FIG. 5 shows schematic representations of three embodiments of the delitto perfetto mutagenesis strategy, illustrating some of the versatility of the technique for rapidly producing a variety of mutations.

Figure 5A:
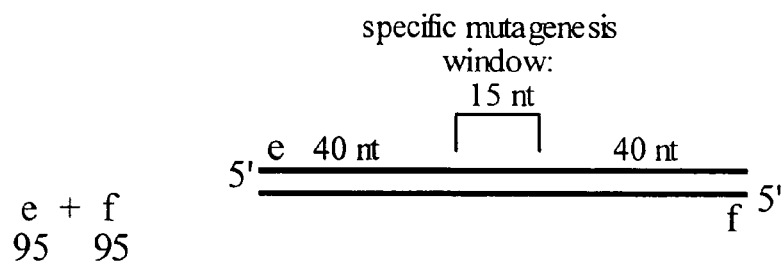

FIG. 5A shows an embodiment in which complementary 95-mers e+f have a central region of 15 nt that can be used for site-directed mutations. 40 nt at each end of the IROs (upstream and downstream of the CORE-cassette integration site) remain unchanged in certain embodiments for efficient homologous integration.

Figure 5B:
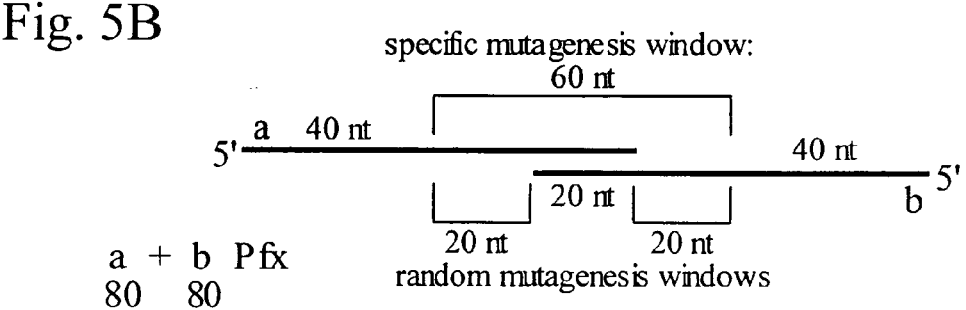

FIG. 5B shows an embodiment in which 80-mers a+b filled in with Pfx have a 60 nt region that can be mutagenized. Of these 60 nt, 20 nt to each side of the overlap also can be designed for random mutagenesis. As in FIG. 5A, 40 nt at each end remain unchanged in certain embodiments for efficient homologous integration.

Figure 5C:
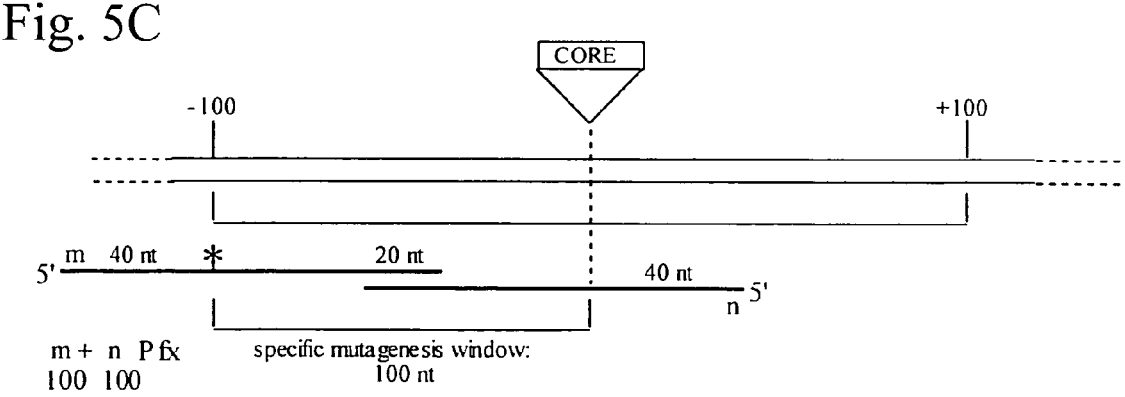

FIG. 5C illustrates an embodiment in which site-specific mutations can be introduced up to 100 bp upstream or downstream of the CORE-cassette integration point with different pairs of 80-100-mers (referred to here as m+n Pfx, analogous to a+b Pfx or to e+f), without moving the integrated CORE-cassette.

The drawing shows an example of oligonucleotides designed to introduce a mutation (*) 100 bp upstream of the CORE-cassette integration point with IROs m+n Pfx. The efficiency of mutagenesis may decrease as the mutation position in the IRO sequence is placed closer to the 5' end, since an IRO recombination event leading to excision of the CORE could occur without inclusion of the mutation in the IRO.

FIG. 6 illustrates an example strategy for in vivo site-specific targeting of mutations across the DNA binding domain of p53.

Seven isogenic strains are created each with a CORE-cassette integrated at a different position within the DNA binding domain of p53; the construction of strain 1 (FIG. 6A), strain 2 (FIG. 6B), and strain 7 (FIG. 6C) is shown.

Figure 6A:
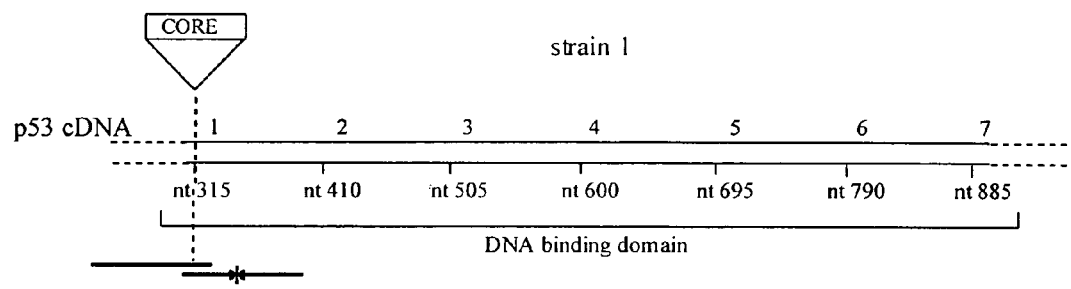
Figure 6B:
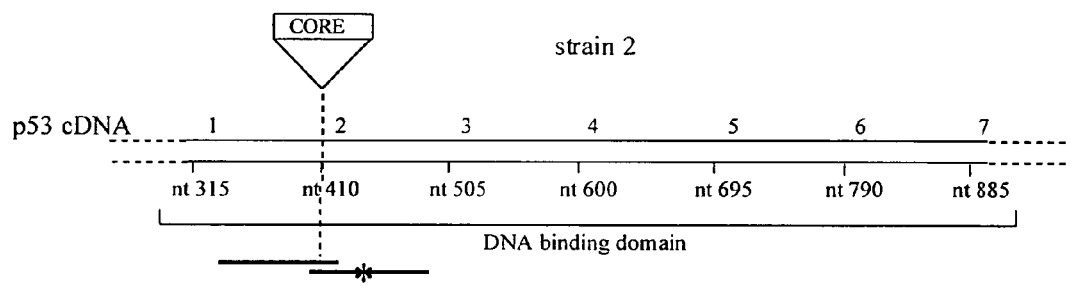
Figure 6C:
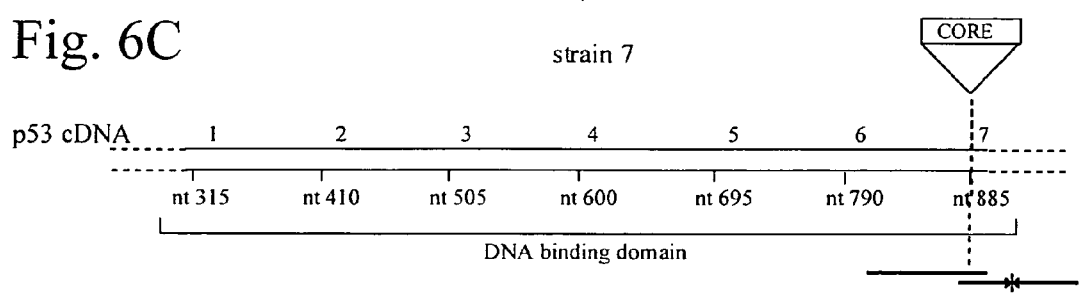

The p53 mutations can be created simply by designing oligonucleotides that contain the desired mutation. Transformation with 20 bp overlapping oligonucleotides that are homologous to a region surrounding the CORE-cassette results in the elimination of the CORE-cassette and creation of a site-specific change. A mutation can be designed 45 base pair upstream and downstream of each CORE-cassette insertion point. The specific illustrated embodiments show the introduction of a mutation downstream from a CORE-cassette that was inserted at nucleotide 315 (strain 1; FIG. 6A), nucleotide 410 (strain 2; FIG. 6B) or nucleotide 885 (strain 7; FIG. 6C).

Figure 7:
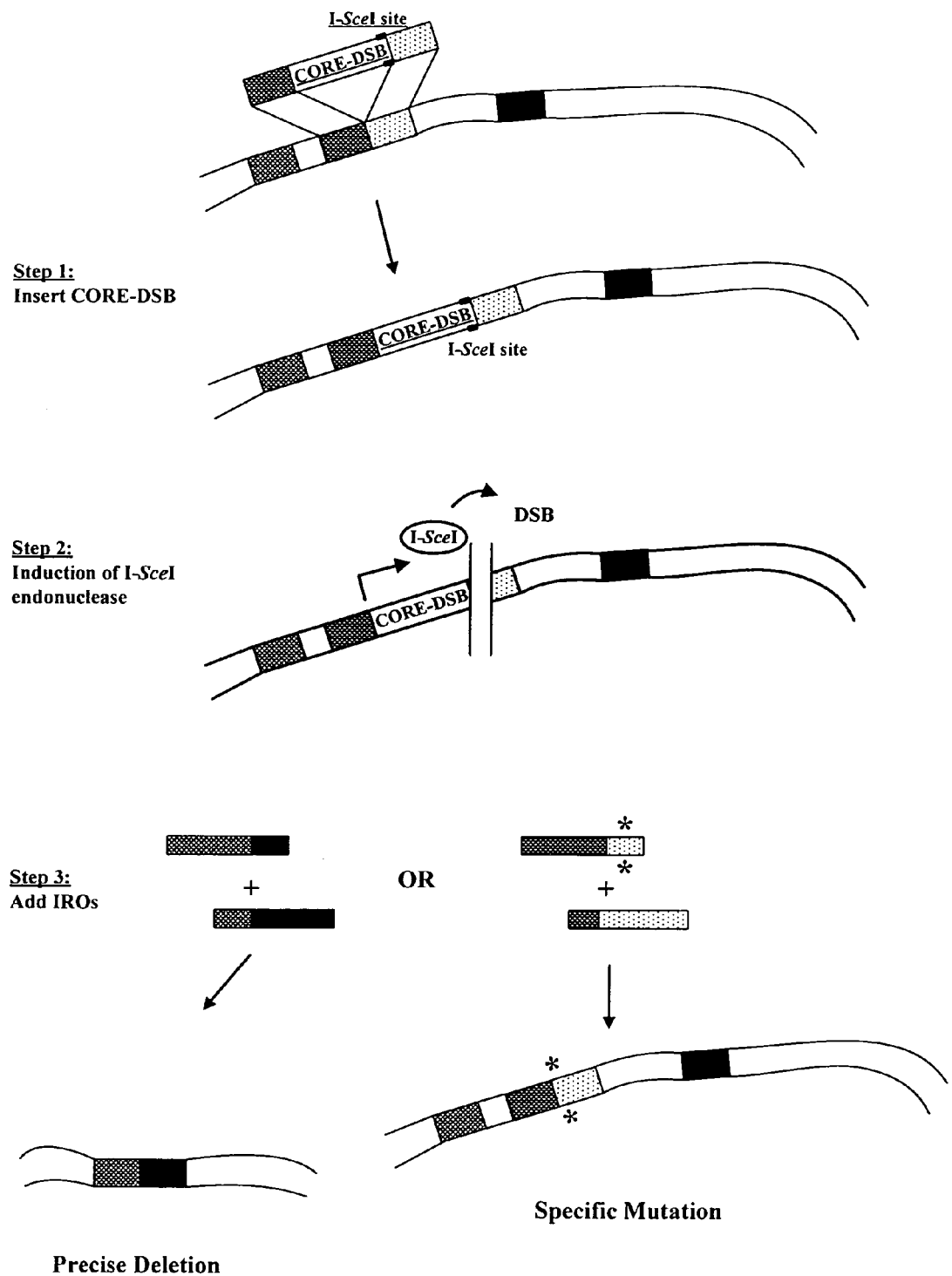

FIG. 7 illustrates an embodiment of the delitto perfetto-DSB system, which utilizes integrative recombinant oligonucleotides (IROs) to generate mutations.

The DSB-CORE cassette contains the COunterselectable and REporter genes plus the I-SceI endonuclease under the control of an inducible promoter, such as the illustrated GAL1/10 promoter. Expression of I-SceI leads to a double-strand break (DSB) at the unique target site, also contained in the cassette.

Step 1: A DSB-CORE cassette is inserted by standard DNA targeting procedures at a desired site. The insertion site is anywhere in the sequence which has been chosen to be deleted or is close to a site where a specific mutation, or multiple mutations, is to be created. The DSB-CORE cassette contains the following:
  i) Gal1/10 promoter fused to I-SceI open reading frame (GAL1/10::I-SceI). The I-SceI creates a DSB at a cut site included on the cassette. Any inducible (ie., on/off) promoter can be used and any DSB site-specific cutting enzyme can be included in the DSB-CORE cassette, provided that the only DNA site that is cut in the cell is located in the cassette.
  ii) I-SceI cut site (or other unique cut site that is the target of a DSB site-specific cutting enzyme) located at one end of the cassette or internally.
  iii) COunterselectable REporter genes (i.e., the counterselectable gene Kl-URA3+ the kanMX4 reporter gene).

Step 2: Immediately prior to transformation with IRO(s), cells are grown in the presence of galactose, which induces I-SceI endonuclease expression. The enzyme targets its single site in the cassette and generates a DSB.

Step 3: Transformation of cells with IROs leads to loss of the cassette, creation of the desired mutation(s), or deletion of the desired region. Oligonucleotide targeting in the vicinity of the DSB (delitto perfetto-DSB method) is increased up to 1000-fold, compared to oligo-mediated changes without the DSB (delitto perfetto method).

Figure 8:
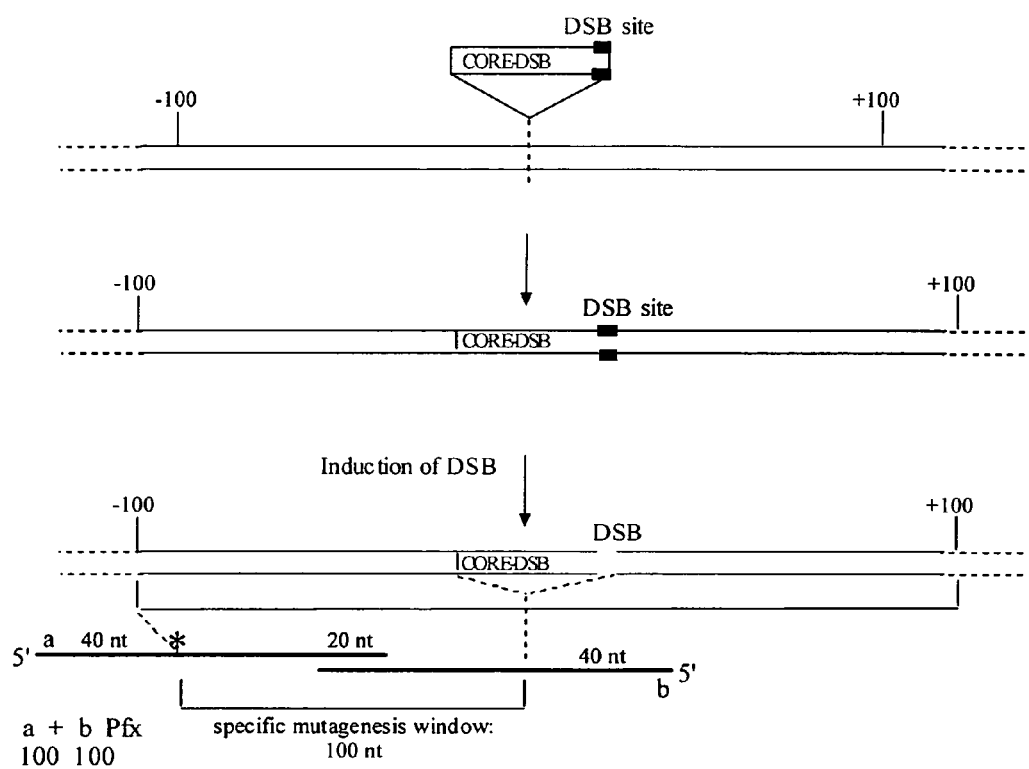

FIG. 8 shows schematic representations of the embodiment of the delitto perfetto-DSB mutagenesis strategy, illustrating some of the versatility of the technique for rapidly producing a variety of mutations.

The drawing shows an example of oligonucleotides designed to introduce a mutation (*) 100 bp upstream of the CORE-DSB integration point with IROs m+n Pfx. RE-DSB can be used in place of CORE-DSB. The efficiency of mutagenesis by IROs replacing CORE-DSB or RE-DSB after DSB induction is up to 1000 fold higher than when there is no DSB (i e., when just the CORE cassette is used).

FIG. 9 illustrates an example strategy for in vivo site-specific targeting of mutations across the DNA binding domain of p53 using the CORE-DSB. RE-DSB can be used in place of CORE-DSB. Since the efficiency of IROs targeting using the delitto perfetto-DSB approach is very efficient, the CORE-DSB or RE-DSB cassettes can be placed at longer intervals: up to 200 bp from one another.

Five isogenic strains are created each with a CORE-DSB or RE-DSB cassette integrated at a different position within the DNA binding domain of p53; the construction of strain 1 (FIG. 9A), strain 2 (FIG. 9B), and strain 4 (FIG. 9C) is shown.

Figure 9A:
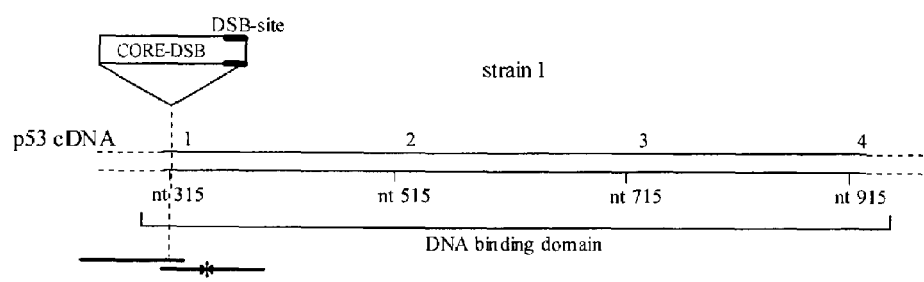
Figure 9B:
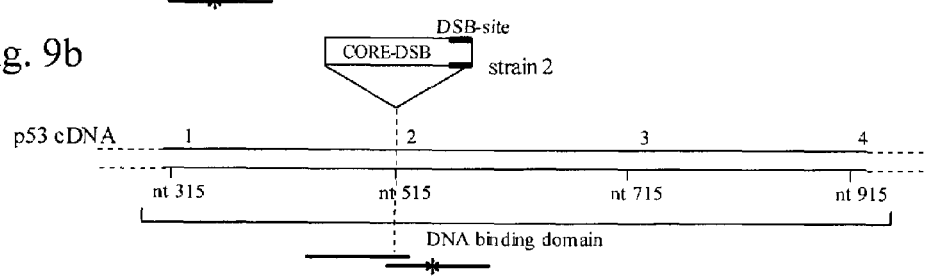
Figure 9C:
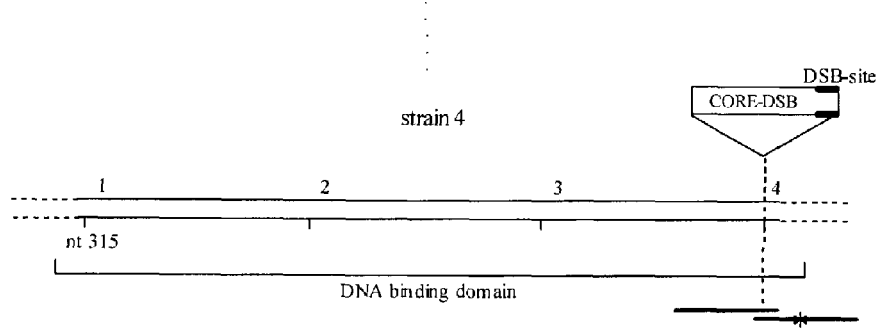

The p53 mutations can be created simply by designing oligonucleotides that contain the desired mutation. Transformation with 20 bp overlapping oligonucleotides that are homologous to a region surrounding the CORE-DSB or RE-DSB cassette results in the elimination of the cassette and creation of a site-specific change. A mutation can be designed 100 base pair upstream and downstream of each CORE-cassette insertion point. The specific illustrated embodiments show the introduction of a mutation upstream from a CORE-DSB cassette that was inserted at nucleotide 315 (strain 1; FIG. 9A), nucleotide 515 (strain 2; FIG. 9B) or nucleotide 915 (strain 4; FIG. 9C).

BRIEF DESCRIPTION OF THE SEQUENCE LISTING

The nucleic and amino acid sequences listed in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. In the accompanying sequence listing:

SEQ ID NOs: 1 and 2 are the sequences used for amplification of the CORE cassette (the kanMX4 side and the KlURA3 side, respectively) in Example 1.

SEQ ID NOs: 3-12 are oligonucleotide primers used in initial insertion of the CORE cassette into genes MLP2, POL30, TRP5 and SIR2. In the text, these sequences are referred to as MLP2.G (SEQ ID NO: 3); MLP2.U (SEQ ID NO: 4); PCNA.G (SEQ ID NO: 5); PCNA.U (SEQ ID NO: 6); TRP5.G (SEQ ID NO: 7); TRP5.U (SEQ ID NO: 8); SIR2.G1 (SEQ ID NO: 9); SIR2.U1 (SEQ ID NO: 10); SIR2.G2 (SEQ ID NO: 11); and SIR2.U2 (SEQ ID NO: 12).

SEQ ID NO: 13 is a K2 internal primer in the CORE cassette, within kanMX4.

SEQ ID NO: 14 is an URA3.2 internal primer in the CORE cassette, within KlURA3.

SEQ ID NOs: 15-26 are primers used to verify CORE insertion. In the text, these sequences are referred to as MLP2.1 (SEQ ID NO: 15); MLP2.2 (SEQ ID NO: 16); MLP2.3 (SEQ ID NO: 17); MLP2.4 (SEQ ID NO: 18); PCNA.3 (SEQ ID NO: 19); PCNA.4 (SEQ ID NO: 20); TRP5.1 (SEQ ID NO: 21); TRP5.2 (SEQ ID NO: 22); SIR2.1 (SEQ ID NO: 23); SIR2.2 (SEQ ID NO: 24); SIR2.3 (SEQ ID NO: 25); and SIR2.4 (SEQ ID NO: 26).

SEQ ID NOs: 27-50 are IROs used to make the specific changes described in the examples. In the text, these sequences are referred to as MLP2.a (SEQ ID NO: 27); MLP2.b (SEQ ID NO: 28); PCNA.a (SEQ ID NO: 29); PCNA.b (SEQ ID NO: 30); TRP5.a (SEQ ID NO: 31); TRP5.b (SEQ ID NO: 32); TRP5.c (SEQ ID NO: 33); TRP5.d (SEQ ID NO: 34); TRP5.e (SEQ ID NO: 35); TRP5.f (SEQ ID NO: 36); TRP5.e1 (SEQ ID NO: 37); TRP5.f1 (SEQ ID NO: 38); TRP5.e2 (SEQ ID NO: 39); TRP5.f2 (SEQ ID NO: 40); TRP5.i (SEQ ID NO: 41); TRP5.j (SEQ ID NO: 42); 270a (SEQ ID NO: 43); 270b (SEQ ID NO: 44); 270e (SEQ ID NO: 45); 270f (SEQ ID NO: 46); 345a (SEQ ID NO: 47); 345b (SEQ ID NO: 48); 364a (SEQ ID NO: 49); and 364b (SEQ ID NO: 50).

SEQ ID NOs: 51-54 are oligonucleotide primers used to verify deletion of RAD52: RAD52.1/LEU2.2 and RAD52.4/LEU2.1. In the text, these sequences are referred to as RAD52.1 (SEQ ID NO: 51); RAD52.4 (SEQ ID NO: 52); LEU2.1 (SEQ ID NO: 53); and LEU2.2 (SEQ ID NO: 54).

SEQ ID NOs: 55-58 are oligonucleotides (IROs) used to create large chromosomal deletion (up to 16 kb) around the TRP5 locus on chromosome VII. In the text, these sequences are referred to as 1Stu.a (SEQ ID NO: 55); 1Stu.b (SEQ ID NO: 56); 2Stu.a (SEQ ID NO: 57); and 2Stu.b (SEQ ID NO: 58).

SEQ ID NOs: 59 and 60 are oligonucleotides that were used to check the large deletions. In the text, these sequences are referred to as CGR1.1 (SEQ ID NO: 59) and STT3.1 (SEQ ID NO: 60).

SEQ ID NOs: 61 and 62 are primers that were used to perform insertion of CORE cassettes into target genes. In the text, these sequences are referred to as TRP5.I (SEQ ID NO: 61) and TRP5.II (SEQ ID NO: 62).

SEQ ID NOs: 63 and 64 are primers used for PCR amplification of the I-SceI gene under the GAL1/10 promoter; both primers contain a Bg/II site at the 5' end to enable cloning of the PCR product upstream of the CORE cassettes.

SEQ ID NOs: 65-68 are oligonucleotide primers used for insertion of CORE-DSB cassettes into the TRP5 gene. In the text, these sequences are referred to as TRP5.SceII (SEQ ID NO: 65); TSce.IU (SEQ ID NO: 66); TecS.IU (SEQ ID NO: 67); and TScecS.II (SEQ ID NO: 68).

SEQ ID NO: 69 is the GAL1/10 sequence inserted upstream from the I-SceI gene in specific embodiments.

SEQ ID NOs: 70-73 are primers used for initial insertion of the short CORE-DSB cassette into the TRP5 gene. In the text, these sequences are referred to as TRP5.IK (SEQ ID NO: 70); TSce.IK (SEQ ID NO: 71); TecS.IK (SEQ ID NO: 72); and TScecS.II (SEQ ID NO: 73).

SEQ ID NOs: 74-77 are internal primers in the CORE-UK and/or CORE-UH and/or CORE-Kp53 and/or CORE-Hp53 cassettes. In the text, these sequences are referred to as K1 (SEQ ID NO: 74); URA3.1 (SEQ ID NO: 75); H1 (SEQ ID NO: 76); and p7 (SEQ ID NO: 77).

SEQ ID NO: 78 is an internal primer in the CORE-DSB cassettes, within I-SceI.

SEQ ID NO: 79 is an internal primer in the RE-DSB cassettes, within HygroR.

SEQ ID NOs: 80-83 are primers that were used to delete the CORE-DSB insertion at the TRP5 locus and generate the desired change. In the text, these sequences are referred to as TRP5.e3 (SEQ ID NO: 80); TRP5.f3 (SEQ ID NO: 81); TRP5.e4 (SEQ ID NO: 82); and TRP5.f4 (SEQ ID NO: 83).

DETAILED DESCRIPTION

I. Abbreviations
  5-FOA: 5-fluoroorotic acid
  CORE: cassette containing a COunterselectable marker and a REporter gene
  CORE-DSB: CORE cassette additionally containing a unique DSB cut site and a sequence encoding an endonuclease that can cut at the DSB cut site.
  RE-DSB: CORE-DSB lacking the COunterselectable marker.
  DNA: deoxyribonucleic acid
  DSB: double strand break
  G418$^R$: geneticin resistance marker gene
  GAL: galactose
  HygroR: hygromicin resistance marker gene
  IROs: integrative recombinant oligonucleotides
  I-SceI: *Saccharornyces cerevisiae* mitochondrial intron-encoded endonuclease gene
  PCR: polymerase chain reaction
  ORF: open reading frame
  YAC: yeast artificial chromosome II. Terms
Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, and/or a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a biomolecule that mimics the activity of another biologically active molecule. Biologically active molecules can include both chemical structures (for instance peptides or protein entities) that mimic the biological activities of given compounds.

Animal: Living multi-cellular vertebrate organisms, a category that includes, for example, mammals (e.g., primates) and birds as well as single cellular and microscopic animals (e.g., nematodes). The term mammal includes both human and non-human mammals. Similarly, the term "subject" includes both human and veterinary subjects.

Antisense, sense, and antigene: Double-stranded DNA (dsDNA) has two strands, a 5'->3' strand (plus strand) and a 3'->5' strand (minus strand). Because RNA polymerase adds nucleic acids in a 5'->3' direction, the minus strand of the DNA serves as the template for the RNA during transcription. Thus, the RNA formed will have a sequence complementary to the minus strand and identical to the plus strand (except that the base uracil is substituted for thymine).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target.

Binding/stable binding: An oligonucleotide binds or stably binds to a target nucleic acid if a sufficient amount of the oligonucleotide forms base pairs or is hybridized to its target nucleic acid, to permit detection of that binding. Binding can be detected by physical or functional properties of the target:oligonucleotide complex. Binding between a target and an oligonucleotide can be detected by any method known to one skilled in the art, including functional and physical binding assays. Binding can be detected functionally by determining whether binding has an observable effect upon a biosynthetic process such as expression of a gene, DNA replication, transcription, and translation.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, a method that is widely used, because it is simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target dissociate from each other or "melt."

The binding between an oligomer and its target nucleic acid is frequently characterized by the temperature ($T_m$) at which 50% of the oligomer is melted from its target. A higher $T_m$ means a stronger or more stable complex relative to a complex with a lower $T_m$.

Cassette: A nucleic acid sequence encoding at least one selectable marker that can be inserted into the genome of a cell or into a plasmid, for instance a prokaryotic or eukaryotic cell. In one embodiment, the cassette includes a reporter gene such a nucleic acid sequence that confers resistance to an antibiotic in a host cell in which the nucleic acid is translated. Examples of antibiotic resistance genes include, but are not limited to, genes that provide resistance to: kanamycin, ampicillin, tetracycline, chloramphenicol, neomycin, hygromycin, and zeocin.

The most commonly used yeast genetic markers include URA3, LYS2, TRP1, LEU2, HIS3, ADE2, and $G418^R$. Less frequently used yeast genetic markers include $CYH2^S$ and $CAN1^S$ (determining sensitivity to cycloheximide and canavanine, respectively); KlURA3 (from *Kluyveromyces lactis* and homologous to *S. cerevisiae* URA3, both of which determine resistance to 5-FOA); hygromicin$^R$ (determining resistance to hygromicin); and NAT$^R$ (Nourseothricin) (determining resistance to nourseothricin).

Counterselectable markers (markers for which there is a system where loss of the marker can be selected for) in yeast include URA3, KlURA3, CYH2, CAN1, TRP1, and LYS2. In certain embodiments, counterselectable markers URA3 and KlURA3 are particularly beneficial because the majority of yeast strains have a mutation in the URA3 gene (ura⁻ strains), and the frequency of spontaneous reversions is low. KlURA3 is preferred to URA3 because it can substitute URA3 of *S. cerevisiae*, but it is at the same time divergent enough to reduce the possibility of gene conversion with the chromosomal mutated copy of URA3 in ura⁻ strains.

Other counterselectable markers are toxic gene products that, when expressed or overexpressed prevent growth and/or kill the host cell. Included in this class of counterselectable markers are restriction enzymes such as EcoRI (Lewis et al., *Mol. Cell. Biol.* 18: 1891-1902, 1998) and PvuII, and the gene that encodes p53 and toxic versions of the p53 gene (Inga and Resnick, *Oncogene* 20: 3409-3419, 2001) from humans and other mammals. These counterselectable genes are generally used under a highly regulatable promoter (that provides a low basal level and a high inducible level). In some embodiments, the expressed PvuII gene may have modifications either in the coding sequence or in a GAL1 or other inducible promoter used to drive expression of the gene. These are each examples of markers that can provide counterselection in a broad range of biological systems for which more conventional counterselectable markers may not be available or are inconvenient. These counterselectable markers are thus considered "universal" or "generic," in that they are not dependent (or are only indirectly or minimally dependent) on the species or genetic background of the host cell.

The following markers are also considered heterologous markers in yeast, since the involved genetic sequence is not native to *S. cerevisiae* but has been added from a different species: KlURA3, $G418^R$, hygromicin$^R$, NAT$^R$, and p53.

A specific example of a cassette is a CORE-cassette, which contains both a COunterselectable marker and a REporter gene. Other specific examples include RE-cassettes (having a reporter gene but no counter selectable marker), CORE-DSB-cassettes (having a counterselectable marker, a reporter gene, a double-strand break site, and a sequence encoding a double-strand break enzyme having specific activity for that site), and RE-DSB-cassettes (similar to CORE-DSB-cassettes, but lacking a counterselectable marker). Also contemplated are cassettes for use in delitto perfetto-DSB mutagenesis, wherein the function of the double-strand break enzyme is not encoded by the cassette itself, but is instead added exogenously to the cells, usually after insertion of the cassette and prior to (or concurrent with) transformation with IRO(s).

cDNA (complementary DNA): A piece of DNA lacking internal, non-coding segments (introns) and regulatory sequences which determine transcription. cDNA may be synthesized in the laboratory by reverse transcription from messenger RNA extracted from cells.

Deletion: The removal of a sequence of DNA, the regions on either side of the removed sequence being joined together. Correspondingly, a deletion in a protein is the removal of a region of amino acid sequence of the protein or peptide. Deletions can be quite short, for instance only one or a few nucleic acids to 10, 15, 20, 25, 30, 50, 80, or 100 nucleic acids or longer, and may be quite long. In particular embodiments long deletions may be at least 500 nucleic acids, at least 750, at least 1000, at least 2500, at least 3000, at least 5000, at least 8000, at least 10,000, or more nucleic acids in length. Particularly long deletions may be over 10,000 nucleic acids, for instance as long as 15,000, 20,000, 30,000, or more.

DNA (deoxyribonucleic acid): DNA is a long chain polymer that comprises the genetic material of most living organisms (some viruses have genes comprising ribonucleic acid, RNA). The repeating units in DNA polymers are four different nucleotides, each of which comprises one of the four bases, adenine, guanine, cytosine, and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule.

Double strand break: Breaks that occur in the DNA backbones of both strands at approximately the same nucleotide pair are called double-strand breaks.

Endonuclease: An enzyme that breaks the internal phosphodiester bonds in a DNA molecule.

Heterologous: A sequence that is not normally (i.e., in the wild-type sequence) found adjacent to a second sequence. In one embodiment, the sequence is from a different genetic source, such as a virus or other organism, than the second sequence.

Homing endonucleases: Site-specific endonucleases encoded by intron or intein to promote homing of a genetic element into the intronless or inteinless allele. They are double stranded DNAses that have large, asymmetric recognition site (12-40 base pairs) and coding sequences that are usually embedded in their introns or inteins. Introns are spliced out of precursor RNAs, while inteins are spliced out of precursor proteins. Homing endonucleases are named using conventions similar to those of restriction endonucleases, with intron encoding endonucleases containing the prefix, "I-" and intein endonucleases containing the prefix, "PI-".

Homing endonuclease recognition sites are extremely rare. For example, an 18 base pair recognition will occur only once in every 7×10$^{10}$ base pairs of random sequence. This is equivalent to only one site in 20 mammalian-sized genomes. However, unlike standard restriction endonucleases, homing endonucleases tolerate some sequence degeneracy within their recognition sequence. As a result, their observed sequence specificity is typically in the range of 10-12 base pairs. Homing endonucleases do not have stringently-defined recognition sequences in the way that restriction enzymes do. That is, single base changes do not abolish cleavage but reduce its efficiency to variable extents. The precise boundary of required basis is generally not known.

The homing enzymes that initiate the mobility process can be grouped into families, which share structural and functional properties with each other and with some freestanding, intergenic endonucleases. Several endonucleases encoded by introns and inteins in the three biological kingdoms have been shown to promote the homing of their respective genetic elements into allelic intronless and inteinless sites (Belfort & Roberts, *Nucleic Acids Research*, 25: 3379-3388, 1997). Examples of homing endonuclease: I-CreI, I-PpoI, I-SceI, I-CeuI, PI-PspI, PI-SceI. Among homing endonucleases there is also VDE of *Saccharomyces*.

Hybridization: Poly- and oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the poly- or oligonucleotide (or its analog) and the DNA or RNA target. The poly- or oligonucleotide (or its analog) need not be 100% complementary to its target sequence to be specifically hybridizable. A nucleotide molecule or analog thereof is specifically hybridizable when its binding to a target DNA or RNA molecule occurs with a sufficient degree of complementarity to avoid non-specific binding of the nucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending on the nature of the hybridization method of choice and the composition and length of the hybridizing nucleic acid sequences. Generally, the temperature of hybridization and the ionic strength (especially the Na$^+$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11, incorporated herein by reference.

By way of illustration, hybridization is generally carried out in vitro in a solution of high ionic strength such as 6×SSC at a temperature that is 20-25° C. below the melting temperature, $T_m$, described below. For instance, for Southern hybridization experiments where the target DNA molecule on the Southern blot contains 10 ng of DNA or more, hybridization is typically carried out for 6-8 hours using 1-2 ng/ml radiolabeled poly- or oligonucleotide probe (of specific activity equal to 10$^9$ CPM/μg or greater, for instance). Following hybridization, the nitrocellulose filter (Southern blot) is washed to remove background hybridization. The washing conditions should be as stringent as possible to remove background hybridization but to retain a specific hybridization signal.

The term $T_m$ represents the temperature above which, under the prevailing ionic conditions, the probe nucleic acid molecule will not hybridize to its target DNA molecule. The $T_m$ of such a hybrid molecule may be estimated from the following equation:

$$T_m = 81.5° C. - 16.6(\log_{10}[Na^-]) + 0.41(\% \ G+C) - 0.63(\% \ \text{formamide}) - (600/l)$$

Where l=the length of the hybrid in base pairs.

This equation is valid for concentrations of Na$^+$ in the range of 0.01 M to 0.4 M, and it is less accurate for calculations of $T_m$ in solutions of higher [Na$^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al., 1989). Thus, by way of example, for a 150 base pair DNA probe with a hypothetical GC content of 45%, a calculation of hybridization conditions required to give particular stringencies may be made as follows:

For this example, it is assumed that the filter will be washed in 0.3×SSC solution following hybridization, thereby

[Na$^+$]=0.045M
% GC=45%
Formamide concentration=0
l=150 base pairs $$T_m = 81.5 - 16(\log_{10}[Na^+]) + (0.41 \times 45) - (600/150)$$

and so $T_m$=74.4° C.

The $T_m$ of double-stranded DNA decreases by 1-1.5° C. with every 1% decrease in homology (Bonner et al., *J. Mol. Biol.* 81:123-135, 1973). Therefore, for this given example, washing the filter in 0.3×SSC at 59.4-64.4° C. will produce a stringency of hybridization equivalent to 90%; that is, DNA molecules with more than 10% sequence variation relative to the target cDNA will not hybridize. Alternatively, washing the hybridized filter in 0.3×SSC at a temperature of 65.4-68.4° C. will yield a hybridization stringency of 94%; that is, DNA molecules with more than 6% sequence variation relative to the target cDNA molecule will not hybridize. The above examples are given entirely by way of theoretical illustration. One skilled in the art will appreciate that other hybridization techniques may be utilized and that variations in experimental conditions will necessitate alternative calculations for stringency.

For purposes of the present invention, "stringent conditions" encompass conditions under which hybridization will only occur if there is less than 25% mismatch between the hybridization probe and the target sequence. "Stringent conditions" may be broken down into particular levels of stringency for more precise distinction. Thus, as used herein, "moderately stringent" conditions are those under which DNA molecules with more than 25% sequence variation (also termed "mismatch") will not hybridize; "medium stringent" conditions are those under which DNA molecules with more than 15% mismatch will not hybridize, and "highly stringent" conditions are those under which DNA sequences with more than 10% mismatch will not hybridize. "Very highly stringent" conditions are those under which DNA sequences with more than 6% mismatch will not hybridize.

In vitro amplification: Techniques that increase the number of copies of a nucleic acid molecule in a sample or specimen. An example of in vitro amplification is the polymerase chain reaction (PCR), in which a nucleic acid molecule (such as one contained in a biological sample collected from a subject) is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid.

The product of in vitro amplification may be characterized by electrophoresis, restriction endonuclease cleavage patterns, oligonucleotide hybridization or ligation, and/or nucleic acid sequencing, using standard techniques.

Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Inducer: A small molecule that triggers gene transcription by binding to a regulator protein.

Inducible promoter: A promoter system that can be used to regulate the amount and the timing of protein expression. Unlike constitutive promoters, an inducible promoter is not always active. Some inducible promoters are activated by physical stimuli, such as the heat shock promoter. Others are activated by chemical stimuli, such as IPTG or Tetracycline (Tet), or galactose. Inducible promoters or gene-switches are used to both spatially and temporally regulate gene expression By allowing the time and/or location of gene expression to be precisely regulated, gene-switches or inducible promoters may control deleterious and/or abnormal effects caused by overexpression or non-localized gene expression. Thus, for a typical inducible promoter in the absence of the inducer, there would be little or no gene expression while, in the presence of the inducer, expression should be high (i.e., off/on). A number of controllable gene expression systems have been devised, including those regulated by heat (Ainley and Key, *Plant Mol. Biol.*, 14:949-967, 1990; Holtorf et al., *Plant Mol. Biol.* 29:637-646, 1995), pathogens (PR1-a; Williams et al., *Biotechnology* 10:540-543, 1992; Gatz, *Annu. Rev. Plant Physiol. Plant Mol. Biol.* 48:89-108, 1997), herbicide safeners (In2-2, GST-27; De Veylder et al., *Plant Cell Physiol.* 38:568-577, 1997), light (Kuhlemeier et al., *Plant Cell* 1:471-478, 1989), wounding (Firek et al., *Plant Mol. Biol.* 22:129-212, 1993), ethanol (Salter et al., *Plant J.* 16:127-132, 1998), phytohormones (Li et al., *Plant Cell* 3:1167-1175, 1991), steroids (Aoyama and Chua, *Plant J.*, 11:605-612, 1997), and tetracycline (Gatz et al., *Plant J.* 2:397-404, 1992; Weinmann et al., *Plant J.*, 5:559-569, 1994; Sommer et al., *Plant Cell Rep.* 17:891-896, 1998) (from Granger & Cyr, *Plant Cell Reports* 20:227-234, 2001).

The following are examples of specific types of inducible promoters and examples of their use:

Steroid inducible expression: Keith Yamamoto's lab developed an inducible system in yeast similar to the ecdysone system we talked about for mammalian cells. They placed the rat glucocorticoid receptor gene behind the constitutive GPD promoter to express the rat glucocorticoid receptor in yeast. A second vector was made with three glucocorticoid response elements upstream of the CYC1 gene minimal promoter (cytochrome c gene). A cloning site was placed after this so a selected gene could be placed under control of the 3GRE/CYC1 promoter. Both vectors were high copy vectors. This system works well with dose dependent expression when steroid hormone is added to the medium. Response time is rapid with $t_{1/2}$ of 7-9 minutes after addition of hormone.

Copper inducible expression: The CUP1 promoter can be used to make a gene inducible by copper or silver ions. By way of example, a gene, when placed under CUP1 regulation, should e provided with a degree of control of the level of expression based on the amount of copper in the medium. Copper is toxic and any strain should be tested to see how well it tolerates copper before making a CUP1 construct.

Heat shock expression: By placing the UAS from a heat shock gene in front of the minimal CYC1 promoter, you can place YFG (your favorite gene) under heat shock induction. This is a specialized requirement usually used in studies of heat shock response GAL1-10 promoter: This promoter is highly regulatable by galactose, such that there is a basal level on glucose, but over 100 fold increase when cells are placed in galactose medium.

The yeast GAL genes form one of the most intensely studied model systems for eukaryotic gene regulation. The structural genes, e.g. GAL1 and GAL10, are induced to very high level expression in galactose by the action of the activator Gal4p. Gal4p binds to activation sequences (UASG) that lie up stream of GAL genes and activates transcription in a process that depends on gene-proximal TATA elements and involves numerous coactivators and general transcription factors including TBP. The activation function of Gal4p is modulated by Gal80p, an inhibitory regulator that binds specifically to the activation domain of Gal4p, thus preventing gene activation in nongalactose carbon sources.

Induction: The ability of a bacteria (or yeast, or other organism) to synthesize certain enzymes only when their substrates are present; applied to gene expression refers to switching on transcription as a result of interaction of the inducer with the regulator protein.

Isolated: An isolated biological component (such as a nucleic acid, peptide or protein) has been substantially separated, produced apart from, or purified away from other biological components in the cell of the organism in which the component naturally occurs, i.e., other chromosomal and extra-chromosomal DNA and RNA, and proteins. Nucleic acids, peptides, and proteins that have been isolated include nucleic acids and proteins purified by standard purification methods. The term also embraces nucleic acids, peptides and proteins prepared by recombinant expression in a host cell as well as chemically synthesized nucleic acids.

Nucleic acid: A sequence composed of nucleotides, including the nucleotides that are found in DNA and RNA.

Nucleotide: This term includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A linear polynucleotide sequence usually of up to about 200 nucleotide bases in length, for example a polynucleotide (such as DNA or RNA) which is at least six nucleotides, for example at least 15, 20, 50, 100 or even 200 nucleotides long. In certain embodiments, it is envisioned that oligonucleotides may be over 200 nucleotides in length, for instance, 220, 250, 270, 290, 300, 350, 400 or more nucleotides.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids. These sequences are usually translatable into a peptide.

Ortholog: Two nucleotide sequences are orthologs of each other if they share a common ancestral sequence, and diverged when a species carrying that ancestral sequence split into two species. Orthologous sequences are also homologous sequences.

Polynucleotide: A linear nucleic acid sequence of any length. Therefore, a polynucleotide includes molecules which are at least 15, 20, 50, 100, 200, 250, 300, 400 (e.g., oligonucleotides)or more, and also including nucleotides as long as a full length cDNAs, genes, or chromosomes.

Peptide Nucleic Acid (PNA): An oligonucleotide analog with a backbone comprised of monomers coupled by amide (peptide) bonds, such as amino acid monomers joined by peptide bonds.

Probes and primers: A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al., *Molecular Cloning: A Laboratory Manual,* Cold Spring Harbor Laboratory Press (1989); and Ausubel et al., *Current Protocols in Molecular Biology,* Greene Publishing Associates and Wiley-Intersciences (1987).

Primers are short nucleic acids, for example DNA oligonucleotides at least 6 nucleotides in length, and/or no longer than 10, 20, 50, 100 or 200 nucleotides in length, though in some embodiments they are longer. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by PCR or other nucleic acid amplification methods known in the art.

Methods for preparing and using probes and primers are described, for example, in Sambrook et al. (*Molecular Cloning: A Laboratory Manual,* Cold Spring Harbor Laboratory Press, 1989), Ausubel et al., *Current Protocols in Molecular Biology,* Greene Publishing Associates and Wiley-Intersciences (1987), and Innis et al., *PCR Protocols, A Guide to Methods and Applications,* 1990, Innis et al. (eds.), 21-27, Academic Press, Inc., San Diego, Calif. PCR primer pairs can be derived from a known sequence, for example, by using computer programs intended for that purpose, such as Primer (Version 0.5, © 1991, Whitehead Institute for Biomedical Research, Cambridge, Mass.).

Probes and primers disclosed herein comprise at least 10 nucleotides of a nucleic acid sequence, although a shorter nucleic acid may be used as a probe or primer if it specifically hybridizes under stringent conditions with a target nucleic acid by methods well known in the art. The disclosure thus includes isolated nucleic acid molecules that include specified lengths of the disclosed sequences. One of skill in the art will appreciate that the specificity of a particular probe or primer increases with its length. Thus, for example, a primer comprising 20 consecutive nucleotides of a sequence will anneal to a target sequence (for instance, contained within a genomic DNA library) with a higher specificity than a corresponding primer of only 15 nucleotides. To enhance specificity, longer probes and primers can be used, for example probes and primers that comprise at least 20, 30, 40, 50, 60, 70, 80, 90, 100 or more consecutive nucleotides from any region of a target.

When referring to a probe or primer, the term "specific for (a target sequence)" indicates that the probe or primer hybridizes under stringent conditions substantially only to the target sequence in a given sample comprising the target sequence.

Promoter: An array of nucleic acid control sequences which direct transcription of a nucleic acid. A promoter includes necessary nucleic acid sequences near the start site of transcription, such as, in the case of a polymerase 11 type promoter, a TATA element. In one embodiment, a promoter includes an enhancer. In another embodiment, a promoter includes a repressor element. In these embodiments, a chimeric promoter is created (a promoter/enhancer chimera or a promoter/repressor chimera, respectively). Enhancer and repressor elements can be located adjacent to, or distal to the promoter, and can be located as much as several thousand base pairs from the start site of transcription. Examples of promoters that can be used in the present disclosure include, but are not limited to the SV40 promoter, the CMV enhancer-promoter, the CMV enhancer/β-actin promoter, and the tissue-specific promoter probasin.

Other promoter sequences which can be used to construct the nucleic acids and practice the methods disclosed herein include, but are not limited to: the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors, any retroviral LTR promoter such as the RSV promoter; inducible promoters, such as the MMTV promoter; the metallothionein promoter; heat shock promoters; the albumin promoter; the histone promoter; the α-actin promoter; TK promoters; B19 parvovirus promoters; the SV10 late promoter; the ApoAI promoter and combinations thereof.

In one embodiment, a promoter is a strong promoter, which promotes transcription of RNA at high levels, for example at levels such that the transcriptional activity of the promoter generally accounts for about 25% of transcriptional activity of all transcription within a cell. The strength of a promoter is often tissue-specific and thus may vary from one cell type to another. For example, CMV is a classic strong promoter because it generates high levels of transcriptional activity in many cell types. Examples of strong promoters include, but are not limited to: CMV; CMV/chicken β-actin; elongation factors 1A and 2A; SV40; RSV; and the MoLV LTR.

In another embodiment, a promoter is a tissue-specific promoter, which promotes transcription in a single cell type or narrow range of tissues. Examples of tissue-specific promoters include, but are not limited to: probasin (which promotes expression in prostate cells), an immunoglobulin promoter; a whey acidic protein promoter; a casein promoter; glial fibrillary acidic protein promoter; albumin promoter; β-globin promoter; and the MMTV promoter.

In yet another embodiment, a promoter is a hormone-responsive promoter, which promotes transcription only when exposed to a hormone. Examples of hormone-responsive promoters include, but are not limited to: probasin (which is responsive to testosterone and other androgens); MMTV promoter (which is responsive to dexamethazone, estrogen, and androgens); and the whey acidic protein promoter and casein promoter (which are responsive to estrogen).

For expression of yeast genes in yeast, there are a variety of promoters to choose from for various purposes. The following are provided by way of example, and are not meant to be in any way limiting:

The Gal 1,10 promoter: This promoter is inducible by galactose. It is frequently valuable to be able to turn expression of your gene on and off so you can follow the time dependent effects of expression. The Gal promoter is slightly leaky, and so is appropriate where it is not essential to have absolutely no expression of the passenger gene in the absence of galactose. The Gal 1 gene and Gal 10 gene are adjacent and transcribed in opposite directions from the same promoter region. The regulatory region containing the UAS sequences can be cut out on a DdeI Sau3A fragment and placed upstream of any other gene to confer galactose inducible expression and glucose repression.

PGK, GPD and ADH1 promoters: These are high expression constitutive promoters. PGK=phosphoglycerate kinase, GPD=glyceraldehyde 3 phosphate dehydrogenase, ADH1=alcohol dehydrogenase ADH2 promoter: This gene is glucose repressible and it is strongly transcribed on non-fermentable carbon sources (similar to GAL 1,10 except not inducible by galactose).

CUP1 promoter: This is the metalothionein gene promoter. It is activated by copper or silver ions added to the medium. The CUP1 gene is one of a few yeast genes that is present in yeast in more than one copy. Depending on the strain, there can be up to eight copies of this gene.

PHO5 promoter: This promoter is derived from a gene that encodes an acid phosphatase. It is induced by low or no phosphate in the medium. The phosphatase is secreted in the chance it will be able to free up some phosphate from the surroundings. When phosphate is present, no PHO5 message can be found. When it is absent it is turned on strongly.

Protein: A biological molecule expressed by a gene and comprised of amino acids.

Purified: The term purified does not require absolute purity; rather, it is intended as a relative term. Thus, for example, a purified protein (or nucleic acid) preparation is one in which the protein (or nucleic acid) is more pure than the molecule in its natural environment within a cell (or other production vessel). In one embodiment, a preparation of a molecule is purified such that the molecule represents at least 50%, for example at least 70%, of the total content of the preparation.

Random oligonucleotide: An oligonucleotide with a random sequence (see, for instance, U.S. Pat. Nos. 5,043,272 and 5,106,727, which illustrate random oligonucleotides used for priming in vitro amplification reactions) in at least one position within the length of the oligonucleotide.

The sequences of random oligonucleotides may not be random in the absolute mathematic sense. For instance, chemically synthesized random oligonucleotide will be random to the extent that physical and chemical efficiencies of the synthetic procedure will allow, and based on the method of synthesis. Oligonucleotides having defined sequences may satisfy the definition of random if the conditions of their use cause the locations of their apposition to the template to be indeterminate. Also, random oligonucleotides may be "random" only over a portion of their length, in that one residue within the sequence, or a portion of the sequence, can be identified and defined prior to synthesis of the primer.

Random oligonucleotides may be generated using available oligonucleotide synthesis procedures; randomness of the sequence may be introduced by providing a mixture of nucleic acid residues in the reaction mixture at one or more addition steps (to produce a mixture of oligonucleotides with random sequence at that residue position). Thus, an oligonucleotide that is random throughout its length can be generated by sequentially incorporating nucleic acid residues from a mixture of 25% of each of dATP, dCTP, dGTP, and dTTP, to form an oligonucleotide. Other ratios of dNTPs can be used (e.g., more or less of any one dNTP, with the other proportions adapted so the whole amount is 100%).

The term "random oligonucleotide" specifically includes a collection of individual oligonucleotides of different sequences, for instance, which can be indicated by the generic formula 5'-XXXXX-3', wherein X represents a nucleotide residue that was added to the oligonucleotide from a mixture of a definable percentage of each dNTP. For instance, if the mixture contained 25% each of dATP, dCTP, dGTP, and dTTP, the indicated oligonucleotide would contain a mixture of oligonucleotides that have a roughly 25% average chance of having A, C, G, or T at each position.

This term also includes a mixture of oligonucleotides with the generic formula 5'-nnnXnn-31, wherein X is defined as in the first formula and n denotes a known nucleotide (e.g., A, C, G, or T).

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al. (In: *Molecular Cloning: A Laboratory Manual,* Cold Spring Harbor, N.Y., 1989).

Restriction endonucleases: Enzymes that recognize specific nucleotide sequences and cleave both strands of the DNA containing those sequences.

Sequence identity: The identity between two or more nucleic acid sequences, or two or more amino acid sequences, is expressed in terms of the identity between the sequences. Sequence identity can be measured in terms of percentage identity (or similarity or homology); the higher the percentage, the more near to identical the sequences are to each other. Homologs or orthologs of nucleic acid or amino acid sequences possess a relatively high degree of sequence identity when aligned using standard methods. This homology is more significant when orthologous proteins or cDNAs are derived from species that are more closely related (e.g. human and monkey sequences), compared to species more distantly related (e.g., human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. Biosc.* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater identity to the reference sequence will show increasing percentage identities when assessed by this method, such as at least 70%, 75%, 80%, 85%, 90%, 95%, 98%, or 99% sequence identity, when using gapped blastp with databases such as the nr, pat, or swissprot database. Queries searched with the blastp program are filtered with DUST (Hancock and Armstrong, *Comput. Appl. Biosci.* 10:67-70, 1994). Other programs use SEG.

When less than the entire sequence is being compared for sequence identity, homologs typically possess at least 75% sequence identity over short windows of 10-20 amino acids, and may possess sequence identities of at least 85%, 90%, 95% or 98% or more, depending on their identity to the reference sequence. Methods for determining sequence identity over such short windows are described at the NCBI web site.

One of skill in the art will appreciate that these sequence identity ranges are provided for guidance only; it is entirely possible that significant homologs can be obtained that fall outside of the ranges provided.

Site-specific endonuclease: An enzyme that generates a DSB at a specific site within a nucleic acid molecule. By way of example, yeast HO is an endonuclease, required for mating-type switching in yeast. The HO endonuclease cleaves the DNA sequence at MAT, the mating type locus, that determines the cell's mating type (either a or α). The DSB causes a gene conversion event to occur using either of two donor sequences, called HML and HMR, leading to the unidirectional transfer of mating type information from HML or HMR to MAT. The HO gene encodes an endonuclease that recognizes a consensus sequence of 24 bp and makes a 4 bp staggered cleavage within that sequence.

Transduced and Transfected: A virus or vector transduces or transfects a cell when it transfers nucleic acid into the cell. A cell is "transfected" by a nucleic acid transduced into the cell when the DNA becomes stably replicated by the cell, either by incorporation of the nucleic acid into the cellular genome, or by episomal replication.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" are intended to include plurals unless context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. The materials, methods, and examples are illustrative only and not intended to be limiting.

III. Overview of Several Embodiments

A first embodiment is a method for introducing a mutation into a target double stranded nucleic acid sequence in a cell, wherein the double stranded nucleic acid sequence comprises a first and a second strand, and the method involves introducing a double-stranded nucleic acid cassette into a target nucleic acid sequence at an insertion point, wherein the cassette is a RE-cassette and comprises a first portion homologous to a nucleic acid sequence on a first side of the insertion point; a second portion homologous to a second nucleic acid sequence on a second side of the insertion point; and a nucleic acid sequence encoding a reporter located between the first portion and the second portion; transforming the cell with a first oligonucleotide comprising a nucleic acid sequence homologous to one strand (the chosen strand) of the target nucleic acid sequence at a position on the first side of the insertion point; and a nucleic acid sequence homologous to the same strand of the target nucleic acid sequence at a position on the second side of the insertion point, and comprising at least one nucleotide that differs from the chosen strand of the target nucleic acid sequence; and selecting for loss of the nucleic acid sequence encoding the reporter gene, wherein loss of the nucleic acid sequence encoding the reporter gene indicates integration of the oligonucleotide sequence comprising the at least one nucleotide that differs from the target nucleic acid sequence.

A second embodiment is a method for introducing a mutation into a target double stranded nucleic acid sequence in a cell, wherein the double-stranded nucleic acid cassette further comprises a nucleic acid sequence encoding a counterselectable marker located between the first portion and the second portion, which cassette is referred to as a CORE-cassette, and wherein the method further comprises selecting for loss of both the nucleic acid encoding the counterselectable marker and the nucleic acid sequence encoding the reporter gene, wherein loss of both the nucleic acid sequence encoding the counterselectable marker and the nucleic acid sequence encoding the reporter gene indicates integration of the oligonucleotide sequence comprising the at least one nucleotide that differs from the target nucleic acid sequence. Optionally the double-stranded nucleic acid cassette in certain embodiments further comprises a nucleic acid sequence comprising a double-strand break recognition site, a nucleic acid encoding a double-strand break enzyme that recognizes the double-strand break recognition site, and an inducible promoter, operably connected with the nucleic acid encoding the double-strand break enzyme, which cassette is referred to as a CORE-DSB-cassette.

Yet another embodiment is a method for introducing a mutation into a target double stranded nucleic acid sequence in a cell, wherein the double-stranded nucleic acid cassette further comprises a nucleic acid sequence comprising a double-strand break recognition site, a nucleic acid encoding a double-strand break enzyme that recognizes the double-strand break recognition site, and an inducible promoter, operably connected with the nucleic acid encoding the double-strand break enzyme, which cassette is referred to as a RE-DSB-cassette.

In specific embodiments that include in the cassette a double-strand break site and nucleic acid sequence encoding a double-strand break enzyme, the method further comprises inducing expression of the double strand break enzyme, thereby stimulating a double-strand break within the cassette, which double-strand break stimulates recombination.

In specific examples of the provided methods, the oligonucleotide sequence comprises more than one nucleotide that differs from the target nucleic acid sequence. In certain examples, transforming the cell with the first oligonucleotide occurs prior to selecting for loss of both the nucleic acid encoding the counterselectable marker and the nucleic acid encoding the reporter gene.

Also provided are methods that further comprise transforming the cell with a second oligonucleotide (for instance, concurrently with transforming the cell with the second oligonucleotide) that is at least partially complementary to the first oligonucleotide. In specific examples, the second oligonucleotide comprises a nucleic acid sequence homologous to the target nucleic acid sequence at a position to the first side of the insertion point. In other examples, the second oligonucleotide comprises a nucleic acid sequence homologous to the target nucleic acid sequence at a position to the second side of the insertion point. In still other examples, the second oligonucleotide comprises a nucleic acid sequence homologous to the target nucleic acid sequence at a position to the first side of the insertion point; and a nucleic acid sequence homologous to the target nucleic acid sequence at a position to the second side of the insertion point.

In various embodiments, the first and/or second oligonucleotide contains at least one random nucleotide change compared to the target nucleic acid sequence, and optionally contains several. In certain embodiments, the second oligonucleotide is fully complementary to the first oligonucleotide. In other embodiments, the 3' ends of the two oligonucleotides are complementary but the first oligonucleotide lacks homology to the second side of the insertion point and the second oligonucleotide lacks homology to the first side of the insertion point. In still other embodiments, the 3' ends of the two oligonucleotides are complementary but the second oligonucleotide lacks homology to the second side of the insertion point and the first oligonucleotide lacks homology to the first side of the insertion point. In yet another embodiment, the 5' ends of the two oligonucleotides are complementary but the first oligonucleotide lacks homology to the second side of the insertion point and the second oligonucleotide lacks homology to the first side of the insertion point. Alternatively, in certain embodiments the 5' ends of the two oligonucleotides are complementary but the second oligonucleotide lacks homology to the second side of the insertion point and the first oligonucleotide lacks homology to the first side of the insertion point.

Also provided are methods using CORE-cassettes or CORE-DSB-cassettes, wherein the counterselectable marker is KlURA3, URA3, TRP5, TRP1, or a gene encoding a toxin. In specific examples of such methods, the counterselectable marker is a gene encoding a toxin, and the toxin is an inducible restriction enzyme or an inducible p53 gene. Optionally, the inducible p53 gene is a toxic version.

In some embodiments, the reporter encodes a polypeptide that confers antibiotic resistance to the cell. The antibiotic is G418, hygromycin, kanamycin, ampicillin, tetracycline, chloramphenicol, neomycin, zeocin, nourseothricin, cycloheximide or canavanine in specific examples.

Also described herein are methods wherein the reporter encodes a polypeptide from an amino acid or nucleotide synthesis pathway. The polypeptide is LEU2, TRP5, TRP1, LYS2, HIS3, or ADE2 in particular examples.

The oligonucleotide in various methods can be of any length, for instance at least 30 nucleotides, at least 40 nucleotides, at least 50 nucleotides, or at least 80 nucleotides in length.

Also described herein are methods in which the first and the second oligonucleotides are each at least 30 nucleotides in length. In other methods, the first and the second oligonucleotides are each at least 40 nucleotides in length, at least 50 nucleotides in length, or at least 80 nucleotides in length.

In certain embodiments, the first and the second oligonucleotide are of different lengths.

In certain embodiments, the region of overlap at the 3' ends of the oligonucleotides is at least 10 base pairs; in others, the region of overlap at the 3' ends is at least 15 base pairs. In specific examples of such methods, the 3' ends of the first and second oligonucleotide can be extended by in vitro polymerization.

Also provided are methods wherein at least one oligonucleotide differs from the target nucleic acid sequence by more than one nucleotide. In other examples, both oligonucleotides differ from the target nucleic acid sequence by at least a single nucleotide. In specific examples, at least one nucleotide difference is inside the region of overlap between the first and second oligonucleotides, while in other examples, at least one nucleotide difference is outside the region of overlap between the first and second oligonucleotides. In some examples, differences occur both inside and outside of the region of overlap.

Another embodiment is a method of deleting a target double stranded nucleic acid sequence (for instance, from about 1 to up to about 16,000 bp in length) from within a cell, wherein the target double stranded nucleic acid sequence comprises a first and a second strand, the method comprising introducing a double-stranded nucleic acid cassette into a target nucleic acid sequence at an insertion point, wherein the cassette is a RE-cassette and comprises a nucleic acid sequence encoding a reporter located between a first portion and a second portion of the RE-cassette; transforming the cell with a first oligonucleotide comprising a nucleic acid sequence homologous to the first strand of a nucleic acid 5' of the nucleic acid of interest; and a sequence homologous to the first strand of a nucleic acid 3' of the nucleic acid sequence of interest; and selecting for loss of the nucleic acid sequence encoding the reporter gene, wherein loss of the nucleic acid sequence encoding the reporter gene from the target double stranded nucleic acid indicates deletion of the target double stranded nucleic acid.

Yet another provided embodiment is a method of deleting a target double stranded nucleic acid sequence from within a cell, wherein the double-stranded nucleic acid cassette further comprises a nucleic acid sequence encoding a counterselectable marker located between the first portion and the second portion, which cassette is referred to as a CORE-cassette, and wherein the method further comprises selecting for loss of both the nucleic acid sequence encoding the counterselectable marker and the nucleic acid sequence encoding the reporter gene, wherein loss of both the nucleic acid sequence encoding the counterselectable marker and the nucleic acid sequence encoding the reporter gene indicates deletion of the target double stranded nucleic acid.

Another embodiment is a method of deleting a target double stranded nucleic acid sequence from within a cell, wherein the double-stranded nucleic acid cassette further comprises a nucleic acid sequence comprising a double-strand break recognition site, a nucleic acid encoding a double-strand break enzyme that recognizes the double-strand break recognition site, and an inducible promoter, operably connected with the nucleic acid encoding the double-strand break enzyme, which cassette is referred to as a RE-DSB-cassette.

In another provided method of deleting a target double stranded nucleic acid sequence from within a cell, the double-stranded nucleic acid cassette further comprises a nucleic acid sequence comprising a double-strand break recognition site, a nucleic acid encoding a double-strand break enzyme that recognizes the double-strand break recognition site, and an inducible promoter, operably connected with the nucleic acid encoding the double-strand break enzyme, which cassette is referred to as a CORE-DSB-cassette.

In specific embodiments that include in the cassette a double-strand break site and nucleic acid sequence encoding a double-strand break enzyme, the method further comprises inducing expression of the double strand break enzyme, thereby stimulating a double-strand break within the cassette, which double-strand break stimulates recombination.

In specific examples of the provided methods of deleting a target double stranded nucleic acid sequence, the first portion of the cassette is homologous to a nucleic acid sequence on a first side of the insertion point; and the second portion of the cassette is homologous to a second nucleic acid sequence on the second side of the insertion point.

Still other specific examples of such methods further involve transforming the cell with a second oligonucleotide comprising a nucleic acid sequence homologous to the second strand of a nucleic acid 5' of the target double stranded nucleic acid sequence; wherein the sequence of the first oligonucleotide is homologous to at least 10 nucleotides at the 3' end of the sequence of the second oligonucleotide.

In still further specific examples, the sequence of the first oligonucleotide is homologous to at least 15 nucleotides at the 3' end of the sequence of the second oligonucleotide.

In yet other examples, the second oligonucleotide further comprises a sequence homologous to the second strand of a nucleic acid 3' of the nucleic acid sequence of interest.

In specific examples, the second oligonucleotide is fully complementary to the first oligonucleotide.

For specific examples of those embodiments that involve or require a counterselectable marker, the counterselectable marker is KlURA3, URA3, TRP5, TRP1, or a gene encoding a toxin. In particular examples, the counterselectable marker is a gene encoding a toxin, and the toxin is an inducible restriction enzyme or an inducible p53 gene. By way of example, the inducible p53 gene in some instances is a toxic version.

In yet a further embodiment of a method of deletion of a target double stranded nucleic acid, the reporter encodes a polypeptide that confers antibiotic resistance to the cell, for instance wherein the antibiotic is G418, hygromycin, kanamycin, ampicillin, tetracycline, chloramphenicol, neomycin, zeocin, nourseothricin, cycloheximide, or canavanine. Alternatively, in other embodiments the reporter encodes a polypeptide from an amino acid or nucleotide synthesis pathway. For instance, the polypeptide is LEU2, TRP5, TRP1, LYS2, HIS3, or ADE2 in specific examples.

In specific examples of methods for deleting a target double stranded nucleic acid, the oligonucleotide is at least 30 nucleotides in length., for instance at least 40, at least 50, or at least 80 nucleotides in length. In other specific examples, the first and the second oligonucleotides are each at least 20 nucleotides in length, for instance at least 30, at least 40, at least 50, or at least 80 nucleotides in length.

In further embodiments, the first and the second oligonucleotide are of different lengths. In still other embodiments of these methods, the first and the second oligonucleotides are at least 20 nucleotides in length and wherein the region of overlap at the 3' ends is at least 10 base pairs, or the first and the second oligonucleotides are at least 40 nucleotides in length and wherein the region of overlap at the 3' ends is at least 15 base pairs.

In particular example methods, the 3' ends of the first and second oligonucleotide can be extended by in vitro polymerization.

In examples of the provided methods, the cell is a cell of an organisms in which homologous recombination can be accomplished. By way of example, the cell is a fungus cell (for instance, a yeast cell), a bacteria cell, a plant cell, or an animal cell (for instance, a chicken cell). Optionally, such cells can comprises a human chromosome or fragment thereof. Also provided in a further embodiment is a method for assessing a mutation in a nucleic acid sequence to determine if the mutation affects a function or expression pattern of the nucleic acid, which method comprises a delitto perfetto mutagenesis method as described herein. Another method is a method for analyzing a series of a mutations in a nucleic acid sequence, which method involves performing the method assessing a mutation in a nucleic acid sequence to determine if the mutation affects a function or expression pattern of the nucleic acid a plurality of times, wherein at least two different mutations are introduced in the nucleic acid sequence; and analyzing the function or expression pattern of the nucleic acid, thereby analyzing a series of a mutations in the nucleic acid sequence.

In examples of these methods, the nucleic acid sequence is a mammalian sequence. In other examples, the nucleic acid sequence encodes a polypeptide. In yet further examples, the method further comprises assessing a function of the polypeptide.

Optionally, the described methods are carried out in a cell of a haploid yeast, or in a cell of a diploid yeast.

Another embodiment is use of a described method as a diagnostic tool wherein a series of strains or cell lines are created, each with the cassette at a different position within a gene, such that mutations can be introduced anywhere within a gene and the biological consequences assessed.

Yet another embodiment is a method of analyzing defects in p53 wherein a p53 mutant protein is expressed in yeast in such a way that an impact of a defect in the p53 mutant protein can be assessed. Optionally, such a method further comprises assessing a defect in the p53 mutant protein.

Yet further embodiments are CORE-cassette constructs, RE-DSB-cassette constructs, and CORE-DSB-cassette constructs for use in delitto perfetto mutagenesis.

Also provided in other embodiments are integrative recombinant oligonucleotides (IRO) for use in delitto perfetto mutagenesis.

Yet a further embodiment is a kit for carrying out in vivo mutagenesis or deletion of a nucleic acid sequence, comprising an amount of a CORE-cassette construct, a RE-DSB-cassette construct, or a CORE-DSB-cassette construct, and an amount of an integrative recombinant oligonucleotide.

IV. Delitto Perfetto Mutagenesis

This disclosure provides mutagenesis systems based on transformation with oligonucleotides, which systems provide for the rapid creation of site-specific or random mutations in DNAs. In certain embodiments, the mutagenesis is carried out within the yeast *Saccharomyces cerevisiae*.

The two-step, cloning-free methods generate mutated products in vivo having only the desired mutation, such as single or multiple base changes, an insertion, or a small or a large deletion. Delitto perfetto mutagenesis is extremely versatile. It enables multiple rounds of specific or random changes within a specified window of up to 200 bp, and in some embodiments even longer windows, for instance up to 220, 250, 270, 290, 300, 350, 400 or more nucleotides.

The delitto perfetto process, which is at least partially dependent on the RAD52 pathway, is not constrained by the distribution of naturally occurring restriction sites and requires minimal DNA sequencing. Since yeast is commonly used for random and selective cloning of genomic DNA from higher eukaryotes such as YACs, this strategy also provides an efficient way to create precise changes within mammalian DNA sequences.

The mutagenesis system is referred to herein generally as delitto perfetto (Italian: meaning perfect murder but used as an idiom for perfect deletion) because the introduction of the desired mutation involves the complete removal of a marker cassette (the CORE-cassette) previously integrated at the target locus.

Figure 1:
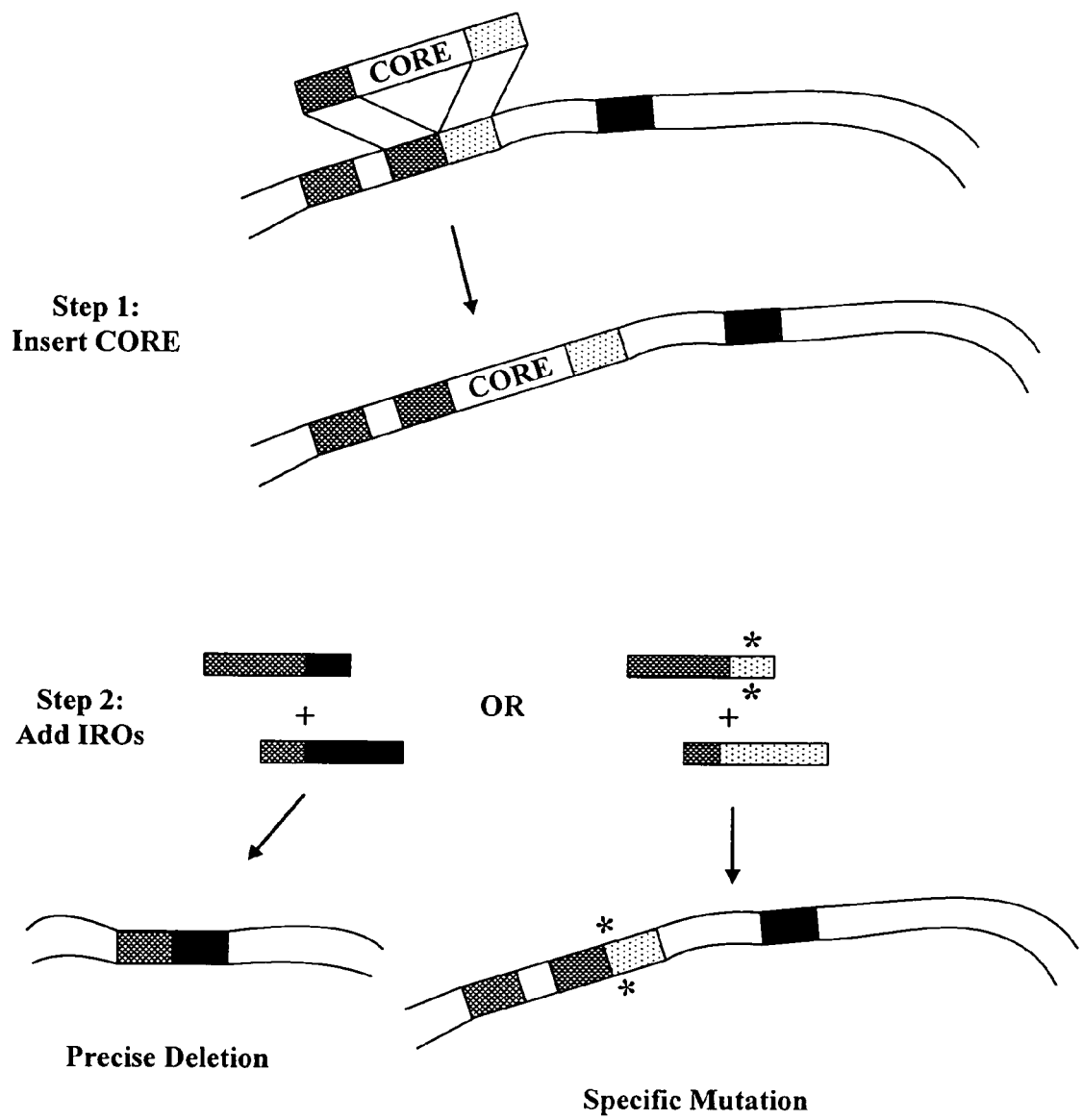
FIG. 1 is a schematic drawing illustrating two embodiments of the delitto perfetto system using integrative recombinant oligonucleotides (IROs); one embodiment illustrates the deletion of a sequence, and the other illustrates the creation of a specific point mutation.

As shown in FIG. 1, the first step is the introduction of a CORE-cassette containing a COunterselectable marker (e.g., KlURA3) and a REporter gene (e.g., kanMX4) near the site in which one or more changes are desired. The insertion of the CORE-cassette, using the highly proficient homologous recombination system in yeast (Fincham, *Microbiol. Rev.* 53, 148-70, 1989 [published erratum appears in *Microbiol. Rev.* 55(2):334, 1991]; Lewis and Resnick, *Mutat. Res.* 451:71-89, 2000; Sung et al., *Mutat. Res.* 451:257-275, 2000), is key to the delitto perfetto mutagenesis approach.

Transformation of the cells that contain a CORE-cassette with one or two Integrative Recombinant Oligonucleotides (IROs) leads to excision of the CORE-cassette. Counterselection for loss of the counterselectable marker, for instance the KlURA3 marker, followed by testing for simultaneous loss of the reporter (e.g., the kanMX4 marker) provides selection for desired changes and minimizes false positives. The type of mutation that results is dictated by the IRO(s) used in excising the CORE-cassette. Specific embodiments are described more fully below, and certain embodiments are illustrated in the Examples.

While additional mutations may be associated with the various targeted nucleic acid changes using delitto perfetto mutagenesis, they have always been confined to the IRO regions (those regions of the target nucleic acid that share homology with the IRO(s)).

Site-Specific Point Mutagenesis

To generate site-specific point mutations using delitto perfetto mutagenesis, one or both of the IROs used for transforming the cells contains the desired mutation(s). One embodiment is illustrated in FIG. 1, in the right hand pair of illustrated oligonucleotides. A single base mutation is indicated by the asterisk; in the illustrated embodiment, the mutation is found in both of the oligonucleotides (thus, is within the region of overlap or complementarity between the oligonucleotides).

In other embodiments, the point mutation is in one of the overhanging regions of the oligonucleotide pair. See, for instance, the embodiment illustrated in FIG. 5C, which incorporates a single nucleotide change into the target nucleic acid 40 nucleotides outside of the overlapping portion of the pair of oligonucleotides.

The further out a mutation is toward the end of an IRO, the higher the odds that the transforming recombinational event will occur "inside" of the mutation, which yields a cell that has lost the CORE-cassette without incorporating the desired point mutation. In certain embodiments the point mutation are no closer than about 20 nucleotides, for instance no closer than about 40 nucleotides, to the end of an IRO. This position will allow sufficient nucleic acid sequence in which the homologous recombination can occur, without excluding the point mutation.

It is also possible to incorporate more than one point mutation into a target nucleic acid sequence simultaneously, by using IRO(s) that contain more than one nucleic acid change compared to the target. In certain embodiments all of these multiple mutations are no closer than about 20 nucleotides, for instance no closer than about 40 nucleotides, from the end of an IRO.

Random Mutagenesis

As illustrated schematically in FIG. 5B, the delitto perfetto approach can also be used for random mutagenesis directly in the genome. Oligonucleotides with degenerate (i.e., random) sequence are commercially available, for instance from Invitrogen or other suppliers of oligonucleotides. The region of the IROs that is not in the overlap can be designed for random mutagenesis, simply by generating (e.g., ordering from a supplier) a random oligonucleotide, including a sequence with one or more ambiguous bases (example: N=A+C+T+G, R=A+G, etc.). This approach can be used to concurrently generate several or many different mutants in a defined DNA region.

By way of example, random mutagenesis methods can be applied, for instance, to structure-function studies, particularly for targeting multiple and mutations to key regions within a sequence such as specific protein motifs (which are usually short), or to defined loops (which are typically around 10 to 20 residues in length).

Deletion Mutagenesis

The delitto perfetto mutagenesis system also can be used to delete sequences from within a nucleic acid molecule. Such deletions can be short (i.e., a few to several nucleotides, such as a portion of a coding sequence or regulatory sequence) or longer (i.e., an entire gene or region of a chromosome). Deletion of a relatively long nucleic acid sequence is schematically illustrated in FIG. 1, with the left-hand pair of oligonucleotides. In the illustrated embodiment, the IROs have been designed to contain nucleic acid sequence that is both upstream and downstream of the inserted CORE-cassette (indicated with hatched and broad slashed boxes on the gene sequence and primers). When the IROs mediate homologous recombination and loss of the CORE-cassette, the recombination events take place well outside of the CORE-cassette, and thus the entire region of nucleic acid from within the hatched area to within the broad slashed area is lost.

In other embodiments, one of the IROs (or both of them) will carry a short deletion mutation, for instance of one to 15 nucleic acids. This enables the introduction of short deletions, using a mechanism essentially similar to that observed for the site-directed mutagenesis embodiments described above.

Deletion Mutagenesis of Essential Genes

Similarly, delitto perfetto mutagenesis can be used to generate deletions of genes that are essential to the cell in which the mutagenesis is being carried out. In this embodiment, a copy of the essential gene is transformed into the cell on, for instance, a plasmid. This plasmid copy of the gene provides function (in some examples, under inducible or inhibitable control) while the other (e.g., genomic) copy of the gene can be mutated at will using delitto perfetto mutagenesis. An example of the mutagenesis of essential genes is provided below.

General Mutagenesis of Essential Genes

Mutations can also be created in essential genes using delitto perfetto mutagenesis, for instance by inserting the CORE cassette downstream from the stop codon of the target essential gene and using oligonucleotides or larger PCR products to create non-lethal mutations.

Delitto Perfetto Mutagenesis on Genes Encoded on YACs

Sequencing of the genomes of several higher eukaryotes, including humans, has produced a need for functional evaluation of large numbers of genes. However, the feasibility of characterizing large, complex DNA molecules is limited by the difficulty in generating appropriate specific mutations. A disadvantage of present systems for modification of large DNA molecules is that they all require in vitro mutagenesis, which depends on laborious subcloning of the region to be mutagenized. See, for instance, Barton et al., *Nucleic Acids Res.* 18, 7349-7355, 1990; McCormick et al., *Proc. Natl. Acad. Sci. USA* 92:10147-10151, 1995; Peterson et al., *Trends Genet.* 13:61-66, 1997; Boren et al., *Genome Res.* 6:1123-1130, 1996; Callow et al., *Nucleic Acids Res.* 22:4348-4349, 1994; Tucker and Burke, *Nucleic Acids Res.* 24:3467-3468, 1996; and Nefedov et al., *Nucleic Acids Res.* 28:E79, 2000.

The disclosed mutagenesis methods expand opportunities for functional analysis of mammalian DNAs, or any nucleic acid sequence (e.g., a genomic sequence) cloned on a YAC. Yeast has proven ideal for the isolation and propagation of specific chromosomal regions and genes from higher eukaryotes. For example, TAR (transformation-associated recombination) cloning (Larionov et al., *Proc. Natl. Acad. Sci. USA* 93:491-496, 1996) can be used for the isolation of functional human genes, such as BRCA 1, BRCA2 and HPRT (Larionov et al., *Proc. Natl. Acad Sci. USA* 94, 7384-7387, 1997; Kouprina et al., *Proc. Natl. Acad Sci. USA* 95:4469-4474, 1998). The delitto perfetto methods provide a convenient tool for modifying TAR-cloned genes.

Delitto Perfetto to Characterize Protein Domains

The delitto perfetto mutagenesis approach can be applied to characterize specific motifs or domains of proteins. This may be particularly interesting for studies of genes associated with human diseases. The yeast *S. cerevisiae* is one of the most used model systems to study and analyze function of expressed heterologous genes. Several assays have been established in yeast to characterize protein function and analyze the effect of defined protein modifications, including ADE2-color assay for p53 mutants (Flaman et al., *Proc. Natl. Acad Sci.* 92: 3963-3967, 1995), growth assay for p53 mutants (Inga et al., *Oncogene* 20:501-513, 2001), growth assay for human FEN-1 mutants (Greene et al, *Hum. Mol. Genet.* 8: 2263-2273, 1999); an hsRPB4/7-dependent yeast assay for transactivation by the EWS oncogene (Zhou and Lee, *Oncogene* 20:1519-1524, 2001); a cell-based screen in yeast for the identification of novel inhibitors of poly(adp-ribose) polymerase/parp1 and parp2 (Perkins et al, *Cancer Res.* 61: 4175-4183, 2001); yeast-based transcription assay for functional analysis of human BRCA1 C-terminal missense mutations identified in breast and ovarian cancer families (Vallon-Christersson et al, *Hum. Mol. Genet.* 10: 353-360, 2001).

Adapted Yeast Backgrounds for Delitto Perfetto Mutagenesis

Specific mutant yeast strains such as those carrying mutations in or that disrupts a recombination system can be used to enhance targeting of genes in the delitto perfetto mutagenesis system. Specific examples include hpr1, hpr5 and rsc1 mutants in yeast; see, for instance, Aguilera and Klein, *Genetics* 119:779-790, 1988; Aguilera and Klein, *Mol. Cell. Biol.* 10:1439-1459, 1990; Schneiter et al., *Mol. Cell. Biol.* 19:3415-3422, 1999; Gallardo and Aguilera, *Genetics* 157: 79-89, 2001; Cairns et al., *Mol. Cell* 4:715-723, 1999; and Goodwin and Nicolas, *Gene* 268:1-7, 2001. In particular, these mutants are thought to lead to increased spontaneous recombination as well as enhancing targeting of the CORE-cassette. These mutants along with mutations in genes affecting nuclease (e.g., the exo1 or mre11 nucleases; Tiskoff et al., *Proc. Natl. Acad. Sci. USA* 94:7487-7492, 1997; Tran et al., *Mol. Cell. Biol.* 19:2000-2007, 1999; Bressan et al., *Mol. Cell. Biol.* 19:7681-7687, 1999; and Symington et al., *Nuc. Acids Res.* 28:4649-4659, 2000), including the specific mre11 D16A mutant, are also expected to lead to increased efficiency of IRO targeting. For example, IROs are expected to be more stable in the nuclease mutants.

Although the listed examples are in the yeast system, similar examples of mutations that are advantageous for delitto perfetto mutagenesis are found in other organisms, for instance mutants in the recBC gene of *E. coli*.

Mutagenesis in Diploid Yeast

The delitto perfetto system can be applied to diploid yeast strains as well as haploids. For example, the CORE-cassette is inserted into one of the pair of homologues in a diploid strain, essentially as explained for insertion in a haploid strain. Transformation of that strain with one or a pair of IROs leads to loss of CORE-cassette and corresponding replacement within the genome. Due to recombination during cell division, prior to transformation with the IRO(s) there may be a substantial background of homozygous CORE-cassette deletions. However, the efficiency of targeting is sufficiently high (comparable to haploids) to make the delitto perfetto strategy worthwhile in diploids. Furthermore, use of targeting mutants described above, especially the nuclease mutants, is expected to increase the relative frequency of delitto perfetto events in comparison to the background of CORE-cassette minus cells.

Delitto Perfetto in other Species

Although several of the illustrative embodiments are disclosed in a yeast (*S. cerevisiae*) system, it is believed that the delitto perfetto mutagenesis methods work in all biological organisms that have a functional recombination system, even where the recombination system is not as proficient as in yeast. Other cells or cell types that have a functional homologous recombination systems include bacteria such as *Bacillus subtilis* and *E. coli* (which is RecE RecT recombination proficient; Muyrers et al., *EMBO rep.* 1: 239-243, 2000); protozoa (e.g., *Plasmodium, Toxoplasma*); other yeast (e.g., *Schizosaccharomyces pombe*); filamentous fungi (e.g., *Ashbya gossypii*); plants, for instance the moss *Physcomitrella patens* (Schaefer and Zryd, *Plant J.* 11: 1195-1206, 1997); and animal cells, such as mammalian cells and chicken DT40 cells (Dieken et al., *Nat. Genet.* 12:174-182, 1996). Application to DT40 cells is especially useful since cell lines with specific human chromosomes are available (Koi et al., *Cytogenet. Cell Genet.* 76:72-76, 1997). It is also possible to use mammalian cells, since some lines exhibit higher rates of recombination (see, e.g., Bunz et al., *Science* 282: 1497-1501, 1998).

Plasmids used in yeast can be easily shuttled to *E. coli*. Alternatively, the system is believed to apply to a variety of other organisms capable of recombination, such as *E. coli* and chicken cells, which in each case may be engineered to contain human chromosomes or portions thereof.

Production of Oligonucleotides

In vitro methods for the synthesis of oligonucleotides are well known to those of ordinary skill in the art; such conventional methods can be used to produce IROs for the disclosed methods. The most common method for in vitro oligonucleotide synthesis is the phosphoramidite method, formulated by Letsinger and further developed by Caruthers (Caruthers et al., *Chemical synthesis of deoxyoligonucleotides,* in *Methods Enzymol.* 154:287-313, 1987). This is a non-aqueous, solid phase reaction carried out in a stepwise manner, wherein a single nucleotide (or modified nucleotide) is added to a growing oligonucleotide. The individual nucleotides are added in the form of reactive 3'-phosphoramidite derivatives. See also, Gait (Ed.), *Oligonucleotide Synthesis. A practical approach,* IRL Press, 1984.

In general, the synthesis reactions proceed as follows: First, a dimethoxytrityl or equivalent protecting group at the 5' end of the growing oligonucleotide chain is removed by acid treatment. (The growing chain is anchored by its 3' end to a solid support such as a silicon bead.) The newly liberated 5' end of the oligonucleotide chain is coupled to the 3'-phosphoramidite derivative of the next deoxynucleoside to be added to the chain, using the coupling agent tetrazole. The coupling reaction usually proceeds at an efficiency of approximately 99%; any remaining unreacted 5' ends are capped by acetylation so as to block extension in subsequent couplings. Finally, the phosphite triester group produced by the coupling step is oxidized to the phosphotriester, yielding a chain that has been lengthened by one nucleotide residue. This process is repeated, adding one residue per cycle. See, for instances, U.S. Pat. Nos. 4,415,732, 4,458,066, 4,500,707, 4,973,679, and 5,132,418. Oligonucleotide synthesizers that employ this or similar methods are available commercially (e.g., the PolyPlex oligonucleotide synthesizer from Gene Machines, San Carlos, Calif.). In addition, many companies will perform such synthesis (e.g., Sigma-Genosys, Tex.; Operon Technologies, Calif.; Integrated DNA Technologies, Iowa; and TriLink BioTechnologies, Calif.).

Modified nucleotides can be incorporated into an oligonucleotide essentially as described above for non-modified nucleotides.

Random primers may be generated using known chemical synthesis procedures; randomness of the sequence may be introduced by providing a mixture of nucleic acid residues in the reaction mixture at one or more addition steps (to produce a mixture of oligonucleotides with random sequence). See, for instance, U.S. Pat. Nos. 5,043,272 and 5,106,727. A random primer preparation (which is a mixture of different oligonucleotides, each of determinate sequence) can be generated by sequentially incorporating nucleic acid residues from a mixture of, for instance, 25% of each of dATP, dCTP, dGTP, and dTTP, (or a modified dNTP such as aa-dUTP). Other ratios of dNTPs can be used (e.g., more or less of any one dNTP, with the other proportions adapted so the whole amount is 100%). Likewise, in the synthesis of a random primer, the synthesizer can be programmed to introduce one or more known residues (such as one or more specific nucleotide residues or modified nucleotide residues) at a defined location within the primer. For instance, a defined sequence can be in the middle of the primer (see FIG. 5B) that is used alone or coupled with a second primer (with random sequences to the 5' and 3' end), or a combination of these.

Presently, oligonucleotides are conveniently available commercially up to approximately 125 nucleotides; beyond this length the efficiency and purification drops. As the available size of oligonucleotide amenable to in vitro synthesis is increased, the applicability of delitto perfetto mutagenesis will be increased in terms of size of window available for mutational modification.

Applications of Delitto Perfetto Mutagenesis Techniques

Additional applications of delitto perfetto mutagenesis included targeted changes in the genome of various organisms, including yeast; modification of large human genes, for instance cloned in yeast as YACs, which could readily be moved to other species (e.g., *E. coli* or human cells) after mutagenesis; and larger windows of site-directed mutagenesis as the synthesis length of oligonucleotides becomes more accessible.

V. Delitto Perfetto-DSB Mutagenesis

Embodiments described above provide methods for targeted modification of the *Saccharomyces cerevisiae* genome, for instance, through homologous recombination and oligonucleotides. The ability to engineer specific changes directly into the genome so that no trace of the targeting material remains is generally a laborious, multistep process with limitations on the types of alterations. Furthermore, site-directed mutagenesis and functional analysis of changes can be labor intensive and low efficiency. The delitto perfetto process described above allows for the generation of products having only the desired mutation, such as a single or multiple base change, an insertion, a small or a large deletion. There is a clear need for a general usage of this technique that would allow for a) independence from the genetic background of a strain, b) possibility to accomplish large genome rearrangements, c) modifications in essential genes, even in genes that affect homologous recombination and d) the possibility of greater efficiency.

The delitto perfetto-DSB system is another embodiment of the delitto perfetto process, which provides a dramatic increase in efficiency, with an over 1000-fold increase in mutation efficiency. This results in considerably greater versatility and high throughput generation of genetic alterations using this embodiment. This novel system originates form the combination of the following factors: the generation of an unique double-strand break (DSB) in the genome to stimulate targeting, the use of an endonuclease enzyme that generates a DSB at a unique short DNA site, and the possibility to turn on and off the endonuclease enzyme using an inducible promoter.

In addition to its relevance as a fundamental biological process, DSB-mediated recombination is the basis of gene modification in yeast and in other eukaryotes (reviewed in Paques and Haber, *Microbiology and Molecular Biology Reviews* 1999, 63:349-404). The repair of DSBs in *S. cerevisiae* seems to occur predominantly by recombination between the broken ends of a DNA molecule and intact homologous sequences. DSBs greatly stimulate homologous recombination: DSBs are the sole instigators of recombination in meiotic cells and are a major factor in recombination in mitotic cells. DSBs can appear as a consequence of ionizing radiation, by mechanical stress, by replication of a single-stranded nicked chromosome, or by endonucleases expressed in vivo.

In mitotic cells, initiation of recombination can be accomplished by the induction of a site-specific specific endonuclease. Two such system have been developed in yeast. The HO endonuclease recognizes a degenerate target sequence of 22 bp, and normally cleaves only one site in the entire yeast genome, the mating-type (MAT) locus. Constructs in which the HO gene is fused to a galactose-inducible promoter have made it possible to express HO simply by adding galactose.

A second endonuclease is I-SceI, normally encoded and expressed only in yeast mitochondria to facilitate the movement of a mobile intron (cut site produced below). A synthetic version of this gene, replacing codons whose usage is different in the mitochondria and the cytoplasm, was constructed, again under the control of a galaxies-inducible promoter (Plessis et al., *Genetics* 130:451-460, 1992). A 45- to 90-minute induction of either HO or I-SceI leads to the cleavage of a significant fraction of target sites.

I-SceI site

↓

5' - TAGGGATAACAGGGTAAT- 3'

3' - ATCCCTATTGTCCCATTA - 5'
↑

Use of a CORE-DSB Cassette for Delitto Perfetto-DSB Mutagenesis

This embodiment provides certain advantages over the delitto perfetto embodiment, with an over 1000-fold increase in efficiency. Thus, the delitto perfetto-DSB embodiments provide greater versatility and permit higher throughput generation of genetic alterations. This embodiment is based on the introduction of a single DSB within a CORE-cassette in the targeted region at the time of transformation using an in vivo, tightly regulatable system (see FIG. 7). Through the use of this novel system we have established that oligonucleotide modifications can be created in up to 5% of all cells, an extremely highly efficient process. Since the system provides for the generation of multiple mutations in 200 bp or larger windows, it is useful in the modification of genes and proteins that are of health relevance, and for the generation of diversity within proteins.

The delitto perfetto-DSB system greatly enhances opportunities for the rapid modification of genes and DNAs, diversification of genes, alteration of genes in diploid cells, the use of targeting cassettes that do not depend on counterselection (e.g., RE-DSB, as described below), in vivo modification of essential genes, manipulation of large chromosomal regions, and gene modification in cells deficient in recombination.

The utility of the system extends to all the features of the delitto perfetto system including: it does not require subcloning, it does not rely on the need for unique restriction sites and it does not require resequencing of large regions of DNA once a modification is made. Only the region corresponding to the oligonucleotides need be sequenced. The system could be used in other organisms where recombination is proficient, for example in chicken DT40 cells which are used for examining human chromosomes, or in cells such as human where DSBs can stimulate recombination. This could have a variety of health benefits, especially in the areas of gene therapy and protein development.

Shortened CORE-DSB-cassettes (Without Counterselection); RE-DSB Mutagenesis

In another embodiment, due to the high-efficiency mutagenesis that results from using the DSB system, the counterselectable marker can be omitted from the cassette.

Since the mutagenesis approach that utilizes the CORE-DSB is highly efficient, between 2 to 5%, it is possible to isolate the clones containing the desired change in the genome directly on a nonselective media (YPD plate), without the use of the counterselectable marker. In this case, the delitto perfetto-DSB approach can be accomplished with a CORE-DSB cassette that lacks the counterselectable marker, referred to as RE-DSB (for example GAL1/10:: I-SceI+kanMX4 or +HygroR).

Externally Added DSB Enzyme

In another embodiment, the CORE-DSB-cassette does not contain a sequence encoding a double-strand break enzyme, and instead the double-strand break function is provided by adding exogenous double-strand break enzyme to the cells after the CORE-DSB-cassette (or RE-DSB-cassette) has been integrated into the target sequence. The approach of adding an external enzyme to cut at a unique site in vivo to induce recombination has been used with various mammalian cell systems, including the use of I-SecI. See, for instance, Lin et al., (*Mol. Cell Biol.* 19:8353-60, 1999) and Johnson and Jasin (*Biochem. Soc. Trans.* 29:196-201, 2001).

Generation of Mutations in Diploid Organisms

The delitto perfetto-DSB approach described herein provides enhanced opportunities to accomplish mutagenesis in diploid yeast. Normally, mutations in diploid organisms are often masked because they are recessive and therefore undetectable. The delitto perfetto-DSB system provides for recognition of a mutational change by virtue of loss of the cassette event and therefore enables the identification and isolation of diploid clones with the desired change. While loss of heterozygosity may also occur, the frequency of the targeted changes are sufficiently large that they can be identified in a relatively small number of clones, such as 1 in 50, 1 in 100, or 1 in 200.

Generation of Diversity within Proteins

The delitto perfetto-DSB system enables very efficient targeting mediated by oligonucleotides. The possibility to obtain a huge number of targeted clones can be used, for instance, to create multiple variants of a protein product of a gene of interest. This diversity of protein products can be obtained if the gene of interest is integrated into the yeast genome (or into another genome where homologous recombination is also proficient), or is cloned on a plasmid. The insertion of the CORE-DSB or RE-DSB cassette within the gene at the desired locus, followed by induction of the DSB, allows for rapid creation of many variants, upon transformation with IROs designed for random mutagenesis. This provides the possibility of at least one and up to many changes per IRO-targeted event, thereby providing opportunities for diversifying genes (or protein products).

This approach to random modification of genes directly in vivo using IROs is expected to be much more efficient than in vitro approaches to random mutagenesis using oligonucleotides. If the gene is cloned on a multicopy vector (such as a yeast 2µvector) the number of variant forms of the gene generated can be up to 1000-fold, for instance, 100-fold, 250-fold, or 500-fold, higher (as described below) than if a single copy vector or a genomic locus is used. For instance, it is believed that up to $10^8$ different variants can be obtained from a single transformation event. In some embodiments, the random mutagenesis approach is performed to isolate a particular variant form of the derived protein that gives rise to a selectable phenotype.

Generation of Intracellular Plasmid Variants by Oligonucleotide Gap Repair of an in Vivo Linearized Multicopy Vector The cassette CORE-DSB or RE-DSB can be cloned in vitro at a desired site within a desired gene on a multi copy vector (for instance, YEps (yeast episomal plasmids), 2-micron (2µ) derivative vectors for yeast Saccharomyces cerevisiae). The YEp vector containing the CORE-DSB or the RE-DSB is transformed by standard procedure into yeast cells. Inside the yeast cells the copy number of each YEp plasmid is spontaneously increased to 50-100 or more copies per cell.

Immediately prior to transformation with IROs cells are grown in the presence of the inducer (i.e., galactose), which induces the site-specific endonuclease expression (i.e. I-SceI). The enzyme targets its single site in the cassette on each YEp vector and generates a DSB, linearizing all vectors in each cell. IROs are designed for random mutagenesis, as described herein.

Cells are transformed with IROs and selected for the presence of the plasmid. Transformation of cells with IROs leads to circularization of the vectors, loss of the cassette and creation of the random mutation (theoretically, a different mutation is created in each vector). Since each cell contains several vectors, each cell should contain many different variants of the same gene.

This approach could be useful to increase the number of gene variants obtained by random mutagenesis of additional 10- to 100-fold or more.

Increased Efficiency of PCR Targeting, and Modification of Essential Genes

The delitto perfetto-DSB mutagenesis approach using the CORE-DSB or the RE-DSB utilizes IROs for making genome modification. However, the same approach can also be applied using a PCR product (in place of IROs), previously modified by random mutagenesis or site-directed mutagenesis in vitro or in vivo. The efficiency of PCR targeting directly in vivo in the genome is also increased about 1000-fold after DSB induction.

This can be applied to all nonessential genes and even to essential genes directly if the cassette is inserted immediately after the stop codon of the gene.

For instance, a CORE-DSB or RE-DSB cassette can be inserted immediately after the stop codon of a chosen essential gene, without disrupting the gene. After induction of the DSB, a modified PCR product of the chosen gene can replace the cassette and the wild copy of the gene, leaving in the same locus a modified version of the gene. IROs can also be used but in this case only the 3' part of the gene (the part close to the cassette) can be modified.

Co-Transformation of Oligonucleotides and a Vector

The extremely high efficient transformation produced with delitto perfetto-DSB and oligonucleotides allows the possibility to accomplish co-transformation experiments efficiently: transformation of IROs and a plasmid in one step. This allows for coincident modification of a gene along with the specific expression of another gene. For example, a gene on a plasmid might be lethal and another gene might impact on the lethality such that deletion of the impact gene enables survival. Therefore, could create a set of mutations in the vicinity of a CORE-DSB site in the impacting gene such that the mutants enable survival with the lethal gene. Also, it may be possible to include the gene for the DSB cutting enzyme on a plasmid so that the cuts are produced at the time of IRO plus plasmid transformation.

DSB-Based Mutagenesis in Low-recombination Strains and Cells

As discussed herein, in the delitto perfetto system, the integration of IROs (whether presented singly or as pairs to cells) replacing the original CORE-cassette, was dependent on the RAD52 gene and appeared to be partially dependent on RAD50 and MRE11. It has now been surprisingly found that, once a CORE-DSB (or RE-DSB) cassette is placed into the genome, the DSB-enhanced approach can be used even in the absence of a highly efficient recombination system.

By way of example, one could target to a recombination gene, i.e., inactivate the recombination gene and create mutations in it. Since the induction of a DSB in the integrated cassette results in extremely efficient targeting using IROs, the change in targeting efficiency is detectable even in the absence of a highly efficient recombination system, for instance in a genetic situation with a RAD52-null gene (see, e.g., Example 8).

Genome-Level Rearrangements

Use of delitto perfetto mutagenesis (with or without DSB) permits generation of wide genome rearrangements. By way of example, such rearrangements included large-scale deletions, such as those demonstrated herein for up to 16 kb using a delitto perfetto CORE-cassette. Since the use of the CORE-DSB or the RE-DSB provides for about 1000-fold higher efficiency of targeting, large deletions such as these, and larger, can be accomplished with a very high efficiency. Substantially larger deletions (e.g., up to 100 kb) are contemplated and expected to be produced efficiently using CORE-DSB or RE-DSB-based mutagenesis. This may find applications in the modifications of YAC clones, for example.

Other kinds of contemplated rearrangements include chromosome circularization. Previously this was accomplished by linearized plasmid transformation with regions homologous to the ends of a chromosome, a highly inefficient process (Bennett et al., *Mol. Cell. Biology*, 12: 5359-5373, 2001). A cassette can be integrated near to a telomeric region of a chosen chromosome. Then IROs (single or a pair) can be designed containing at the 5' end a sequence homologous to the downstream region of the left telomere and at the 3' end a sequence homologous to the upstream region of the right telomere. Addition of the IRO(s) to the cell will cause the elimination of the cassette and of both the telomeres; therefore, the chromosome will be circularized.

The invention is illustrated by the following non-limiting Examples.

EXAMPLES

Example 1

Site-Directed Delitto Perfetto Mutagenesis

The delitto perfetto approach permits genomic modification without the retention of heterologous sequence (FIG. 1). Since integration of the CORE-cassette utilizes simple, straightforward integrative transformation procedures (Wach et al., *Yeast* 10, 1793-1808, 1994) and the mutation replacement involves transformation by easily designed oligonucleotides, this system provides for the rapid creation of a variety of genetic changes, as discussed below. Unlike other systems, this in vivo site-specific mutagenesis strategy is versatile with regard to chromosomal change, since many types of modification can be generated in the nearby region once a CORE-cassette is inserted.

This example provides a description of several sequence modifications that have been made using the delitto perfetto in vivo mutagenesis system.

Experimental Protocols

Unless otherwise stated, genetic manipulations were carried out according to standard methods (Sambrook et al., (eds.), *Molecular Cloning: A Laboratory Manual*, CSH Laboratory Press, Cold Spring Harbor, N.Y., 1989).

Yeast strains and growth conditions. Yeast strains used were: BY4742 (MATα, his3Δ1, leu2 Δ 0, lys2 Δ 0, ura3 Δ 0; Brachmann et al., *Yeast* 14:115-132, 1998), VL6α (MATα, met14,lys2-801, his3-Δ 200, trp1-Δ 63, ura3-52, ade2-101; Lewis et al., *Mol. Cell Biol.* 18:1891-1902, 1998) and E133 (S1-A12: MATα, ade5-1, lys2-12A, trp1-289, his7-2, leu2-3, 112, ura3-52; Tran et al.,*Mol. Cell Biol.* 17:2859-2865, 1997).

Cells were grown in standard rich (YPD), glycerol (YPG) and synthetic minimal medium without uracil (SD Ura⁻), leucine (SD Leu⁻), or tryptophan (SD Trp⁻) (Sherman et al. (eds.) *Methods in Yeast Genetics*, Cold Spring Harbor Laboratory Press, Cold Spring Harbor, N.Y., 1986). Geneticin (G418) resistant cells were grown on YPD plates containing 200 μg/ml of G418 (Gibco BRL, Grand Island, N.Y.) (Wach et al., *Yeast* 10, 1793-1808, 1994). Ura⁻ cells were selected on synthetic complete medium containing 5-fluoroorotic acid (5-FOA) (Toronto Research Chemicals Inc., North York, Ontario, Canada) at 1 mg/ml (Boeke et al., *Mol. Gen. Genet.* 197:345-346, 1984).

Plasmids. The plasmid pCORE was constructed by cloning a 1.5 kb BamHI-HincII fragment containing the kanMX4 gene (Wach et al., *Yeast* 10, 1793-1808, 1994) into the BamHI-SspI sites of pFA6aKlURA3 (Delneri et al., *Yeast* 15:1681-1689, 1999).

Plasmid pBL230 (Ayyagari et al., *Mol. Cell Biol.* 15:4420-4429, 1995) harbors genomic DNA containing the POL30 gene (from 195 bp upstream of the ATG to 170 bp downstream of its stop codon).

Deletion of RAD52 was made using plasmid pΔ52Leu (Lewis et al., *Mol. Cell Biol.* 18:1891-1902, 1998) cut with ApaI and NotI.

pLKL67Y was created by cloning a 1.2 kb URA3 fragment from pRS315+URA3 into the XhoI-SacI sites of the multiple-restriction site (of the centromeric vector pRS313 (Sikorski and Hieter, *Genetics* 122:19-27, 1989).

Yeast Transformation. Transformation of yeast with circular plasmids, linear double-stranded stranded DNA molecules, or oligonucleotides was performed according to a high efficiency lithium acetate protocol as previously described (Gietz, "High efficiency transformation with lithium acetate" in: In *Molecular Genetics of Yeast. A Practical Approach*. (ed. Johnston) IRL Press, Oxford, UK, 121-134, 1994).

PCR Amplification and Sequence Analysis. The kanMX4 and KlURA3 CORE-cassette was amplified as a 3.2 kb DNA fragment from pCORE using Taq DNA polymerase (Roche, Indianapolis, Ind.), with 32 cycles of 30 seconds at 94° C., 30 seconds at 56° C., and 3 minutes 20 seconds at 72° C. For integration of the CORE-cassette into chromosomal loci, chimeric 70-mers were designed, consisting of 50 nucleotides homologous to the appropriate flanking region of the genomic target locus and 20 nucleotides, shown here, which allow for the amplification of the CORE-cassette:

5'- . . . GAGCTCGTTTTCGACACTGG-3' for the kanMX4 side (SEQ ID NO: 1) and

5'- . . . TCCTTACCATTAAGTTGATC-3' for the KlURA3 side (SEQ ID NO: 2).

Amplification using these 70-mers yielded PCR product with 50 nucleotides each of the upstream and downstream chromosomal sequence, flanking the CORE-cassette itself.

To identify clones with correct CORE-cassette integration, colony PCR (Huxley et al., *Trends Genet.* 6:236, 1990) was performed using primers designed for annealing upstream and downstream of the integration locus and within the CORE-cassette.

PCR fragments (about 0.5 kb) for the new mutant constructs, together with their corresponding wild-type loci, were purified by phenol-chloroform extraction, purified using the QIAquick PCR Purification Kit (Qiagen USA, Valencia, Calif.) and used for DNA sequencing. Sequencing reactions were performed on both strands using the dRhodamine Terminator Cycle Sequencing Kit (ABI Prism, Applied Biosystems, Foster City, Calif.) and run in an automatic sequencing machine (AB1377; Applied Biosystems).

Initial insertion of the CORE cassette into genes MLP2, POL30, TRP5 and SIR2 (within codon 270 and between codons 354 and 355) was performed using the following primers, respectively:MLP2.U/MLP2.G, PCNA.U/PCNA.G, TRP5.U/TRP5.G, SIR2.U1/SIR2.G1, and SIR2.U2/SIR2.G2. K2 and URA3.2 are internal primers in the CORE cassette, within kanMX4 and KlURA3, respectively.

CORE insertion was verified at each locus using the following primer combinations: MLP2.1/MLP2.2/K2 and MLP2.3/MLP2.4/URA3.2; PCNA.3/PCNA.4, PCNA.3/URA3.2 and PCNA.4/K2; TRP5.1/TRP5.2, TRP5.1/K2 and TRP5.2/URA3.2; SIR2.1/SIR2.4/K2 and SIR2.1/SIR2.4/URA3.2 for CORE insertion in codon 270 of SIR2; SIR2.2/SIR2.3/K2 and SIR2.2/SIR2.3/URA3.2 for CORE insertion between codons 354 and 355 of SIR2.

CORE-cassette excisions and sequence analyses were carried out using the following primers: MLP2.1/MLP2.4; PCNA.3/PCNA.4; TRP5.1/TRP5.2; SIR2.1/SIR2.4 for CORE excision from codon 270 of SIR2 and SIR2.3/SIR2.2 for CORE excision between codons 345 and 364 of SIR2.

Primers used to verify deletion of RAD52: RAD52.1/LEU2.2 and RAD52.4/LEU2.1.

Integrative Recombinant Oligonucleotide (IRO) Mutagenesis

IROs used in this study differ by size and orientation with respect to the CORE-cassette integration point.

Oligonucleotides were used in transformation experiments as single species, or in two-species combinations as shown in FIG. 3. To extend the sequence of the 3'-overlapping IROs (a+b) in vitro, a 50-μl reaction mix contained 0.5 nmoles of each primer, 4 units Platinum Pfx (Gibco BRL), 5 μl 10× Buffer, 1 μl 50 mM MgSO4 and 2 μl 10 mM dNTPs (Roche). Extension was performed as follows: 1 minute at 94° C. and 30 seconds to 3 minutes at 68° C. Samples were ethanol precipitated and resuspended in 10-20 μl water. The use of Taq polymerase (Roche) instead of Platinum Pfx DNA polymerase for these extension reactions partially reduced the efficiency of oligonucleotide integration.

Before adding IRO DNA to the cells, the single oligonucleotide species or the two oligonucleotide species-combinations, except for the pair extended in vitro with Pfx DNA polymerase (a+b Pfx), were denatured at 100° C. for 2 minutes and then placed immediately on ice in order to reduce or eliminate possible secondary structure.

IROs used in this Example are described with numbers indicating the DNA sequences spanned by each oligonucleotide, starting from the first 5' nucleotide and terminating with the last 3' base relative to the CORE-cassette integration point shown in FIG. 2.

The IROs used to delete MLP2 were MLP2.a (5'−70 . . . −1, +1 . . . +10) and MLP2.b (5'+70 . . . +1, −1 . . . −10).

IROs used to generate the POL30 deletion were PCNA.a (5'−848 . . . −778, +1 . . . +10) and PCNA.b (5'+70 . . . +1, −778 . . . −788).

IROs used to generate the silent mutation in the codon 334 of TRP5 were TRP5.a (5'−70 . . . −1, +1 . . . +10), TRP5.b (5'+70 . . . +1, −1 . . . −10), TRP5.c (5'+10 . . . +1, −1 . . . −70), TRP5.d (5'−10 . . . −1, +1 . . . +70), TRP5.e (5'−47 . . . −1, −1 . . . +48), TRP5.f (5'−48 . . . +1, −1 . . . −70), TRP5.d (5'−40 . . . −1, +1 . . . +41), TRP5.f1 (5+41 . . . +1, −1 . . . −40), TRP5.e2 (5'−25 . . . −1, +1 . . . +26), TRP5.f2 (5'+26 . . . +1, −1 . . . −25), TRP5.i (5'−127 . . . −47) and TRP5.j (5'+128 . . . +48).

IROs used to generate the G270A mutation in SIR2 were 270.a (5'−70 . . . −1, +1 . . . +10), 270.b (5'+70 . . . +1, −1 . . . −10), 270.e (5'−48 . . . −1, +1 . . . +47), 270.f (5'+47 . . . +1, −1 . . . −48); IROs used to generate the N345A mutation in SIR2 were 345.a (5'−85 . . . −1, +1 . . . +10) and 345.b (5'+70 . . . +1, −1 . . . −10).

IROs used to generate the H364Y mutation in SIR2 were 364.a (5'−70 . . . −1, +1 . . . +10) and 364.b (5'+85 . . . +1, −1 . . . −10).

IROs used to generate the K40A mutation in RAD50 were RAD50.a (5'−70 . . . −1, +1 . . . +10) and RAD50.b (5'+70 . . . +1, −1 . . . −10).

IROs used to generate the D16A mutation in MRE11 were MRE.a (5'−69 . . . −1, +1 . . . +11) and MRE.b (5'+71 . . . +1, −1 . . . −9).

Cells from each transformation were spread on a single YPD plate, incubated at 30° C. and replica-plated to 5-FOA the following day. After three days, colonies were replica-plated to YPD, G418, Trp⁻ (for TRP5 experiments) and YPG (to select against petite mutants) plates.

Results

Deletion of Genomic Sequences

The delitto perfetto strategy was used to delete the entire MLP2 gene from the start to the stop codon (FIG. 2A), such that no heterologous DNA was retained after the deletion process was complete. The CORE-cassette was targeted by standard homologous recombination techniques into three commonly used yeast strain backgrounds (BY4742, VL6α and E133) so as to replace the MLP2 ORF. This generated cells that were Ura+(5-FOA sensitive) and G418 resistant.

Two 80-nucleotide (nt) IROs (designated MLP2.a and MLP2.b) were designed with a 20 base overlap at their 3' ends. Annealing and in vitro extension of MLP2.a and MLP2.b resulted in a 140-bp double-strand molecule that contains 70 bp homologous to the sequence upstream and downstream regions of the CORE-cassette. Cells were transformed with these double-stranded molecules.

As shown in Table 1, the frequency of 5-FOA resistant (5-FOA$^R$), G418 sensitive (G418$^s$) cells was about 100 transformants/0.5 nmoles of IRO DNA (35-45 μg) added per $10^7$ viable cells. All the G418$^s$ clones tested by colony PCR had lost the cassette and were ΔMLP2. Since about half of the 5-FOA$^R$ clones were G418 resistant (presumably due to mutations in the KlURA3-encoding sequence), G418 sensitivity was diagnostic of CORE-cassette loss. Three 5-FOA$^R$, G418$^s$ BY4742 isolates were h one contained the correct deletion (ΔMLP2). One of the isolates had acquired a point mutation in the 140-bp IRO region.

TABLE 1

Accuracy of targeted changes with delitto perfetto

| Strain | Locus | Designed change | IRO species used[a] | 5-FOA$^R$/ $10^7$ cells[b] | G418$^S$/ $10^7$ cells[c] | Correctly excised CORE[d] | Correctly targeted clones[e] | Clones w/o additional changes[f] |
|---|---|---|---|---|---|---|---|---|
| BY4742 | MLP2 | Δ ORF | MLP2.a+b Pfx | 225 | 97 | 18/18 | 3/3 | 2/3 |
| VL6α | MLP2 | Δ ORF | MLP2.a+b Pfx | 215 | 118 | 6/6 | ND | ND |
| E133 | MLP2 | Δ ORF | MLP2.a+b Pfx | 284 | 101 | 6/6 | ND | ND |
| E133 | POL30 | Δ ORF | PCNA.a+b Pfx | 70[g] | 4[g] | 9/12 | ND | ND |
| BY4742 | TRP5 | A334A (BamHI) | TRP5.a+b Pfx | 190 | 130 | 50/50 | 50/50 | 19/20 |
|  |  |  | TRP5.e+f | 286 | 212 | 40/40 | 40/40 | 11/15 |
| BY4742 | SIR2 | G270A | 270.a+b Pfx | 302 | 105 | 20/20 | 20/20 | 13/20 |
|  |  |  | 270.a+b | 151 | 27 | 20/20 | 20/20 | 17/20 |
|  |  |  | 270.e+f | 237 | 150 | 19/19 | 19/19 | 16/19 |

TABLE 1-continued

Accuracy of targeted changes with delitto perfetto

| Strain | Locus | Designed change | IRO species used[a] | 5-FOA[R]/ 10[7] cells[b] | G418[S]/ 10[7] cells[c] | Correctly excised CORE[d] | Correctly targeted clones[e] | Clones w/o additional changes[f] |
|---|---|---|---|---|---|---|---|---|
| BY4742 | SIR2 | N345A | 345.a+b Pfx | 263 | 126 | 11/11 | 9/11 | 6/11 |
| BY4742 | SIR2 | H364Y | 364.a+b Pfx | 210 | 42 | 14/14 | 12/14 | 6/14 |
| VL6α | RAD50 | K40A | RAD50.a+b Pfx | 169 | 7 | 6/6 | 3/3 | 2/3 |
| VL6α | MRE11 | D16A | MRE11.a+b Pfx | 205 | 6 | 6/6 | 3/3 | 3/3 |

[a] In vitro extension of IROs is indicated with Pfx. When Pfx is not mentioned, the IROs were added directly to the cells.
[b] Number of 5-FOA[R] clones per 10[7] viable cells transformed with 0.5 nmoles of each IRO.
[c] Transformation frequency: number of G418[S] clones per 10[7] viable cells, per 0.5 nmoles of each IRO.
[d] Number of clones with correct CORE-cassette excision/number of random samples tested by colony PCR.
[e] Number of clones that acquired the targeted change/number of samples sequenced, or digested with BamHI.
[f] Number of targeted clones without additional mutations/number of samples sequenced.
[g] Mean value of three experiments. ND, not determined.

Deletion of Essential Genes

The delitto perfetto approach was next applied to the deletion of essential genes by integrating the CORE-cassette downstream from the gene. The CORE-cassette was integrated beyond the stop codon of the POL30 gene (PCNA) (FIG. 2B) in strain E133, and a wild-type copy of the gene on a plasmid (pBL230) was introduced into the cell. Cells were then transformed with the overlapping IROs PCNA.a and PCNA.b that had homology upstream of the start codon of the POL30 gene and downstream of the CORE-cassette.

Among twelve 5-FOA[R] G418[s] colonies obtained in three experiments, nine had a precise deletion of the chromosomal POL30 gene (Table 1). The reduced frequency of CORE-cassette replacement by IROs, as compared to the MLP2 deletion embodiment described above, likely is due to the recombination competition with the plasmid-borne copy of POL30. Loss of the CORE-cassette was usually associated with a replacement event and not due to recombination with the plasmid.

The deletion clones generated in this manner were unable to lose the POL30 plasmid after over 30 generations in nonselective medium, whereas the plasmid was readily lost in control cells containing the wild-type chromosomal POL30 gene.

Site-Specific Mutagenesis

The delitto perfetto strategy was also applied to the rapid creation of site-specific mutations in the genome (FIG. 1). One embodiment of this method was demonstrated by the introduction of a silent mutation in the TRP5 gene, which mutations generate a new BamHI site (FIG. 2C).

The CORE-cassette was targeted into the TRP5 gene of strain BY4742 between nt 1002 and 1003, resulting in Trp[−] cells (BY4742-TRP5-CORE). The resultant cells were transformed with the two 80-nt IROs TRP5.a and TRP5.b containing the BamHI mutation site adjacent to the CORE-cassette insertion site, and subsequently 5-FOA[R] G418[s] colonies were isolated (Table 1). Among 50 clones tested, all had lost the CORE-cassette and acquired the desired targeted mutation. Of 20 G418[s] clones sequenced, 19 did not have additional mutations.

Thus, embodiments of the delitto perfetto mutagenesis technique can be used for the efficient creation of site-specific changes using, for instance, IROs with a 20-bp overlap.

Multiple Rounds of Site-Specific Mutagenesis

Once the CORE-cassette is integrated into a sequence, multiple site-specific modifications can be generated simply by designing new oligonucleotides and repeating the IRO transformation procedure. To demonstrate this, the delitto perfetto strategy was applied to site-specific changes in the regions surrounding two positions of CORE-cassette integration (codon 270 and between codons 354 and 355) in the SIR2 gene (FIGS. 2D and 2E). Mutations were contained in either the overlapping regions (IROs 270.a+b) or in just one of the pair oligonucleotides (345.a+b, and 364.a+b).

Following annealing and DNA synthesis (with Pfx polymerase), the strains were transformed using IRO pairs 270.a+b and 345.a+b, or 364.a+b, respectively. As expected, all 5-FOA[R] G418[s] clones had lost the CORE-cassette, based on colony PCR (Table 1). The site-directed mutation targeting was highly efficient. For the IROs containing a mutation near the CORE-cassette, all clones had acquired the correct change (20/20), as shown in Table 1. For the IROs with a mutation external to the original oligonucleotide overlap, over 80% of the clones had the correct site-specific change (21/25).

Site-Directed Mutagenesis Using a Single IRO

Figure 4A:
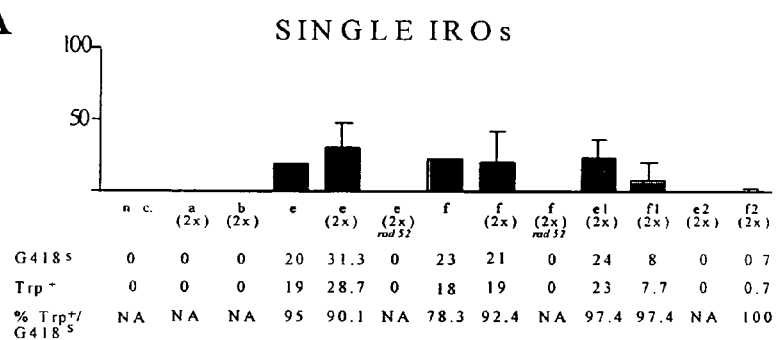

Site-directed mutagenesis can be accomplished by adding individual oligonucleotides directly to cells, rather than pairs of oligonucleotides. Single IROs were compared for their ability to create site-specific mutations when added directly to cells. The strain BY4742-TRP5-CORE was transformed with several IROs (FIG. 3) that would yield the silent BamHI mutation in TRP5 (FIG. 2C). The 95 nt (e or f) and 81 nt (e1 or f1) single IROs that extend to either side of the CORE-cassette were comparably effective at generating site-directed mutations when added individually (FIG. 4A). The minimum length of homology for efficient mutagenesis was between 25 and 40 nt (compare the 51-mers e2 and f2 with e1 and f1).

Site-Directed Mutagenesis Using Various Pairs of IROs

Figure 4B:
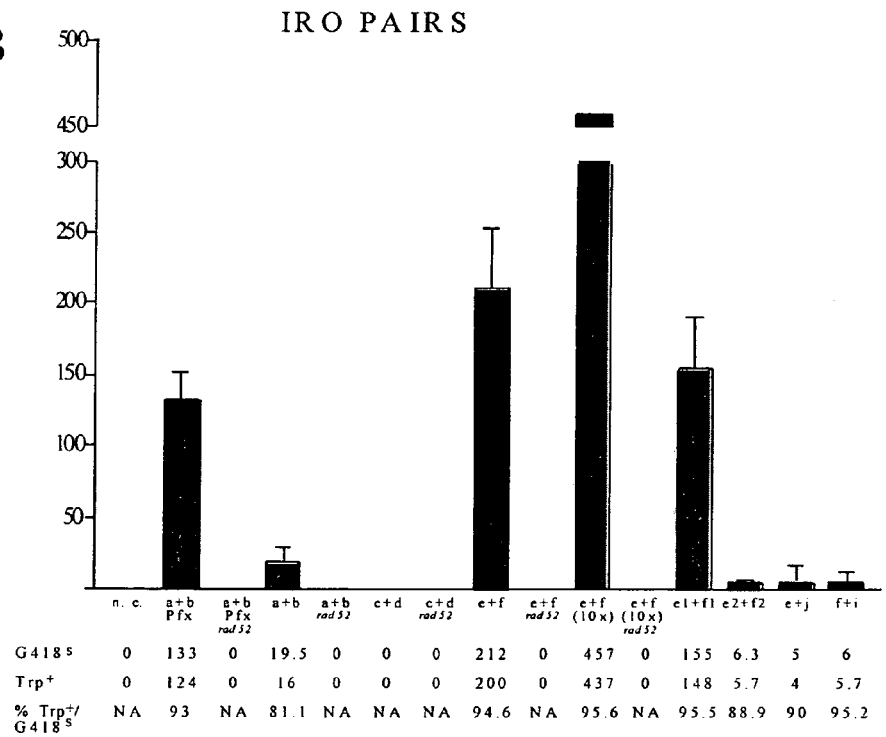

Combinations of IROs were also examined for their ability to create the same site-specific mutation. Individual IROs were added directly to competent cells without in vitro annealing or extension. As shown in FIG. 4B, modification by unannealed pairs of 81 or 95-nt IROs was highly efficient if they were fully complementary; the frequencies were even higher than those for oligonucleotides annealed and extended in vitro. As observed with single IROs, the minimum homology required for efficient mutagenesis was between 25 and 40 nt (e2+f2 vs. e1+f1).

Surprisingly, the combination of TRP5.a+b, having only a 20 bp 3'-overlap, was also able to create the site-specific change at a level about one-sixth of that found for these pairs of DNA oligonucleotides when annealed and extended in vitro (TRP5.a+b Pfx). A similar pair of oligonucleotides, but with opposite polarity resulting in 5'-overlaps (c+d in FIG. 3) yielded no transformants.

TRP5.e+j or TRP5.f+i, which do not overlap, showed no transformation increase over either TRP5.e or TRP5.f alone. Similar results were obtained for modifications at SIR2 codon 270 (see FIG. 2D) in strain BY4742 using corresponding single and double IROs (270.a, b, c, d, e, f, e1, f1, e2, f2, j and i).

Site-specific targeting by complementary IROs was highly efficient; after positive/negative selection nearly all the isolates had lost the CORE-cassette and acquired the desired mutation. Confirmation of successful mutation is greatly simplified because only the region covered by the oligonucleotides needs to be sequenced in a small number of samples; mutations outside this region were never detected. For example, among the clones that were sequenced for the TRP5 (A334A-BamHI) and SIR2 G270A changes, 5-35% associated point mutations were found in the IRO region when complementary oligonucleotides were extended in vitro or were used directly (Table 1).

While a single IRO could be used for mutagenesis, the efficiency was much greater with pairs of overlapping IROs. In addition, the targeting efficiency was greater as the size of single and complementary IROs was increased (FIGS. 4A and 4B). This differs from a previous report using single-stranded oligonucleotides (Moerschell et al., Proc. Natl. Acad. Sci. USA 85, 524-528, 1988), which system did not utilize a counterselection scheme that requires elimination of a large region (i.e., the CORE-cassette). Possibly, the reliance of delitto perfetto mutagenesis on a recombinational pathway (see below) accounts for the difference.

In certain embodiments, the efficiency of the delitto perfetto method was greatest when fully complementary oligonucleotides that were≧81 nt long were used (FIG. 3 and FIG. 4B). The two pairs of IROs that gave the highest integration efficiencies were complementary 95-mers e+f and extended a+b oligomers (a+b Pfx) that could yield a 140 double-strand molecule. IROs such as e+f appear to be the most practical for introducing specific point mutations anywhere within a 15-nt region and can be used to create small or large deletions as described in FIGS. 1 and 5A. Pairs of IROs with no overlap were no more effective than using the respective individual IROs. DNAs with 3'-end overlaps were moderately efficient even without in vitro annealing and extension; however, IROs that had overlapping 5'-ends were not productive. This suggests that strands with as few as 20 overlapping nucleotides can anneal during the transformation procedure and lead to efficient site-specific mutation through a process that probably involves DNA synthesis. However, it is possible that the annealed structure interacts directly with chromosomal DNA. It also appears that there is little DNA degradation within the cell since protected oligonucleotides that were phosphorothioated at their 3' and 5' ends did not increase the transformation efficiency of the IRO pairs (TRP5.a+b, TRP5.c+d, or TRP5.e+f).

As demonstrated with the SIR2-N345A and H364Y mutations, once the CORE-cassette is inserted at a particular location, the DNA can be modified with different pairs of IROs at distances that span the CORE at least 30 bp upstream and downstream without moving the cassette. Based on the reported results, it is believed that specific mutations can be created up to 100 nt from a CORE-cassette using 100-nt IROs with a 20-nt overlap, as shown in FIG. 5C. This is a significant advance over other approaches for the study of specific regions since in all other mutagenesis procedures each step in the creation of site-specific mutations must be repeated from the beginning, even for additional modifications of the same residue.

Additional mutations found within targeted clones were never detected outside the sequence covered by IROs. The spectrum of additional mutations within the sequence replaced by IROs included 70% deletions and was as follows: 46.7% 1-bp deletions, 26.7% 1-bp substitutions, 16.7% 2-bp deletions, 6.6% 1-bp deletions plus single bp substitutions and 3.3% duplications of part of an IRO sequence.

Example 2

Targeting by IROs in Delitto Perfetto Involves Homologous Recombination

Since the RAD52 gene is important for nearly all types of homologous recombination, its role in delitto perfetto mutagenesis was examined. Wild-type and mutant (RAD52::LEU2; two independent isolates) strains were transformed with a control centromeric plasmid pLKL67Y (containing the HIS3 and URA3 genes), or the following TRP5 IROs: (1) a+b Pfx, (2) a+b, (3) c+d, (4) e+f, (5) e and (6) f.

In repeated transformations with pLKL67Y, the wild-type transformation level was about 4-fold higher than for the rad52 mutant ($4.3 \times 10^5/\mu g$ vs. $\sim 1 \times 10^5/\mu g$, respectively), apparently due to reduced plating efficiency in the rad52 mutant. No 5-FOA$^R$ G418$^s$ clones were observed in the rad52 strain with various IROs in three separate experiments even when 10 times more e+f was used (FIGS. 4A and 4B). Complete RAD52 dependence was also observed for modifications at SIR2 codon 270 (see FIG. 2D) using IROs 270.a+b Pfx, 270.a+b, and 270.c+d. These results indicate that oligonucleotide replacement during delitto perfetto mutagenesis is mediated by a recombinational mechanism.

The importance of the RAD50 and MRE11 genes, which function in recombination as well as double-strand break end-joining, on IRO site-directed changes was examined also. The CORE-cassette was integrated in strain VL6α into each gene, at positions described in FIGS. 2F and G. IROs were created that produce an AA to CG substitution in RAD50 at codon 40 and an A-to-C transversion in codon 16 of MRE11. Even though the efficiency of removal of the CORE-cassette was low with the respective a+b Pfx IROs, several G418$^s$ colonies were obtained that had a correct excision of the CORE-cassette (Table 1). Sequence analysis of three G418$^s$ isolates for both RAD50 and MRE11 showed that the expected modifications had occurred in all clones and only one isolate (of RAD50) displayed an additional point mutation. Thus, the oligonucleotide integration process is RAD52-dependent at the level of mutation detection used (contrast with delitto perfetto-DSB, below), but there appears to be less dependence on the RAD50 and MRE11 genes.

The integration of IROs, whether presented singly or as pairs to cells, was completely dependent on the RAD52 gene in this example, and appeared to be partially dependent on RAD50 and MRE11. The relatively moderate effect of the latter genes is consistent with their having a smaller effect on recombination (Lewis and Resnick, Mutat. Res. 451:71-89, 2000). While they have been implicated in DNA end-joining, the absence of an effect on IRO-mediated integration in sir2 mutants, which are deficient in end-joining (Lewis and Resnick, *Mutat. Res.* 451:71-89, 2000), suggests that their role in delitto perfetto is specific to recombination.

The minimum amount of homology required for efficient recombination at the ends of transforming molecules in yeast is about 30 bp (Manivasakam et al., *Nucleic Acids Res.* 23:2799-2800, 1995). Similarly, results using delitto perfetto mutagenesis suggest that the minimum length of homology in IROs must be between 25 and 40 nt.

In contrast to the methods reported herein, the DNA-RNA chimeric oligonucleotide mutagenesis system in higher eukaryotes is not mediated by homologous recombination (Cole-Strauss et al., *Nucleic Acids Res.* 27:1323-1330, 1999; Yoon et al., *Proc. Natl. Acad. Sci. USA* 93:2071-2076, 1996), nor does the oligonucleotide approach in yeast described by Moerschell et al., *Proc. Natl. Acad. Sci. USA* 85, 524-528, 1988 (see also Erdeniz et al., *Genome Res.* 7, 1174-1183, 1997; Yamamoto et al., *Yeast* 8:935-948, 1992). The delitto perfetto system differs from those previously described at least in that small nucleic acid regions distant from each other (separated by the CORE-cassette) are brought into close proximity to be paired with the oligonucleotide sequences. This is believed to account for the requirement for the RAD52 epistasis group proteins.

Example 3

A Diagnostic Tool for Assessing Tumor Associated p53 Mutations

An expression cassette containing the human p53 coding sequence under the GAL1 promoter is integrated into a suitable chromosomal locus (e.g., LYS2 gene on chromosome III ) of a haploid yeast strain. As described in FIG. 1, the CORE-cassettes were targeted by transformation into seven different positions in the p53 coding sequence at 95 nucleotide intervals across the DNA binding region, from nucleotide 315 to nucleotide 885. Thus, a panel of seven isogenic yeast strains containing one CORE-cassette at each of the indicated positions were created. Oligonucleotides containing desired p53 mutations were designed to replace by transformation the closest CORE-cassette in the appropriate strain resulting in the appropriate site-directed mutation. Changes are confirmed by in vitro amplification (e.g., PCR) and sequence analysis of the p53 coding sequence region containing the introduced mutation.

The consequences of the human associated p53 mutations can be examined by expressing each mutated p53 molecule and examining the ability to induce transcription at various p53 responsive elements, corresponding to p53 responsive genes. Systems for addressing in vivo p53 affinity/specificity are described in, for instance, Inga et al. (*Oncogene* 20:501-513, 2001); and in Inga and Resnick (*Oncogene* 20:3409-3419, 2001).

This is a demonstration of integrating the CORE-cassette at positions corresponding to the site between amino acid 26 and 27 in p53. A set of oligonucleotides were used to create a variety of mutations at or near this site. Using that set of CORE and oligonucleotides, mutations were made in Ser 15, 20, 33, 37, 47 and Thr 18 creating alanine or aspartate changes.

Example 4

Alternative CORE-Cassettes

Four alternative CORE-cassettes were constructed in the basic pFA6a *E. coli* vector, in order to expand the applicability of the delitto perfetto approach to every yeast strain (also to URA$^+$ and $G_{418}^R$ strains), including wild type strains. Two different heterologous markers were considered, a reporter that provides resistance to hygromycin and a new countereslectable marker, which is a variant of the p53 protein (V122A). When the variant p53 is highly expressed under an inducible GAL1/10 promoter, growth of yeast is prevented. By a combination of these markers with the previous markers (KlURA3 and kanMX4) four new cassettes were made: CORE-UK (KlURA3 and kanMX4), CORE-UH (KlURA3 and HygroR), CORE-KpS3 (kanMX4and GAL-p53) and CORE-Hp53 (HygroR and GAL-p53). Similar CORE-cassettes can be used with other selectable and counterselectable genes.

Experimental Protocols

Yeast strains and growth conditions. Yeast strains used were: BY4742, and VL6α. Cells were grown in standard rich (YPD), glycerol (YPG) and synthetic minimal medium without uracil (SD Ura$^-$), or tryptophan (SD Trp$^-$). Geneticin (G418) resistant cells were grown on YPD plates containing 200 μg/ml of G418. Hygromycin resistant cells were grown on YPD plates containing 200 μg/ml of hygromycin (Invitrogen, Carlsbad, Calif.). Ura cells were selected on synthetic complete medium containing 5-fluoroorotic acid (5-FOA). Cells that have lost the CORE cassette containing the p53 gene were selected on synthetic complete media containing 2% galactose in place of glucose (GAL) (Sherman et al. (eds.) *Methods in Yeast Genetics,* Cold Spring Harbor Laboratory Press, Cold Spring Harbor, N.Y., 1986).

Plasmids. The plasmids containing the new CORE-cassettes were termed: pCORE-UK, pCORE-UH, pCORE-Kp53, pCORE-Hp53. Plasmid pCORE-UK was constructed by cloning a 1.5 kb SacI-SmaI fragment containing the kanMX4 gene (Wach et al., *Yeast* 10, 1793-1808, 1994) into the SacI-HpaI sites of pFA6aKlURA3 (Delneri et al., *Yeast* 15:1681-1689, 1999). The plasmid pCORE-UH was constructed by cloning a 1.7 kb SacI-SmaI fragment containing the hygromicin resistance (HygroR) gene from the pAG32 vector (Goldstein and McCusker, *Yeast* 14, 1541-1553, 1999) into the SacI-HpaI sites of pFA6aKlURA3. pCORE-Kp53 was constructed by cloning a 2.1 kb EcoRI-SpeI fragment containing the p53 V 122 gene under the GAL1/10 promoter (Inga and Resnick, *Oncogene* 20, 3409-3419, 2001) into the EcoRI-SpeI sites of pFA6akanMX4 (Wach et al., *Yeast* 10, 1793-1808, 1994). pCORE-Hp53 was constructed by cloning a 1.7 kb SacI-BamHI fragment containing the HygroR gene from pAG32, into the SacI-BglII sites of pCORE-Kp53, replacing the kanMX4 gene.

PCR amplification and sequence analysis. The CORE-UK, -UH, -Kp3 and -Hp53 cassettes were amplified as a 3.2, 3.5, 3.7 and 4.0 kb DNA fragment, respectively from the corresponding vectors using Taq DNA polymerase (Roche, Indianapolis, Ind.), with 32 cycles of 30 seconds at 94° C., 30 seconds at 56° C., and 4 minutes at 72° C.

For integration of the CORE-cassettes into chromosomal loci, chimeric 70-mers were designed, consisting of 50 nucleotides homologous to the appropriate flanking region of the genomic target locus and 20 nucleotides, shown here, which allow for the amplification of all the four CORE-cassettes (these oligos do not work to amplify the original CORE cassette):

5'-... TTCGTACGCTGCAGGTCGAC-3' for the KIURA3 side in pCORE-UK and pCORE-UH and for the kanMX4 or HygroR side in pCORE-Kp53 and pCORE-Hp53, respectively (entire oligonucleotide shown in SEQ ID NO: 61) and 5'-... CCGCGCGTTGGCCGATTCAT-3' for the kanMX4 or HygroR side in pCORE-UK and pCORE-UH, respectively, and for the GAL1/10-p53 side in pCORE-Kp53 and pCORE-Hp53 (entire oligonucleotide shown in SEQ ID NO: 62).

Amplification using these 70-mers yielded PCR product with 50 nucleotides each of the upstream and downstream chromosomal sequence, flanking the CORE-cassettes themselves. Initial insertion of the CORE-cassettes into gene the TRP5gene was performed using the following primers: TRP5.I/TRP5.II (SEQ ID NOs: 61 and 2). K1 (SEQ ID NO: 74), H1 (SEQ ID NO: 76), URA3.1 (SEQ ID NO: 75) and p7 (SEQ ID NO: 77) are internal primers in the CORE-cassettes, within kanMX4, HygroR, KIURA3 and GAL1/10-p53, respectively.

CORE-UK insertion was verified at the TRP5 locus using the following primer combinations: TRP5.1/URA3.1 (SEQ ID NOs: 21 and 75) and TRP5.2/K1 (SEQ ID NOs: 22 and 74). CORE-UH insertion was verified at the TRP5 locus using TRP5.1/URA3.1 and TRP5.2/H 1. CORE-Kp53 insertion, using TRP5.1/K.1 (SEQ ID NOs: 21 and 74) and TRP5.2/p7 (SEQ ID NOs: 22 and 74); and CORE-Hp53 insertion, using TRP5.1/H.1 (SEQ ID NOs: 21 and 76) and TRP5.2/p7 (SEQ ID NOs: 22 and 77). CORE-cassettes excision and sequence analysis was carried out using the following primers: TRP5.1/TRP5.2 (SEQ ID NOs: 21 and 22).

Integrative recombinant oligonucleotide (IRO) mutagenesis. IROs used to generate the silent mutation in the codon 334 of TRP5 were TRP5.e (5'−47 ... −1, +1 ... +48; SEQ ID NO: 35), TRP5.f(5'+48 ... +1, −1 ... 47; SEQ ID NO: 36).

Cells from each transformation were spread on a single YPD plate, incubated at 30° C. and replica-plated to 5-FOA or GAL plates the following day. Cells growing on GAL plates were replica-plated on fresh GAL plates every day, to reduce the background growth. After three days, colonies were replica-plated from 5-FOA or GAL to YPD, G418, Trp⁻ and YPG (to select against petite mutants) plates.

Results: Alternative CORE-cassettes and the use of p53 as a Counterselectable Marker Four additional CORE-cassettes were constructed: CORE-UK (KIURA3 and kanMX4), CORE-UH (KIURA3 and HygroR), CORE-Kp53 (kanMX4and GAL-p53) and CORE-Hp53 (HygroR and GAL-p53). All cassettes were tested in the delitto perfetto strategy for the rapid creation of site-specific and silent mutations in the TRP5 gene, where the mutations generate a new BamHI site, as described above. The CORE-cassette s were targeted into the TRP5 gene of strain BY4742 and VL6α between nt 1002 and 1003, resulting in Trp⁻ cells (BY4742-TRP5-CORE, and VL6α-TRP5-CORE). The resultant cells were transformed with the two 95-nt TRP5.e and TRP5.f containing the BamHI mutation site, and subsequently 5-FOA resistant, G418ˢ or HygroS colonies were isolated (Table 2).

TABLE 2

Efficacy of the different CORE-cassettes in delitto perfetto mutagenesis

| Strain[a] | Locus | Designed change | IRO species used[b] | 5-FOA[R]/ 10⁷ cells[c] | G418[S]/ 10⁷ cells[d] |
|---|---|---|---|---|---|
| BY4742-UK | TRP5 | A334A (BamHI) | TRP5.e+f | 315 | 177 |
| BY4742-UH | TRP5 | A334A (BamHI) | TRP5.e+f | 259 | 120 |
| BY4742-Kp53 | TRP5 | A334A (BamHI) | TRP5.e+f | 366 | 52 |
| BY4742-Hp53 | TRP5 | A334A (BamHI) | TRP5.e+f | 369 | 53 |
| VL6α-UK | TRP5 | A334A (BamHI) | TRP5.e+f | 115 | 33 |
| VL6α-UH | TRP5 | A334A (BamHI) | TRP5.e+f | 88 | 30 |
| VL6α-Kp53 | TRP5 | A334A (BamHI) | TRP5.e+f | 59 | 8 |
| VL6α-Hp53 | TRP5 | A334A (BamHI) | TRP5.e+f | 93 | 23 |

[a]Strain BY4742 and V16α where the different CORE-cassettes: CORE-UK, CORE-UH, CORE-Kp53 and CORE-Hp53 were integrated at the TRP5 locus.
[b]IROs were added directly to the cells.
[c]Number of 5-FOA[R] clones per 10⁷ viable cells transformed with 0.5 nmoles of each IRO.
[d]Transformation frequency: number of G418[S] or Hygro[S] clones per 10⁷ viable cells. per 0.5 nmoles of each IRO.

Four independent G418ˢ or Hygroˢ clones from each strain that were tested for the presence of the BamHI site demonstrated that the oligo targeting was correct. Thus, the p53 allele V122A can be used as a general counter-selectable marker.

Though illustrated here using the CORE-cassette format, the cassettes produced in this example could equally be used in CORE-DSB- and RE-DSB-cassette formats, simply by changing other elements in the cassette. This alternative embodiments are specifically contemplated and thereby included in this disclosure.

Example 5

Delitto Perfetto-DSB Mutagenesis

This example provides a representative description of delitto perfetto-DSB mutagenesis, in which an expression inducible double-strand break enzyme and corresponding double-strand break site are introduced into a cassette that contains a reporter marker (RE-DSB) or a counterselectable and a reporter marker (CORE-DSB). Induction and resultant expression of the double-strand break enzyme prior to introduction of the IRO stimulates double-strand breaks at the corresponding site, which results in very high frequencies of IRO mediated changes.

Experimental Protocols

Yeast strains and growth conditions. Yeast strains used were: BY4742 and E133a (S1-A12: MATα, ade5-1, lys2-12A, trp1-289, his7-2, leu2-3,112, ura3-52; unpublished), Cells were grown in standard rich (YPD), glycerol (YPG) and synthetic minimal medium without uracil (SD Ura⁻), or tryptophan (SD Trp⁻). Geneticin (G418) resistant cells were grown on YPD plates containing 200 µg/ml of G418. Hygromycin resistant cells were grown on YPD plates containing 200 µg/ml of hygromycin. Ura⁻ cells were selected on synthetic complete medium containing 5-fluoroorotic acid (5-FOA). Cells before transformation with oligonucleotides were grown in liquid synthetic complete media containing 0.02, 0.2 or 2% galactose in place of glucose (GAL).

Plasmids. The plasmids containing the CORE -DSB cassette were termed: pCORE-GALSceKU and pCORE- GALSceHU. Plasmid pCORE-GALSceKU and pCORE-GALSceHU were constructed by cloning a 1.4 kb BglII fragment containing the I-SceI gene under the GAL1/10 promoter into the BglII site of pCORE-UK and pCORE-UH. The 1.4 kb fragment containing the I-SceI gene under the GAL1/10 promoter was obtained by PCR amplification from the pWY203 vector (Galli and Schiestl, *Genetics* 149, 1235-1250, 1998) using the following primers: Sce.FI and Sce.R containing the BglII site.

PCR amplification and sequence analysis. The RE-DSB cassettes derived from pCORE-GALSceKU and pCORE-GALSceHU were amplified as a 2.7 and 3.0 kb DNA fragment, respectively from the corresponding vectors using Taq DNA polymerase (Roche, Indianapolis, Ind.), with 32 cycles of 30 seconds at 94° C., 30 seconds at 56° C., and 3 minutes at 72° C.

For integration of the short CORE-cassettes into chromosomal loci, one chimeric 70-mer and one chimeric 88-mer containing also the I-SceI site were designed, consisting of 50 nucleotides homologous to the appropriate flanking region of the genomic target locus and 20 and 38 nucleotides, shown here, which allow for the amplification of all the four CORE-DSB cassettes:

5'- . . . CATCTGGGCAGATGATGTCG-3' for the kanMX4 or the HygroR side (entire oligonucleotide shown in SEQ ID NO: 70) and 5'- . . . TAGGGATAACAGGGTAATTTGGATGGACGCAAAGAAGT-3' for the GAL1/10::I-SceI side (the I-SceI site is in bold) (entire oligonucleotide shown in SEQ ID NO: 65).

The CORE-DSB cassettes from pCORE-GALSceKU and pCORE-GALSceHU were amplified as a 4.6 and 4.9 kb DNA fragment, respectively from the corresponding vectors using Taq DNA polymerase (Roche, Indianapolis, Ind.), with 32 cycles of 30 seconds at 94° C., 30 seconds at 56° C., and 4 minutes and 30 seconds at 72° C.

For integration of the CORE-cassettes into chromosomal loci, one chimeric 70-mer and one chimeric 88-mer containing also the I-SceI site were designed, consisting of 50 nucleotides homologous to the appropriate flanking region of the genomic target locus and 20 and 38 nucleotides, shown here, which allow for the amplification of all the four CORE-DSB cassettes:

5'- . . . TTCGTACGCTGCAGGTCGAC-3' for the KlURA3 side (entire oligonucleotide shown in SEQ ID NO: 61) and 5'- . . . TAGGGATAACAGGGTAATTTGGATGGACGCAAAGAAGT-3' for the GAL1/10::I-SceI side (the I-SceI site is in bold) (entire oligonucleotide shown in SEQ ID NO: 65).

Initial insertion of the RE-DSB (I-SceI site+GAL1-I-SceI+kanMX4) or (I-SceI site+GAL1-I-SceI+HygroR) cassette into the TRP5 gene was performed using the following primers: TRP5.IK/TRP5.SceII. The I-SceI site can be placed on both sides of the cassette and in different orientations: TSce.IK/TRP5.II or TecS.IK/TRP5.II, or two inverted I-SceI sites can be placed together at one side of the cassette: TRP5.IK/TscecS.II, or two I-SceI sites can be placed at both sides of the cassette in direct (TSce.IK/TRP5.SceII) or opposite orientation (TecS.IK/TRP5.SceII) for both cassettes.

Amplification using these primers yielded PCR product with 50 nucleotides each of the upstream and downstream chromosomal sequence, flanking the CORE-DSB cassettes themselves. K.2, H.2 and Sce.2 are internal primers in the RE-DSB cassettes, within kanMX4, HygroR and GAL1/10I-SceI, respectively.

RE-DSB cassette insertion was verified at the TRP5 locus using the following primer combinations: TRP5.1/K2 or TRP5.1/H2 and TRP5.2/Sce.2.

CORE-cassette excision was carried out using the following primers: TRP5.1/TRP5.2.

Integrative Recombinant Oligonucleotide (IRO) Mutagenesis.

IROs used: TRP5.e (5'-47 . . . -1, +1 . . . +48), TRP5.f (5'+48 . . . +1, -1 . . . -47), TRP5.e1 (5'40 . . . -1, +1 . . . +41), TRP5.f1 (5'+41 . . . +1, -1 . . . -40), TRP5.e2 (5'-25 . . . -1, +1 . . . +26), TRP5.f2 (5'+26 . . . +1, -1 . . . -25), TRP5.e3 (5'-20 . . . -1, +1 . . . +21), TRP5.f3 (5'+21 . . . +1, -1 . . . -20), TRP5.e4 (5'-15 . . . -1, +1 . . . +16), TRP5.f4 (5'+16 . . . +1, -1 . . . -15).

Cells before transformation were grown for 20 minutes to 5 hours in liquid GAL in order to induce I-SceI endonuclease expression. The enzyme targets its site in the cassette and generates a DBS. Cells from each transformation were spread directly on Trp⁻ plates, or on YPD plates, incubated at 30° C.

Initial insertion of the CORE-DSB (I-SceI site+GAL1-I-SceI+kanMX4+KlURA3) or (I-SceI site+GAL1-I-SceI+HygroR+KlURA3) cassette into the TRP5 gene was performed using the following primers: TRP5.1/TRP5.SceII. The I-SceI site can be placed on both sides of the CORE and in different orientations: TSce.IU/TRP5.II or TecS.IU/TRP5.II, or two inverted I-SceI sites can be placed together at one side of the CORE: TRP5.I/TscecS.II, or two I-SceI sites can be placed at both sides of the CORE in direct (TSce.IU/TRP5.SceII) or opposite orientation (TecS.IU/TRP5.SceII) for both cassettes.

Amplification using these primers yielded PCR product with 50 nucleotides each of the upstream and downstream chromosomal sequence, flanking the CORE-DSB cassettes themselves. URA3.1 and Sce.2 are internal primers in the CORE-DSB cassettes, within KlURA3 and GAL1/10I-SceI.

CORE-DSB cassettes insertion was verified at the TRP5 locus using the following primer combinations: TRP5.1/URA3.1 and TRP5.2/Sce.2.

CORE-cassettes excision was carried out using the following primers: TRP5.1/TRP5.2.

Integrative recombinant oligonucleotide (IRO) mutagenesis. IROs used: TRP5.e (5'-47 . . . -1, +1 . . . +48), TRP5.f(5'+48 . . . +1, -1 . . . 47), TRP5.e1 (5'-40 . . . -1, +1 . . . +41), TRP5.f1 (5'+41 . . . +1, -1 . . . -40), TRP5.e2 (5'-25 . . . -1, +1 . . . +26), TRP5.f2 (5'+26 . . . +1, -1 . . . -25). Additional IROs used to generate the silent mutation in the codon 334 of TRP5 were TRP5.e3 (5'-20 . . . -1, +1 . . . +21), TRP5.f3 (5'+21 . . . +1, -1 . . . -20), TRP5.e4(5'-15 . . . -1, +1 . . . +16), TRP5.f4 (5'+16 . . . +1, -1 . . . -15).

Cells before transformation were grown for 20 minutes to 5 hours in liquid GAL, in order to induce I-SceI endonuclease expression. The enzyme targets its site in the cassette and generates a DBS. Cells from each transformation were spread directly on Trp⁻ plates, or on YPD plates, incubated at 30° C. and replica-plated to 5-FOA plates the following day. After three days, colonies were replica-plated from 5-FOA or GAL to YPD, G418, Trp⁻ and YPG (to select against petite mutants) plates.

Results: Delitto Perfetto-DSB System

The delitto perfetto-DSB strategy was applied to the high throughput creation of site-specific mutations in the genome in the TRP5 locus, by the introduction of a silent mutation in the TRP5 gene, where the silent mutation generates a new BamHI site.

The RE-DSB and CORE-DSB cassettes were targeted into the TRP5 gene of strain BY4742 between nt 1002 and 1003, resulting in Trp⁻ cells (BY4742-TRP5-CORE). Cells containing the RE-DSB were transformed without and with the induction of DSB (5 hours in GAL 2%) with two 96-nt IROs TRP5.e and TRP5.f, or 51-mres TRP5.e2 and TRP5.f2, or 41-mers TRP5.e3 and TRP5f3, or 31-mers TRP5.e4 and TRP5.f4 containing the BamHI mutation site adjacent to the cassette insertion site, and subsequently Trp⁺ colonies were isolated (Table 3).

TABLE 3

Frequency of IRO mutagenesis after DSB induction

| DSB Induction status[a] | IRO species used[b] | Trp⁺ clones[c] | Trp⁺ clones Dil 10² x[d] | Trp⁺ clones Dil 10⁴ x[e] | viable clones Dil 10⁵ x[f] |
|---|---|---|---|---|---|
| No induction | — | 0 | | | |
| No induction | TRP5.e+f | 417.25[g] | 3.75 | | 282.25 |
| No induction | TRP5.e2+f2 | 40 | | | 52 |
| No induction | TRP5.e3+f3 | 0 | | | 53 |
| No induction | TRP5.e4+f4 | 0 | | | 33 |
| induction | — | 0 | | | |
| induction | TRP5.e+f | ~10⁶ | ~10⁴ | 185.75 | 480 |
| induction | TRP5.e2+f2 | ~5000 | 429.3 | 3.67 | 406 |
| induction | TRP5.e3+f3 | 25.67 | | | 332 |
| induction | TRP5.e4+f4 | 0.3 | | | 322 |

[a]"No induction": cells were grown in glucose media; "induction": cells were grown in the presence of 2% galactose for 5 hours.
[b]IROs were added directly to the cells.
[c]Number of Trp⁺ clones grown on a Trp⁻ plate after transformation with 0.5 nmoles of each IRO.
[d]Number of Trp⁺ clones grown on a Trp⁻ plate after a 10² dilution, after transformation with 0.5 nmoles of each IRO.
[e]Number of Trp⁺ clones grown on a Trp⁻ plate after a 10⁴ dilution, after transformation with 0.5 nmoles of each IRO.
[f]Total number of viable clones grown on a YPD plate after a 10⁵ dilution, after transformation with 0.5 nmoles of each IRO.
[g]Mean number of clones from three to four independent transformation experiments.

Direct replica plating of the colonies grown on YPD (last colon on right of Table 3) on Trp⁻ media gave 2 to 5% Trp⁺ clones. This is the efficiency of targeting with IROs after induction of DSB.

Example 6

Deletion of Genomic Sequences

The delitto perfetto strategy (e.g., Example 1) was used to delete the up to 16 kb of genomic DNA, such that no heterologous DNA was retained after the deletion process was complete. The original CORE-cassette was targeted by standard homologous recombination techniques into BY4742 strain in the TRP5 locus as described above. This generated cells that were Ura+(5-FOA sensitive) and G418 resistant.

A series of four 60-mers (designated 1Stu.a, 1Stu.b, 2Stu.a and 2Stu.b (SEQ ID NOs: 55-58, respectively)) were designed with a 20 base overlap at their 3' ends containing also a StuI restriction site. Annealing and in vitro extension of 1Stu.a and 1Stu.b, 1Stu.a and 2Stu.b, 2Stu.a and 1Stu.b, 2Stu.a and 2Stu.b resulted in a 100-bp double-strand molecule that contains 50 bp homologous to the sequence upstream and downstream regions of the CORE-cassette. Cells were transformed with these double-stranded molecules and transformants 5-FOA resistant G418 sensitive clones were isolated as described previously. 1Stu.a and 1Stu.b are designed to make a16 kb deletion, 1Stu.a and 2Stu.b are designed to make a 10.3 deletion, 2Stu.a and 1Stu.b are designed to make a 8 kb deletion, 2Stu.a and 2Stu.b are designed to make a 3.2 kb deletion aruond the TRP5 locus on chromosome VII.

The number (from three independent transformation events) of 5-FOA resistant (5-FOA^R), G418 sensitive (G418^s) clones relative to the different size deletions made using IROs are the following: 80.5 for the 3.2 kb deletion, 27 for the 8 kb deletion, 3.5 for the 10.3 kb deletion, and 2,5 for the 16 kb deletion. All the G418^s clones tested by colony PCR using CGR 1.1 and STT3.1 primers had lost the cassette and showed the correct StuI restriction pattern.

Large deletions similar to those disclosed in this example also can be generated using the delitto perfetto-DSB system.

Example 7

Targeting by IROs using the Delitto Perfetto-DSB Approach where Homologous Recombination is Severely Impaired (e.g., rad52-null Background)

As discussed herein, in the delitto perfetto system, the integration of IROs (whether presented singly or as pairs to cells) replacing the original CORE-cassette, was dependent on the RAD52 gene and appeared to be partially dependent on RAD50 and MRE11. It has now been surprisingly found that, once a CORE-DSB (or RE-DSB) cassette is placed into the genome, the DSB-enhanced approach can be used even in the absence of a highly efficient recombination systems.

Since the induction of a DSB in the RE-DSB cassette results in an extremely efficient targeting using IROs, the change in targeting efficiency was examined in the absence of the RAD52 gene. Wild-type and mutant (RAD52::LEU2; two independent isolates) strains were transformed with a control centromeric plasmid Ycp50 (Rose et al., Gene, 60:237-243, 1987) (containing the URA3 gene), or the following TRP5 IROs: TRP5.e+f, TRP5.e2+f2, TRP5.e3+f3 and TRP5.e4+f4.

In repeated transformations with YCp50, the wild-type transformation level was about 2-3-fold higher than for the rad52 mutant, apparently due to reduced plating efficiency in the rad52 mutant. Complete RAD52 dependence was observed in the absence of DSB induction. However, after DSB induction a high level of IRO targeting was obeserved (Table 4). These results indicate that oligonucleotide replacement during delitto perfetto-DSB mutagenesis can still occur in the absence of RAD52, highlighting a residual level of homologous recombination targeting independent from RAD52 function.

TABLE 4

Frequency of IRO targeting after DSB induction in a rad52-null background

| DSB Induction status[a] | Strain[b] | IRO species used[c] | Trp⁺ clones[d] |
|---|---|---|---|
| No induction | Δrad52 (1)/(2) | — | 0 |
| No induction | Δrad52 (1)/(2) | TRP5.e+f | 0 |
| No induction | Δrad52 (1)/(2) | TRP5.e2+f2 | 0 |
| No induction | Δrad52 (1)/(2) | TRP5.e3+f3 | 0 |
| No induction | Δrad52 (1)/(2) | TRP5.e4+f4 | 0 |
| Induction | Δrad52 (1) | — | 0 |
| Induction | Δrad52 (1) | TRP5.e+f | 158.67 |
| Induction | Δrad52 (1) | TRP5.e2+f2 | 62.67 |
| Induction | Δrad52 (1) | TRP5.e3+f3 | 2.3 |
| Induction | Δrad52 (1) | TRP5.e4+f4 | 0.67 |

TABLE 4-continued

Frequency of IRO targeting after DSB induction in a rad52-null background

| DSB Induction status[a] | Strain[b] | IRO species used[c] | Trp+ clones[d] |
|---|---|---|---|
| Induction | Δrad52 (2) | — | 0 |
| Induction | Δrad52 (2) | TRP5.e+f | 242 |
| Induction | Δrad52 (2) | TRP5.e2+f2 | 45.3 |
| Induction | Δrad52 (2) | TRP5.e3+f3 | 0 |
| Induction | Δrad52 (2) | TRP5.e4+f4 | 0 |

[a]"No induction": cells were grown in glucose media; "induction": cells were grown in the presence of 2% galactose for 5 hours.
[b]Two independent rad52-nullisolates were used: Δrad52 (1) and Δrad52 (2).
[c]IROs were added directly to the cells.
[d]Number of Trp+ clones growing on a Trp− plate after transformation with 0.5 nmoles of each IRO. Each value is the mean of three independent transformation experiments.

Example 9

Kits

The delitto perfetto and delitto perfetto-DSB mutagenesis methods, and components necessary or useful for carrying out such methods, disclosed herein can be supplied in the form of kits for use in performing in vivo mutagenesis reactions. In such a kit, an amount of one or more of the CORE-cassettes, CORE-DSB cassettes, RE-cassettes, and/or one or more IROs is provided in one or more containers. The nucleic acid molecules may be provided suspended in an aqueous solution or as a freeze-dried or lyophilized powder, for instance. Optionally the kits also include one or more appropriate yeast strains or cells of other organisms.

Kits according to this invention can also include instructions, usually written instructions, to assist the user in performing in vivo mutagenesis reactions with a CORE-cassette and/or one or more IROs. Such instructions can optionally be provided on a computer readable medium.

The container(s) in which the nucleic acid(s) are supplied can be any conventional container that is capable of holding the supplied form, for instance, microfuge tubes, ampoules, or bottles. In some applications, the nucleic acid(s) may be provided in pre-measured single use amounts in individual, typically disposable, tubes or equivalent containers.

The amount of each CORE-cassette or oligonucleotide IRO (or pair of IROs) supplied in the kit can be any appropriate amount, depending for instance on the market to which the product is directed. For instance, if the kit is adapted for research or clinical use, the amount of each IRO provided likely would be an amount sufficient to mediate several transformation reactions. The examples illustrated herein provide guidelines for the amount of IROs useful for a single transformation.

Similarly, in those kits that include oligonucleotide primers for an in vitro amplification reaction, the illustrated embodiments provide guidelines for the amounts useful for a single amplification reaction. In addition, those of ordinary skill in the art know the amount of oligonucleotide primer that is appropriate for use in a single amplification reaction. General guidelines may for instance be found in Innis et al. (*PCR Protocols, A Guide to Methods and Applications*, Academic Press, Inc., San Diego, Calif., 1990), Sambrook et al., Sambrook et al. (In *Molecular Cloning: A Laboratory Manual*, Cold Spring Harbor, N.Y., 1989), and Ausubel et al. (In *Current Protocols in Molecular Biology*, Greene Publ. Assoc. and Wiley-Intersciences, 1992).

In some embodiments, kits may also include one or more of the reagents necessary to carry out PCR amplification reactions, including, for instance, DNA sample preparation reagents, appropriate buffers (e.g., polymerase buffer), salts (e.g., magnesium chloride), and deoxyribonucleotides (dNTPs). In some embodiments, kits may include one or more of the reagents necessary to carry out a transformation reaction. For instance, in kits that are tailored to be used with a yeast (particularly *S. cerevisiae*) system, the kit may include lithium acetate or other buffers or reagents used in yeast transformation.

It may also be advantageous to provide in the kit one or more positive or negative control nucleic acid molecules for use in in vitro amplification or transformation reactions. The design of such control nucleic acid molecules is known to those of ordinary skill in the art. In some embodiments, a control strain may be provided, for instance a negative control strain that is not competent for recombination (e.g., a yeast rad52 strain). Similarly, an appropriate positive control strain might be one that has incorporated into its genome a CORE-cassette that permits detection of successful (or failed) IRO transformation. By way of example, one representative positive control strain is a yeast strain (such as BY4742) containing the CORE-cassette (or a CORE-DSB-cassette, or a RE-DSB-cassette, depending on the kit) in the existing TRP5 mutant gene so that transformation with IROs TRP5.e and TRP5.f (as described above) results in cells showing a Trp+ phenotype and carrying a silent mutation at TRP5 with a new a BamHI site.

This disclosure provides methods for site directed and/or random in vivo mutagenesis, including point mutations, deletions, insertions, and replacements. The disclosure further provides components necessary or useful for such mutagenesis methods, and kits for carrying out such methods. It will be apparent that the precise details of the methods described may be varied or modified without departing from the spirit of the described invention. We claim all such modifications and variations that fall within the scope and spirit of the claims below.

The invention claimed is:

1. A method for introducing a mutation into a target double stranded nucleic acid sequence in a cell, wherein the double stranded nucleic acid sequence comprises a first and a second strand, the method comprising:

introducing a double-stranded nucleic acid cassette into a target nucleic acid sequence at an insertion point, wherein the cassette is a reporter double strand break cassette (RE-DSB-cassette) and comprises:

a first portion homologous to a nucleic acid sequence on a first side of the insertion point;

a second portion homologous to a second nucleic acid sequence on a second side of the insertion point;

a nucleic acid sequence encoding a reporter located between the first portion and the second portion;

a nucleic acid sequence comprising a double-strand break recognition site;

a nucleic acid encoding a double-strand break enzyme that recognizes the double-strand break recognition site and generates a double-strand break at or near the double-strand break recognition site; and an inducible promoter, operably connected with the nucleic acid encoding the double-strand break enzyme;

transforming the cell with a first oligonucleotide comprising:

a nucleic acid sequence homologous to one strand (the chosen strand) of the target nucleic acid sequence at a position on the first side of the insertion point; and a nucleic acid sequence homologous to the same strand of the target nucleic acid sequence at a position on the second side of the insertion point, and comprising at least one nucleotide that differs from the chosen strand of the target nucleic acid sequence; and selecting for complete removal of the nucleic acid sequence encoding the reporter gene, wherein complete removal of the nucleic acid sequence encoding the reporter gene indicates integration of the oligonucleotide sequence comprising the at least one nucleotide that differs from the target nucleic acid sequence.

2. The method of claim 1, wherein the double-stranded nucleic acid cassette further comprises a nucleic acid sequence encoding a counterselectable marker located between the first portion and the second portion, which cassette is referred to as a counterselectable reporter double strand break cassette (CORL-DSB-cassette), and wherein the method further comprises selecting for loss of both the nucleic acid encoding the counterselectable marker and the nucleic acid sequence encoding the reporter gene, wherein loss of both the nucleic acid sequence encoding the counterselectable marker and the nucleic acid sequence encoding the reporter gene indicates integration of the oligonucleotide sequence comprising the at least one nucleotide that differs from the target nucleic acid sequence.

3. The method of claim 1, which method further comprises:

inducing expression of the double strand break enzyme, thereby stimulating a double-strand break within the cassette, which double-strand break stimulates recombination.

4. The method of claim 1, wherein the first oligonucleotide sequence comprises more than one nucleotide that differs from the target nucleic acid sequence.

5. The method of claim 2, wherein transforming the cell with the first oligonucleotide occurs prior to selecting for loss of both the nucleic acid encoding the counterselectable marker and the nucleic acid encoding the reporter gene.

6. The method of claim 1, further comprising transforming the cell with a second oligonucleotide that is at least partially complementary to the first oligonucleotide.

7. The method of claim 6, wherein transforming the cell with the first oligonucleotide occurs concurrently with transforming the cell with the second oligonucleotide.

8. The method of claim 6, wherein the second oligonucleotide comprises:

a nucleic acid sequence homologous to the target nucleic acid sequence at a position to the first side of the insertion point.

9. The method of claim 6, wherein the second oligonucleotide comprises: a nucleic acid sequence homologous to the target nucleic acid sequence at a position to the second side of the insertion point.

10. The method of claim 6, wherein the second oligonucleotide comprises:

a nucleic acid sequence homologous to the target nucleic acid sequence at a position to the first side of the insertion point; and a nucleic acid sequence homologous to the target nucleic acid sequence at a position to the second side of the insertion point.

11. The method of claim 6, wherein the first and/or second oligonucleotide contains at least one random nucleotide change compared to the target nucleic acid sequence.

12. The method of claim 6, wherein the second oligonucleotide is fully complementary to the first oligonucleotide.

13. The method of claim 6, where the 3' ends of the two oligonucleotides are complementary but the first oligonucleotide lacks homology to the second side of the insertion point and the second oligonucleotide lacks homology to the first side of the insertion point.

14. The method of claim 6, where the 3' ends of the two oligonucleotides are complementary but the second oligonucleotide lacks homology to the second side of the insertion point and the first oligonucleotide lacks homology to the first side of the insertion point.

15. The method of claim 6, where the 5' ends of the two oligonucleotides are complementary but the first oligonucleotide lacks homology to the second side of the insertion point and the second oligonucleotide lacks homology to the first side of the insertion point.

16. The method of claim 8, where the 5' ends of the two oligonucleotides are complementary but the second oligonucleotide lacks homology to the second side of the insertion point and the first oligonucleotide lacks homology to the first side of the insertion point.

17. The method of claim 2, wherein the counterselectable marker is KIURA3, URA3, TRP5, TRP1, or a gene encoding a toxin.

18. The method of claim 17, wherein the counterselectable marker is a gene encoding a toxin, and the toxin is an inducible restriction enzyme or an inducible p53 gene.

19. The method of claim 18, wherein the inducible p53 gene is a toxic version.

20. The method of claim 1, wherein the reporter encodes a polypeptide that confers antibiotic resistance to the cell.

21. The method of claim 20, wherein the antibiotic is G418, hygromycin, kanamycin, ampicillin, tetracycline, chloramphenicol, neomycin, zeocin, nourseothricin, cycloheximide or canavanine.

22. The method of claim 1, wherein the reporter encodes a polypeptide from an amino acid or nucleotide synthesis pathway.

23. The method of claim 22, wherein the polypeptide is LEU2, TRP5, TRP1, LYS2, HIS3, or ADE2.

24. The method of claim 1, wherein the first oligonucleotide is at least 30 nucleotides in length.

25. The method of claim 24, wherein the first oligonucleotide is at least 40 nucleotides in length.

26. The method of claim 24, wherein the first oligonucleotide is at least 50 nucleotides in length.

27. The method of claim 24, wherein the first oligonucleotide is at least 80 nucleotides in length.

28. The method of claim 6, wherein the first and the second oligonucleotides are each at least 30 nucleotides in length.

29. The method of claim 28, wherein the first and the second oligonucleotides are each at least 40 nucleotides in length.

30. The method of claim 28, wherein the first and the second oligonucleotides are at least 50 nucleotides in length.

31. The method of claim 28, wherein the first and the second oligonucleotides are at least 80 nucleotides in length.

32. The method of claim 6, wherein the first and the second oligonucleotide are of different lengths.

33. The method of claim 6, wherein the 3' end of the first oligonucleotide overlaps by at least 10 base pairs with the 3' end of the second oligonucleotide.

34. The method of claim 33, wherein the 3' end of the first oligonucleotide overlaps by at least 15 base pairs with the 3' end of the second oligonucleotide.

35. The method of claim 34, wherein the 3' ends of the first and second oligonucleotide can be extended by in vitro polymerization.

36. The method of claim 14, wherein both oligonucleotides differ from the target nucleic acid sequence by at least a single nucleotide.

37. The method of claim 36, wherein at least one nucleotide difference is inside the region of overlap between the first and second oligonucleotides.

38. The method of claim 36, wherein at least one nucleotide difference is outside the region of overlap between the first and second oligonucleotides.

39. The method of claim 1, wherein the cell is a cell of an organism in which homologous recombination can be accomplished.

40. The method of claim 1, wherein the cell is a fungus cell, a bacteria cell, a plant cell, or an animal cell.

41. The method of claim 40, wherein the cell is a fungus cell, and the fungus cell is a yeast cell.

42. The method of claim 40, wherein the cell is an animal cell, and the animal cell is a chicken cell.

43. The method of claim 42, wherein the chicken cell comprises a human chromosome or fragment thereof.

44. The method of claim 2, further comprising analyzing defects in p53 wherein the target nucleic acid sequence is a p53 nucleic acid sequence and a p53 mutant protein is expressed in yeast in such a way that an impact of a defect in the p53 mutant protein can be assessed.

45. The method of claim 44, further comprising assessing a defect in the p53 mutant protein.

46. A method of deleting a target double stranded nucleic acid sequence from within a cell, wherein the target doublestranded nucleic acid sequence comprises a first and a second strand, the method comprising introducing a double-stranded nucleic acid cassette into a target nucleic acid sequence at an insertion point, wherein the cassette is a RE-DSB-cassette and comprises:
a nucleic acid sequence encoding a reporter located between a first portion and a second portion of the RL-DSB-cassette;
a nucleic acid sequence comprising a double-strand break recognition site;
a nucleic acid encoding a double-strand break enzyme that recognizes the double-strand break recognition site and generates a double-strand break at or near the double-strand break recognition site; and
an inducible promoter, operably connected with the nucleic acid encoding the double-strand break enzyme; transforming the cell with a first oligonucleotide comprising:
a nucleic acid sequence homologous to the first strand of a nucleic acid 5' of the nucleic acid of interest; and
a sequence homologous to the first strand of a nucleic acid 3' of the nucleic acid sequence of interest; and
selecting for composite removal of the nucleic acid sequence encoding the reporter gene, wherein complete removal of the nucleic acid sequence encoding the reporter gene from the target double stranded nucleic acid indicates deletion of the target double stranded nucleic acid.

47. The method of claim 46, wherein the double-stranded nucleic acid cassette further comprises a nucleic acid sequence encoding a counterselectable marker located between the first portion and the second portion, which cassette is referred to as a counterselectable reporter double strand break cassette (CORL-DSB-cassette), and wherein the method further comprises selecting for loss of both the nucleic acid sequence encoding the counterselectable marker and the nucleic acid sequence encoding the reporter gene, wherein loss of both the nucleic acid sequence encoding the counterselectable marker and the nucleic acid sequence encoding the reporter gene indicates deletion of the target double stranded nucleic acid.

48. The method of claim 46, which method further comprises:
inducing expression of the double strand break enzyme, thereby stimulating a double-strand break within the cassette, which double-strand break stimulates recombination.

49. The method of claim 46, wherein the target sequence that is deleted is between 1 and about 16,000 bp in length.

50. The method of claim 46, further comprising:
transforming the cell with a second oligonucleotide comprising:
a nucleic acid sequence homologous to the second strand of a nucleic acid 5' of the target double stranded nucleic acid sequence; wherein the sequence of the first oligonucleotide is homologous to at least 10 nucleotides at the 3' end of the sequence of the second oligonucleotide.

51. The method of claim 50, wherein the sequence of the first oligonucleotide is homologous to at least 15 nucleotides at the 3' end of the sequence of the second oligonucleotide.

52. The method of claim 50, wherein the second oligonucleotide further comprises:
a sequence homologous to the second strand of a nucleic acid 3' of the nucleic acid sequence of interest.

53. The method of claim 50, wherein the second oligonucleotide is fully complementary to the first oligonucleotide.

54. The method of claim 47, wherein the counterselectable marker is KlURA3, URA3, TRP5, TRP1, or a gene encoding a toxin.

55. The method of claim 50, wherein the counterselectable marker is KlURA3, URA3, TRP5, TRP1, or a gene encoding a toxin.

56. The method of claim 54, wherein the counterselectable marker is a gene encoding a toxin, and the toxin is an inducible restriction enzyme or an inducible p53 gene.

57. The method of claim 56, wherein the inducible p53 gene is a toxic version.

58. The method of claim 46, wherein the reporter encodes a polypeptide that confers antibiotic resistance to the cell.

59. The method of claim 58, wherein the antibiotic is G418, hygromycin, kanamycin, ampicillin, tetracycline, chloramphenicol, neomycin, zeocin, nourseothricin, cycloheximide or canavanine.

60. The method of claim 46, wherein the reporter encodes a polypeptide from an amino acid or nucleotide synthesis pathway.

61. The method of claim 60, wherein the polypeptide is LEU2, TRP5, TRP1, LYS2, HIS3, or ADE2.

62. The method of claim 46, wherein the first oligonucleotide is at least 30 nucleotides in length.

63. The method of claim 62, wherein the first oligonucleotide is at least 40 nucleotides in length.

64. The method of claim 46, wherein the first oligonucleotide is at least 50 nucleotides in length.

65. The method of claim 46, wherein the first oligonucleotide is at least 80 nucleotides in length.

66. The method of claim 50, wherein the first and the second oligonucleotides are each at least 20 nucleotides in length.

67. The method of claim 66, wherein the first and the second oligonucleotides are each at least 30 nucleotides in length.

68. The method of claim 66, wherein the first and the second oligonucleotides are each at least 40 nucleotides in length.

69. The method of claim 66, wherein the first and the second oligonucleotides are at least 50 nucleotides in length.

70. The method of claim 66, wherein the first and the second oligonucleotides are at least 80 nucleotides in length.

71. The method of claim 66, wherein the first and the second oligonucleotide are of different lengths.

72. The method of claim 66, wherein the first and the second oligonucleotides are at least 20 nucleotides in length and wherein the 3' end of the first oligonucleotide overlaps by at least 10 base pairs with the 3' end of the second oligonucleotide.

73. The method of claim 66, wherein the first and the second oligonucleotides are at least 40 nucleotides in length and wherein the 3' end of the first oligonucleotide overlaps by at least 15 base pairs with the 3' end of the second oligonucleotide.

74. The method of claim 73, wherein the 3' ends of the first and second oligonucleotide can be extended by in vitro polymerization.

75. The method of claim 46, wherein the cell is a cell of an organism in which homologous recombination can be accomplished.

76. The method of claim 46, wherein the cell is a fungus cell, a bacteria cell, a plant cell, or an animal cell.

77. The method of claim 46, further comprising analyzing defects in p53 wherein the target nucleic acid sequence is a p53 nucleic acid sequence and a p53 mutant protein is expressed in yeast in such a way that an impact of a defect in the p53 mutant protein can be assessed.

78. A kit for carrying out in vivo mutagenesis or deletion of a nucleic acid sequence, comprising an amount of RE-DSB-cassette construct or a CORL-DSB-cassette construct, and an amount of an integrative recombinant oligonucleotide.

* * * * *

UNITED STATES PATENT AND TRADEMARK OFFICE
CERTIFICATE OF CORRECTION

PATENT NO. : 7,314,712 B2
APPLICATION NO. : 10/484989
DATED : January 1, 2008
INVENTOR(S) : Storici et al.

It is certified that error appears in the above-identified patent and that said Letters Patent is hereby corrected as shown below:

In the Specification:

Column 3, line 14, "KIURA3" should read -- *K1URA3* --.

Column 5, line 15, "ie." should read -- i.e. --.

Column 6, line 16, "KIURA3" should read -- *K1URA3* --.

Column 6, line 28, "KIURA3" should read -- *K1URA3* --.

Column 9, line 20, "KIURA3" should read -- *K1URA3* --.

Column 9, line 27, "KIURA3" should read -- *K1URA3* --.

Column 9, line 32, "KIURA3" should read -- *K1URA3* --.

Column 9, line 60, "KIURA3" should read -- *K1URA3* --.

Column 12, line 23, "[Na$^-$]" should read -- [Na$^+$] --.

Column 14, line 27, "should e provided" should read -- should be provided --.

Column 16, line 38, "11 type" should read -- II type --.

Column 22, line 22, "KIURA3" should read -- *K1URA3* --.

Column 24, line 11, "KIURA3" should read -- *K1URA3* --.

Column 25, line 24, "construct ," should read -- construct, --.

Column 25, line 59, "KIURA3" should read -- *K1URA3* --.

Column 26, line 5, "KIURA3" should read -- *K1URA3* --.

Column 28, line 4, "BRCA 1" should read -- BRCA1 --.

Column 28, line 21, "et al," should read -- et al., --.

Column 28, line 26, "et al," should read -- et al., --.

UNITED STATES PATENT AND TRADEMARK OFFICE
CERTIFICATE OF CORRECTION

PATENT NO. : 7,314,712 B2
APPLICATION NO. : 10/484989
DATED : January 1, 2008
INVENTOR(S) : Storici et al.

It is certified that error appears in the above-identified patent and that said Letters Patent is hereby corrected as shown below:

Column 28, line 30, "et al," should read -- et al., --.

Column 30, line 45, "included" should read -- include --.

Column 31, line 32, "site-specific specific" should read -- site-specific --.

Column 33, line 24, "2μvector" should read -- 2μ vector --.

Column 34, line 26, "Therefore, could" should read -- Therefore, one could --.

Column 34, line 55, "included" should read -- include --.

Column 35, line 66, "pFA6aKIURA3" should read -- pFA6aKlURA3 --.

Column 36, line 21, "KIURA3" should read -- *KlURA3* --.

Column 36, line 32, "KIURA3" should read -- *KlURA3* --.

Column 36, line 59, "KIURA3" should read -- *KlURA3* --.

Column 37, line 17, "MgSO4" should read -- $MgSO_4$ --.

Column 37, line 44, "...-1, -1..." should read -- ...-1, +1... --.

Column 37, line 44, "5′-48" should read -- 5′+48 --.

Column 37, line 45, "-70), TRP5.d" should read -- -47), TRP5.el --.

Column 38, line 46, "KIURA3-encoding" should read -- *KlURA3*-encoding --.

Column 39, line 36, "plasmid-bome" should read -- plasmid-borne --.

Column 44, line 8, "$G_{418}{}^R$" should read -- $G418^R$ --.

Column 44, line 15, "KIURA3" should read -- *KlURA3* --.

Column 44, line 17, "KIURA3" should read -- *KlURA3* --.

Column 44, line 44, "pFA6aKIURA3" should read -- pFA6aKlURA3 --.

UNITED STATES PATENT AND TRADEMARK OFFICE
CERTIFICATE OF CORRECTION

PATENT NO. : 7,314,712 B2
APPLICATION NO. : 10/484989
DATED : January 1, 2008
INVENTOR(S) : Storici et al.

It is certified that error appears in the above-identified patent and that said Letters Patent is hereby corrected as shown below:

Column 44, line 49, "pFA6aKIURA3" should read -- pFA6a*KlURA3* --.

Column 45, line 4, "KIURA3" should read -- *KlURA3* --.

Column 45, line 20, "61 and 2)." should read -- 61 and 2), --.

Column 45, line 24, "KIURA3" should read -- *KlURA3* --.

Column 45, line 42, "…47;" should read -- …-47; --.

Column 45, line 55, "(KIURA3 and KanMX4), CORE-UH (KIURA3"

should read -- "(*KlURA3* and *KanMX4*), CORE-UH (*KlURA3* --.

Column 45, line 61, "CORE-cassette s" should read -- CORE-cassettes --.

Column 45, line 67, "HygroS" should read -- Hygro$^S$ --.

Column 46, Table 2, column 6, "G418$^5$" should read -- G418$^S$ --.

Column 46, Table 2, footnote d, "G418$^5$" should read -- G418$^S$--.

Column 46, Table 2, footnote d, "Hygro$^5$" should read -- Hygro$^S$ --.

Column 46, line 33, "This" should read -- Thus --.

Column 47, line 45, "KIURA3" should read -- *KlURA3* --.

Column 48, line 9, "5′40" should read -- 5′-40 --.

Column 48, line 22, "KIURA3" should read -- *KlURA3* --.

Column 48, line 23, "HygroR+KIURA3" should read -- Hygro$^R$+*KlURA3* --.

Column 48, line 36, "KIURA3" should read -- *KlURA3* --.

Column 50, line 45, "obeserved" should read -- observed --.

UNITED STATES PATENT AND TRADEMARK OFFICE
CERTIFICATE OF CORRECTION

PATENT NO. : 7,314,712 B2
APPLICATION NO. : 10/484989
DATED : January 1, 2008
INVENTOR(S) : Storici et al.

It is certified that error appears in the above-identified patent and that said Letters Patent is hereby corrected as shown below:

In the Claims:

Column 81, Claim 2, "comprises" should read -- comprises: --.

Column 81, Claim 2, "CORL-" should read -- CORE- --.

Column 82, Claim 16, "claim 8" should read -- claim 6 --.

Column 82, Claim 17, "KIURA3" should read -- KlURA3 --.

Column 84, Claim 47, "CORL-DSB" should read -- CORE-DSB --.

Column 84, Claim 54, "KIURA3" should read -- KlURA3 --.

Column 84, Claim 55, "KIURA3" should read -- KlURA3 --.

Column 86, Claim 78, "CORL-DSB" should read -- CORE-DSB --.

Signed and Sealed this

Twentieth Day of January, 2009

JON W. DUDAS
*Director of the United States Patent and Trademark Office*

UNITED STATES PATENT AND TRADEMARK OFFICE
CERTIFICATE OF CORRECTION

PATENT NO. : 7,314,712 B2
APPLICATION NO. : 10/484989
DATED : January 1, 2008
INVENTOR(S) : Storici et al.

It is certified that error appears in the above-identified patent and that said Letters Patent is hereby corrected as shown below:

In the Specification:

Column 3, line 14, "KIURA3" should read -- *K1URA3* --.

Column 5, line 15, "ie." should read -- i.e. --.

Column 6, line 16, "KIURA3" should read -- *K1URA3* --.

Column 6, line 28, "KIURA3" should read -- *K1URA3* --.

Column 9, line 20, "KIURA3" should read -- *K1URA3* --.

Column 9, line 27, "KIURA3" should read -- *K1URA3* --.

Column 9, line 32, "KIURA3" should read -- *K1URA3* --.

Column 9, line 60, "KIURA3" should read -- *K1URA3* --.

Column 12, line 23, "[Na$^-$]" should read -- [Na$^+$] --.

Column 14, line 27, "should e provided" should read -- should be provided --.

Column 16, line 38, "11 type" should read -- II type --.

Column 22, line 22, "KIURA3" should read -- *K1URA3* --.

Column 24, line 11, "KIURA3" should read -- *K1URA3* --.

Column 25, line 24, "construct ," should read -- construct, --.

Column 25, line 59, "KIURA3" should read -- *K1URA3* --.

Column 26, line 5, "KIURA3" should read -- *K1URA3* --.

Column 28, line 4, "BRCA 1" should read -- BRCA1 --.

Column 28, line 21, "et al," should read -- et al., --.

Column 28, line 26, "et al," should read -- et al., --.

UNITED STATES PATENT AND TRADEMARK OFFICE
CERTIFICATE OF CORRECTION

PATENT NO.      : 7,314,712 B2
APPLICATION NO. : 10/484989
DATED           : January 1, 2008
INVENTOR(S)     : Storici et al.

It is certified that error appears in the above-identified patent and that said Letters Patent is hereby corrected as shown below:

Column 28, line 30, "et al," should read -- et al., --.

Column 30, line 45, "included" should read -- include --.

Column 31, line 32, "site-specific specific" should read -- site-specific --.

Column 33, line 24, "2μvector" should read -- 2μ vector --.

Column 34, line 26, "Therefore, could" should read -- Therefore, one could --.

Column 34, line 55, "included" should read -- include --.

Column 35, line 66, "pFA6aKIURA3" should read -- pFA6aKlURA3 --.

Column 36, line 21, "KIURA3" should read -- *KlURA3* --.

Column 36, line 32, "KIURA3" should read -- *KlURA3* --.

Column 36, line 59, "KIURA3" should read -- *KlURA3* --.

Column 37, line 17, "MgSO4" should read -- MgSO$_4$ --.

Column 37, line 44, "…-1, -1…" should read -- …-1, +1… --.

Column 37, line 44, "5′-48" should read -- 5′+48 --.

Column 37, line 45, "-70), TRP5.d" should read -- -47), TRP5.el --.

Column 38, line 46, "KIURA3-encoding" should read -- *KlURA3*-encoding --.

Column 39, line 36, "plasmid-bome" should read -- plasmid-borne --.

Column 44, line 8, "$G_{418}^R$" should read -- G418$^R$ --.

Column 44, line 15, "KIURA3" should read -- *KlURA3* --.

Column 44, line 17, "KIURA3" should read -- *KlURA3* --.

Column 44, line 44, "pFA6aKIURA3" should read -- pFA6aKlURA3 --.

UNITED STATES PATENT AND TRADEMARK OFFICE
CERTIFICATE OF CORRECTION

PATENT NO.       : 7,314,712 B2
APPLICATION NO.  : 10/484989
DATED            : January 1, 2008
INVENTOR(S)      : Storici et al.

It is certified that error appears in the above-identified patent and that said Letters Patent is hereby corrected as shown below:

Column 44, line 49, "pFA6aKIURA3" should read -- pFA6aKlURA3 --.

Column 45, line 4, "KIURA3" should read -- *KlURA3* --.

Column 45, line 20, "61 and 2)." should read -- 61 and 2), --.

Column 45, line 24, "KIURA3" should read -- *KlURA3* --.

Column 45, line 42, "…47;" should read -- …-47; --.

Column 45, line 55, "(KIURA3 and KanMX4), CORE-UH (KIURA3"

should read -- "(*KlURA3* and *KanMX4*), CORE-UH (*KlURA3* --.

Column 45, line 61, "CORE-cassette s" should read -- CORE-cassettes --.

Column 45, line 67, "HygroS" should read -- Hygro$^S$ --.

Column 46, Table 2, column 6, "G418$^5$" should read -- G418$^S$ --.

Column 46, Table 2, footnote d, "G418$^5$" should read -- G418$^S$ --.

Column 46, Table 2, footnote d, "Hygro$^5$" should read -- Hygro$^S$ --.

Column 46, line 33, "This" should read -- Thus --.

Column 47, line 45, "KIURA3" should read -- *KlURA3* --.

Column 48, line 9, "5′40" should read -- 5′-40 --.

Column 48, line 22, "KIURA3" should read -- *KlURA3* --.

Column 48, line 23, "HygroR+KIURA3" should read -- Hygro$^R$+*KlURA3* --.

Column 48, line 36, "KIURA3" should read -- *KlURA3* --.

Column 50, line 45, "obeserved" should read -- observed --.

UNITED STATES PATENT AND TRADEMARK OFFICE
CERTIFICATE OF CORRECTION

PATENT NO. : 7,314,712 B2
APPLICATION NO. : 10/484989
DATED : January 1, 2008
INVENTOR(S) : Storici et al.

It is certified that error appears in the above-identified patent and that said Letters Patent is hereby corrected as shown below:

In the Claims:

Column 81, Claim 2, line 22, "comprises" should read -- comprises: --.

Column 81, Claim 2, line 26, "CORL-" should read -- CORE- --.

Column 82, Claim 16, line 28, "claim 8" should read -- claim 6 --.

Column 82, Claim 17, line 34, "KIURA3" should read -- KlURA3 --.

Column 84, Claim 47, line 9, "CORL-DSB" should read -- CORE-DSB --.

Column 84, Claim 54, line 45, "KIURA3" should read -- KlURA3 --.

Column 84, Claim 55, line 48, "KIURA3" should read -- KlURA3 --.

Column 86, Claim 78, line 22, "CORL-DSB" should read -- CORE-DSB --.

This certificate supersedes the Certificate of Correction issued January 20, 2009.

Signed and Sealed this

Seventeenth Day of February, 2009

JOHN DOLL
*Acting Director of the United States Patent and Trademark Office*

SEQUENCE LISTING

<160> NUMBER OF SEQ ID NOS: 83

<210> SEQ ID NO 1
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 1
gagctcgttt tcgacactgg                                                    20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
tccttaccat taagttgatc                                                    20

<210> SEQ ID NO 3
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 3
aatttaaggc gaaagaacac tgggcggaag caaaccggca gagctcgttt tcgacactgg         60

<210> SEQ ID NO 4
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 4
gatgtttcat atttatataa ttacattgtt taatattaca tccttaccat taagttgatc         60

<210> SEQ ID NO 5
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 5
tgtttattat ttttagtata caactatata gataatttac atgagctcgt tttcgacact         60
gg                                                                       62

<210> SEQ ID NO 6
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 6
acagtttttc ttggctccta aatttaatga cgaagaataa tccttaccat taagttgatc         60

<210> SEQ ID NO 7
<211> LENGTH: 70
<212> TYPE: DNA
<213> ORGANISM: Artificial sequence
<220> FEATURE:
<223> OTHER INFORMATION: Synthetic oligonucleotide
```

-continued

```
<400> SEQUENCE: 7
cttcatgcat gtctaagaga gttggaaaag ggttttgatg aagctgtcgc gagctcgttt    60
tcgacactgg                                                          70

<210> SEQ ID NO 8
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 8
ggccaatata agaatacaag gatttgaagt cttcccagaa tgtgggatcg tccttaccat    60
taagttgatc                                                          70

<210> SEQ ID NO 9
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 9
gctagaaaaa ttttggtcct gactggtgca ggtgtttcaa cttcattagg gagctcgttt    60
tcgacactgg                                                          70

<210> SEQ ID NO 10
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 10
aatgtttgat ctttgaatag aacccctcag aagatctgaa gtccgggatc tccttaccat    60
taagttgatc                                                          70

<210> SEQ ID NO 11
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 11
tattgagaaa ttatactcaa aacattgata atttggaatc ttatgcggga gagctcgttt    60
tcgacactgg                                                          70

<210> SEQ ID NO 12
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 12
gtggcagtag caaaagagcc atggcactgc accagtttat ctgtgcttat tccttaccat    60
taagttgatc                                                          70

<210> SEQ ID NO 13
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 13
agtcgtcact catggtgatt                                                    20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
agacgacaaa ggcgatgcat                                                    20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
tcgttaatga acagtggata                                                    20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
tcttctgctc agaagattca                                                    20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
acactcaata ttcaacctga                                                    20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
tcctttatct tcgatggcct                                                    20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
```
tcgtggatat ggaacatcct                                              20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
tggatgtgga aaccctgaat                                              20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
ctgacggtgt agtgattggt                                              20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
catggcagca aactgttcct                                              20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
caactcgcaa gagcgtgttc                                              20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
tttgagaacg ccatatgagt                                              20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
cggacttcag atcttctgag                                              20

<210> SEQ ID NO 26
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 26
gattccaaat tatcaatgtt                                                    20

<210> SEQ ID NO 27
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 27 ttcttttct agtggaagtt taccaaaaga aatttaaggc gaaagaacac tgggcggaag         60
caaaccggca tgtaatatta                                                    80

<210> SEQ ID NO 28
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 28
taatgacatt agtgacattt aaaatatgta gatgtttcat atttatataa ttacattgtt        60
taatattaca tgccggtttg                                                    80

<210> SEQ ID NO 29
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 29
ctttcgccgt ccttttcac tcacagcaac aagcagcaag cactaagtac gcagtcaaaa         60
gagagaaaaa atgtaaatta                                                    80

<210> SEQ ID NO 30
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 30
tttaaaacaa actttactgt ttttttttg tttattattt ttagtataca actatataga         60
taatttacat tttttctctc                                                    80

<210> SEQ ID NO 31
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 31
gtcagtatgt cccagaagct cttcatgcat gtctaagaga gttggaaaag ggttttgatg        60
aagctgtcgc ggatcccaca                                                    80

<210> SEQ ID NO 32
```

```
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 32
tttgtgtagt gaagaaggac ggccaatata agaatacaag gatttgaagt cttcccagaa    60
tgtgggatcc gcgacagctt                                                80

<210> SEQ ID NO 33
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 33
tgtgggatcc gcgacagctt catcaaaacc cttttccaac tctcttagac atgcatgaag    60
agcttctggg acatactgac                                                80

<210> SEQ ID NO 34
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 34
aagctgtcgc ggatcccaca ttctgggaag acttcaaatc cttgtattct tatattggcc    60
gtccttcttc actacacaaa                                                80

<210> SEQ ID NO 35
<211> LENGTH: 95
<212> TYPE: DNA
<213> ORGANISM: Artificial sequence
<220> FEATURE:
<223> OTHER INFORMATION: Synthetic oligonucleotide

<400> SEQUENCE: 35
catgcatgtc taagagagtt ggaaaagggt tttgatgaag ctgtcgcgga tcccacattc    60
tgggaagact tcaaatcctt gtattcttat attgg                               95

<210> SEQ ID NO 36
<211> LENGTH: 95
<212> TYPE: DNA
<213> ORGANISM: Artificial sequence
<220> FEATURE:
<223> OTHER INFORMATION: Synthetic oligonucleotide

<400> SEQUENCE: 36
ccaatataag aatacaagga tttgaagtct tcccagaatg tgggatccgc gacagcttca    60
tcaaaaccct tttccaactc tcttagacat gcatg                               95

<210> SEQ ID NO 37
<211> LENGTH: 81
<212> TYPE: DNA
<213> ORGANISM: Artificial sequence
<220> FEATURE:
<223> OTHER INFORMATION: Synthetic oligonucleotide

<400> SEQUENCE: 37
gtctaagaga gttggaaaag ggttttgatg aagctgtcgc ggatcccaca ttctgggaag    60
```
acttcaaatc cttgtattct t                                              81

<210> SEQ ID NO 38
<211> LENGTH: 81
<212> TYPE: DNA
<213> ORGANISM: Artificial sequence
<220> FEATURE:
<223> OTHER INFORMATION: Synthetic oligonucleotide

<400> SEQUENCE: 38
aagaatacaa ggatttgaag tcttcccaga atgtgggatc cgcgacagct tcatcaaaac    60
ccttttccaa ctctcttaga c                                              81

<210> SEQ ID NO 39
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 39
aaaagggttt tgatgaagct gtcgcggatc ccacattctg ggaagacttc a             51

<210> SEQ ID NO 40
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 40
tgaagtcttc ccagaatgtg ggatccgcga cagcttcatc aaaaccctt t              51

<210> SEQ ID NO 41
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 41
tactggacga atttgatgaa atcacaagc acccaattag atttggggac tttggtggtc     60
agtatgtccc agaagctctt                                                80

<210> SEQ ID NO 42
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 42
gatcttctct cttcaaccag atttgagcac cttgacaatg ctcagttaat ctctcagctt    60
tgtgtagtga agaaggacgg                                                80

<210> SEQ ID NO 43
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 43

-continued ttattcaaaa attacatacc gctagaaaaa ttttggtcct gactggtgca ggtgtttcaa      60
cttcattagc gatcccggac                                                  80

<210> SEQ ID NO 44
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 44
ttggggatca tcgagcccca aatgtttgat ctttgaatag aacccctcag aagatctgaa      60
gtccgggatc gctaatgaag                                                  80

<210> SEQ ID NO 45
<211> LENGTH: 95
<212> TYPE: DNA
<213> ORGANISM: Artificial sequence
<220> FEATURE:
<223> OTHER INFORMATION: Synthetic oligonucleotide

<400> SEQUENCE: 45
tagaaaaatt ttggtcctga ctggtgcagg tgtttcaact tcattagcga tcccggactt      60
cagatcttct gagggttct attcaaagat caaac                                  95

<210> SEQ ID NO 46
<211> LENGTH: 95
<212> TYPE: DNA
<213> ORGANISM: Artificial sequence
<220> FEATURE:
<223> OTHER INFORMATION: Synthetic oligonucleotide

<400> SEQUENCE: 46
gtttgatctt tgaatagaac ccctcagaag atctgaagtc cgggatcgct aatgaagttg      60
aaacacctgc accagtcagg accaaaattt ttcta                                 95

<210> SEQ ID NO 47
<211> LENGTH: 95
<212> TYPE: DNA
<213> ORGANISM: Artificial sequence
<220> FEATURE:
<223> OTHER INFORMATION: Synthetic oligonucleotide

<400> SEQUENCE: 47
tagtttcatt aagatgctac aaatgaaagg gaaattattg agaaattata ctcaagccat      60
tgataatttg gaatcttatg cgggaataag cacag                                 95

<210> SEQ ID NO 48
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 48
tccaatggca ggtaacgcag gtggcagtag caaaagagcc atggcactgc accagtttat      60
ctgtgcttat tcccgcataa                                                  80

<210> SEQ ID NO 49
<211> LENGTH: 80
<212> TYPE: DNA
<213> ORGANISM: Artificial sequence

```
<220> FEATURE:
<223> OTHER INFORMATION: Synthetic oligonucleotide

<400> SEQUENCE: 49
gctacaaatg aaagggaaat tattgagaaa ttatactcaa aacattgata atttggaatc      60
ttatgcggga ataagcacag                                                  80

<210> SEQ ID NO 50
<211> LENGTH: 95
<212> TYPE: DNA
<213> ORGANISM: Artificial sequence
<220> FEATURE:
<223> OTHER INFORMATION: Synthetic oligonucleotide

<400> SEQUENCE: 50
tctcaccggg taggttccaa tggcaggtaa cgcaggtggc agtagcaaaa gagccatagc      60
actgcaccag tttatctgtg cttattcccg cataa                                 95

<210> SEQ ID NO 51
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 51
tggaactcaa tgaacctaag ga                                               22

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
agtgtggcaa cgccagcagt                                                  20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
cttgaccaac gtggtcacct                                                  20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
gtaaggccat tgaagatgca                                                  20

<210> SEQ ID NO 55
<211> LENGTH: 60
<212> TYPE: DNA
<213> ORGANISM: Artificial sequence
<220> FEATURE:
<223> OTHER INFORMATION: Synthetic oligonucleotide
```

```
<400> SEQUENCE: 55
catagataca caggtcaata acctacaatg gttaatatct tcttcacagg cctcatgcgt    60

<210> SEQ ID NO 56
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 56
aaaagcaacc gtcgatggtg accatttagc agaggcgaag acgcatgagg cctgtgaaga    60

<210> SEQ ID NO 57
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 57
agaatacaag gatttgaagt cttcccagaa tgtgggatcg tcttcacagg cctcatgcgt    60

<210> SEQ ID NO 58
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 58
gtctaagaga gttggaaaag ggttttgatg aagctgtcgc acgcatgagg cctgtgaaga    60

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
gggaaggtat ggaaggcaga                                                20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
tagtcgtcat caaaccagga                                                20

<210> SEQ ID NO 61
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 61
cttcatgcat gtctaagaga gttggaaaag ggttttgatg aagctgtcgc ttcgtacgct    60
gcaggtcgac                                                           70
```

<210> SEQ ID NO 62
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 62
ggccaatata agaatacaag gatttgaagt cttcccagaa tgtgggatcg ccgcgcgttg    60
gccgattcat    70

<210> SEQ ID NO 63
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 63
gtcggaagat ctcgttggat ggacgcaaag aagt    34

<210> SEQ ID NO 64
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 64
tctgtgagat ctgacttatt atttcaggaa agtttcgg    38

<210> SEQ ID NO 65
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 65
taagaataca aggatttgaa gtcttcccag aatgtgggat cgtagggata acagggtaat    60
ttggatggac gcaaagaagt    80

<210> SEQ ID NO 66
<211> LENGTH: 88
<212> TYPE: DNA
<213> ORGANISM: Artificial sequence
<220> FEATURE:
<223> OTHER INFORMATION: Synthetic oligonucleotide

<400> SEQUENCE: 66
cttcatgcat gtctaagaga gttggaaaag ggttttgatg aagctgtcgc attaccctgt    60
tatccctatt cgtacgctgc aggtcgac    88

<210> SEQ ID NO 67
<211> LENGTH: 88
<212> TYPE: DNA
<213> ORGANISM: Artificial sequence
<220> FEATURE:
<223> OTHER INFORMATION: Synthetic oligonucleotide

<400> SEQUENCE: 67
cttcatgcat gtctaagaga gttggaaaag ggttttgatg aagctgtcgc tagggataac    60
agggtaattt cgtacgctgc aggtcgac    88

<210> SEQ ID NO 68
<211> LENGTH: 100
<212> TYPE: DNA
<213> ORGANISM: Artificial sequence
<220> FEATURE:
<223> OTHER INFORMATION: Synthetic oligonucleotide

<400> SEQUENCE: 68
taagaataca aggatttgaa gtcttcccag aatgtgggat cgtagggata acagggtaat    60
ggattaccct gttatcccta ttggatggac gcaaagaagt                         100

<210> SEQ ID NO 69
<211> LENGTH: 654
<212> TYPE: DNA
<213> ORGANISM: Artificial sequence
<220> FEATURE:
<223> OTHER INFORMATION: Synthetic GAL promoter

<400> SEQUENCE: 69
ttggatggac gcaaagaagt ttaataatca tattacatgg cattaccacc atatacatat    60
ccatatacat atccatatct aatcttactt atatgttgtg gaaatgtaaa gagccccatt   120
atcttagcct aaaaaaacct tctctttgga actttcagta atacgcttaa ctgctcattg   180
ctatattgaa gtacggatta gaagccgccg agcgggtgac agccctccga aggaagactc   240
tcctccgtgc gtcctcgtct tcaccggtcg cgttcctgaa acgcagatgt gcctcgcgcc   300
gcactgctcc gaacaataaa gattctacaa tactagcttt tatggttatg aagaggaaaa   360
attggcagta acctggcccc acaaaccttc aaatgaacga atcaaattaa caaccatagg   420
atgataatgc gattagtttt ttagccttat ttctggggta attaatcagc gaagcgatga   480
tttttgatct attaacagat atataaatgc aaaaactgca taaccacttt aactaatact   540
ttcaacattt tcggtttgta ttacttctta tcaaatgta ataaaagtat caacaaaaaa   600
ttgttaatat acctctatac tttaacgtca aggagaaaaa accccggatc catg         654

<210> SEQ ID NO 70
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 70
cttcatgcat gtctaagaga gttggaaaag ggttttgatg aagctgtcgc catctgggca    60
gatgatgtcg                                                          70

<210> SEQ ID NO 71
<211> LENGTH: 88
<212> TYPE: DNA
<213> ORGANISM: Artificial sequence
<220> FEATURE:
<223> OTHER INFORMATION: Synthetic oligonucleotide

<400> SEQUENCE: 71
cttcatgcat gtctaagaga gttggaaaag ggttttgatg aagctgtcgc attaccctgt    60
tatccctaca tctgggcaga tgatgtcg                                      88

<210> SEQ ID NO 72
<211> LENGTH: 88
<212> TYPE: DNA
<213> ORGANISM: Artificial sequence

```
<220> FEATURE:
<223> OTHER INFORMATION: Synthetic oligonucleotide

<400> SEQUENCE: 72
cttcatgcat gtctaagaga gttggaaaag ggttttgatg aagctgtcgc tagggataac    60
agggtaatca tctgggcaga tgatgtcg                                       88

<210> SEQ ID NO 73
<211> LENGTH: 100
<212> TYPE: DNA
<213> ORGANISM: Artificial sequence
<220> FEATURE:
<223> OTHER INFORMATION: Synthetic oligonucleotide

<400> SEQUENCE: 73
taagaataca aggatttgaa gtcttcccag aatgtgggat cgtagggata acagggtaat    60
ggattaccct gttatcccta ttggatggac gcaaagaagt                         100

<210> SEQ ID NO 74
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 74
tacaatcgat agattgtcgc ac                                             22

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
ttcaatagct catcagtcga                                                20

<210> SEQ ID NO 76
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 76
ccatggcctc cgcgaccggc tgc                                            23

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
tgactgtacc accatccact                                                20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 78
ctgttcgatg ttcagttcga                                              20

<210> SEQ ID NO 79
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 79
gcaggatcgc cgcggctccg ggcg                                         24

<210> SEQ ID NO 80
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 80
ggttttgatg aagctgtcgc ggatcccaca ttctgggaag a                      41

<210> SEQ ID NO 81
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 81
tcttcccaga atgtgggatc cgcgacagct tcatcaaaac c                      41

<210> SEQ ID NO 82
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 82
tgatgaagct gtcgcggatc ccacattctg g                                 31

<210> SEQ ID NO 83
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 83
ccagaatgtg ggatccgcga cagcttcatc a                                 31
```